US012744126B2

(12) United States Patent
Ryan et al.

(10) Patent No.: US 12,744,126 B2
(45) Date of Patent: Sep. 22, 2026

(54) SYSTEMS AND METHODS FOR DETERMINING ANEUPLOIDY RISK USING SAMPLE FETAL FRACTION

(71) Applicant: Natera, Inc., San Carlos, CA (US)

(72) Inventors: Allison Ryan, Belmont, CA (US); Katie Kobara, San Francisco, CA (US); Zachary Demko, San Francisco, CA (US); Susan J. Gross, Bronx, NY (US)

(73) Assignee: Natera, Inc., San Carlos, CA (US)

( * ) Notice: Subject to any disclaimer, the term of this patent is extended or adjusted under 35 U.S.C. 154(b) by 0 days.

(21) Appl. No.: 17/365,786

(22) Filed: Jul. 1, 2021

(65) Prior Publication Data

US 2021/0327542 A1 Oct. 21, 2021

Related U.S. Application Data

(63) Continuation of application No. 15/186,774, filed on Jun. 20, 2016, now abandoned.

(60) Provisional application No. 62/182,085, filed on Jun. 19, 2015.

(51) Int. Cl.

| | |
|---|---|
| ***G16H 50/30*** | (2018.01) |
| ***C12Q 1/6869*** | (2018.01) |
| ***C12Q 1/6883*** | (2018.01) |
| ***G16B 20/10*** | (2019.01) |
| ***G16H 50/70*** | (2018.01) |

(52) U.S. Cl.

CPC ............. *G16H 50/30* (2018.01); *G16H 50/70* (2018.01); *C12Q 1/6869* (2013.01); *C12Q 1/6883* (2013.01); *G16B 20/10* (2019.02)

(58) Field of Classification Search

None

See application file for complete search history.

(56) References Cited

U.S. PATENT DOCUMENTS

| | | | |
|---|---|---|---|
| 3,957,654 | A | 5/1976 | Ayres |
| 4,040,785 | A | 8/1977 | Kim et al. |
| 4,683,195 | A | 7/1987 | Mullis et al. |
| 4,942,124 | A | 7/1990 | Church et al. |
| 5,180,812 | A | 1/1993 | Dower et al. |
| 5,314,809 | A | 5/1994 | Erlich et al. |
| 5,319,071 | A | 6/1994 | Dower et al. |
| 5,464,937 | A | 11/1995 | Sims et al. |
| 5,486,477 | A | 1/1996 | Carver |
| 5,488,032 | A | 1/1996 | Dower et al. |
| 5,492,888 | A | 2/1996 | Dower et al. |
| 5,569,582 | A | 10/1996 | Tavernarakis et al. |
| 5,595,890 | A | 1/1997 | Newton et al. |
| 5,635,366 | A | 6/1997 | Cooke et al. |
| 5,645,988 | A | 7/1997 | Vande Woude et al. |
| 5,648,220 | A | 7/1997 | Bianchi et al. |
| 5,714,320 | A | 2/1998 | Kool |
| 5,716,776 | A | 2/1998 | Bogart |
| 5,736,033 | A | 4/1998 | Coleman et al. |
| 5,753,467 | A | 5/1998 | Jensen et al. |
| 5,824,467 | A | 10/1998 | Mascarenhas |
| 5,854,033 | A | 12/1998 | Lizardi |
| 5,860,917 | A | 1/1999 | Comanor et al. |
| 5,891,734 | A | 4/1999 | Gill et al. |
| 5,952,170 | A | 9/1999 | Stroun et al. |
| 5,962,223 | A | 10/1999 | Whiteley et al. |
| 5,972,602 | A | 10/1999 | Hyland et al. |
| 5,976,790 | A | 11/1999 | Pinkel et al. |
| 5,994,148 | A | 11/1999 | Stewart et al. |
| 6,001,611 | A | 12/1999 | Will |
| 6,025,128 | A | 2/2000 | Veltri et al. |
| 6,066,454 | A | 5/2000 | Lipshutz et al. |
| 6,100,029 | A | 8/2000 | Lapidus et al. |
| 6,108,635 | A | 8/2000 | Herren et al. |
| 6,124,120 | A | 9/2000 | Lizardi |
| 6,143,496 | A | 11/2000 | Brown et al. |
| 6,156,504 | A | 12/2000 | Gocke et al. |

(Continued)

FOREIGN PATENT DOCUMENTS

| | | | |
|---|---|---|---|
| BR | 112017023232 | A2 | 8/2018 |
| CA | 2875281 | A1 | 12/2013 |

(Continued)

OTHER PUBLICATIONS

US 8,501,409 B2, 08/2013, Simen et al. (withdrawn)

Kim SK. Determination of fetal fraction from the plasma of pregnant women using sequence read counts. Prenatal Diagnosis 35: 810-815. (Year: 2015).*

Benn P. Theoretical performance of non-invasive prenatal testing for chromosomal imbalances using counting of cell-free DNA fragments in maternal plasma. Prenatal Diagnosis 34: 778-783. (Year: 2014).*

(Continued)

*Primary Examiner* — Olivia M. Wise
*Assistant Examiner* — Robert J. Kallal

(57) ABSTRACT

Disclosed herein are system, method, and computer program product embodiments for determining aneuploidy risk in a target sample of maternal blood or plasma based on the amount of fetal DNA. An embodiment operates by receiving known genetic data from known prenatal testing samples and genetic data for the target sample. A fetal fraction distribution is determined for the known genetic data based on gestational age and the maternal weight associated with the target sample. A model is then generated based on a fixed ratio reduction of the determined fetal fraction distribution. A fetal fraction based data likelihood for the target sample is then determined for each of the plurality of ploidy states using the generated model. An aneuploidy risk score is then outputted based on applying a Bayesian probability determination that combines each fetal fraction based data likelihood with a previously determined risk score as a conditional value.

14 Claims, 15 Drawing Sheets

(56) References Cited

U.S. PATENT DOCUMENTS

| | | | |
|---|---|---|---|
| 6,180,349 | B1 | 1/2001 | Ginzinger |
| 6,214,558 | B1 | 4/2001 | Shuber et al. |
| 6,221,603 | B1 | 4/2001 | Mahtani |
| 6,235,472 | B1 | 5/2001 | Landegren et al. |
| 6,258,540 | B1 | 7/2001 | Lo et al. |
| 6,300,077 | B1 | 10/2001 | Shuber et al. |
| 6,329,179 | B1 | 12/2001 | Kopreski |
| 6,335,167 | B1 | 1/2002 | Pinkel et al. |
| 6,440,706 | B1 | 8/2002 | Vogelstein et al. |
| 6,479,235 | B1 | 11/2002 | Schumm et al. |
| 6,489,135 | B1 | 12/2002 | Parrott et al. |
| 6,605,451 | B1 | 8/2003 | Marmaro et al. |
| 6,617,137 | B2 | 9/2003 | Dean et al. |
| 6,720,140 | B1 | 4/2004 | Hartley et al. |
| 6,794,140 | B1 | 9/2004 | Goldsborough |
| 6,807,491 | B2 | 10/2004 | Pavlovic et al. |
| 6,852,487 | B1 | 2/2005 | Barany et al. |
| 6,858,412 | B2 | 2/2005 | Willis et al. |
| 6,927,028 | B2 | 8/2005 | Lo et al. |
| 6,958,211 | B2 | 10/2005 | Vingerhoets et al. |
| 6,964,847 | B1 | 11/2005 | Englert |
| 7,035,739 | B2 | 4/2006 | Schadt et al. |
| 7,058,517 | B1 | 6/2006 | Denton et al. |
| 7,058,616 | B1 | 6/2006 | Larder et al. |
| 7,101,663 | B2 | 9/2006 | Godfrey et al. |
| 7,153,656 | B2 | 12/2006 | Nolan et al. |
| 7,218,764 | B2 | 5/2007 | Vaisberg et al. |
| 7,297,485 | B2 | 11/2007 | Bornarth et al. |
| 7,332,277 | B2 | 2/2008 | Dhallan |
| 7,410,764 | B2 | 8/2008 | Gocke et al. |
| 7,414,118 | B1 | 8/2008 | Mullah et al. |
| 7,442,506 | B2 | 10/2008 | Dhallan |
| 7,459,273 | B2 | 12/2008 | Jones et al. |
| 7,537,897 | B2 | 5/2009 | Brenner et al. |
| 7,645,576 | B2 | 1/2010 | Lo et al. |
| 7,655,399 | B2 | 2/2010 | Cantor et al. |
| 7,700,325 | B2 | 4/2010 | Cantor et al. |
| 7,718,367 | B2 | 5/2010 | Lo et al. |
| 7,718,370 | B2 | 5/2010 | Dhallan |
| 7,727,720 | B2 | 6/2010 | Dhallan |
| 7,741,463 | B2 | 6/2010 | Gormley et al. |
| 7,785,798 | B2 | 8/2010 | Cantor et al. |
| 7,790,393 | B2 | 9/2010 | Lyamichev et al. |
| 7,790,418 | B2 | 9/2010 | Mayer |
| 7,805,282 | B2 | 9/2010 | Casey |
| 7,838,647 | B2 | 11/2010 | Hahn et al. |
| 7,888,017 | B2 | 2/2011 | Quake |
| 7,981,609 | B2 | 7/2011 | Rubin et al. |
| 8,008,018 | B2 | 8/2011 | Quake et al. |
| 8,024,128 | B2 | 9/2011 | Rabinowitz |
| 8,133,719 | B2 | 3/2012 | Drmanac et al. |
| 8,137,912 | B2 | 3/2012 | Kapur et al. |
| 8,168,389 | B2 | 5/2012 | Shoemaker et al. |
| 8,173,370 | B2 | 5/2012 | Oeth et al. |
| 8,195,415 | B2 | 6/2012 | Fan et al. |
| 8,236,503 | B2 | 8/2012 | Faham et al. |
| 8,296,076 | B2 | 10/2012 | Fan et al. |
| 8,304,187 | B2 | 11/2012 | Fernando |
| 8,318,430 | B2 | 11/2012 | Chuu et al. |
| 8,318,434 | B2 | 11/2012 | Cuppens et al. |
| 8,323,897 | B2 | 12/2012 | Andersen et al. |
| 8,372,584 | B2 | 2/2013 | Shoemaker et al. |
| 8,389,557 | B2 | 3/2013 | Singh et al. |
| 8,389,578 | B2 | 3/2013 | Went et al. |
| 8,450,063 | B2 | 5/2013 | Dube et al. |
| 8,467,976 | B2 | 6/2013 | Lo et al. |
| 8,515,679 | B2 | 8/2013 | Rabinowitz et al. |
| 8,532,930 | B2 | 9/2013 | Rabinowitz et al. |
| 8,609,338 | B2 | 12/2013 | Mitchell et al. |
| 8,679,741 | B2 | 3/2014 | Hoyal-Wrightson et al. |
| 8,682,592 | B2 | 3/2014 | Rabinowitz et al. |
| 8,703,652 | B2 | 4/2014 | Quake et al. |
| 8,706,422 | B2 | 4/2014 | Lo et al. |
| 8,748,103 | B2 | 6/2014 | Faham et al. |
| 8,822,153 | B2 | 9/2014 | Hayes et al. |
| 8,825,412 | B2 | 9/2014 | Rabinowitz et al. |
| 9,005,894 | B2 | 4/2015 | Ladner et al. |
| 9,051,602 | B2 | 6/2015 | Oliphant et al. |
| 9,085,798 | B2 | 7/2015 | Chee |
| 9,206,475 | B2 | 12/2015 | Gerdes et al. |
| 9,228,234 | B2 | 1/2016 | Rabinowitz et al. |
| 9,290,815 | B2 | 3/2016 | Di Pasquale et al. |
| 9,323,888 | B2 | 4/2016 | Rava et al. |
| 9,364,829 | B2 | 6/2016 | Heid et al. |
| 9,404,150 | B2 | 8/2016 | Lee et al. |
| 9,424,392 | B2 | 8/2016 | Rabinowitz et al. |
| 9,453,257 | B2 | 9/2016 | Hoyal-Wrightson et al. |
| 9,476,095 | B2 | 10/2016 | Vogelstein et al. |
| 9,487,829 | B2 | 11/2016 | Vogelstein et al. |
| 9,493,828 | B2 | 11/2016 | Rava et al. |
| 9,506,119 | B2 | 11/2016 | Faham et al. |
| 9,598,731 | B2 | 3/2017 | Talasaz |
| 9,677,118 | B2 | 6/2017 | Zimmermann et al. |
| 9,784,742 | B2 | 10/2017 | Benz et al. |
| 9,926,593 | B2 | 3/2018 | Ehrich et al. |
| 9,957,558 | B2 | 5/2018 | Leamon et al. |
| 10,011,870 | B2 | 7/2018 | Zimmermann et al. |
| 10,017,810 | B2 | 7/2018 | Tafrate et al. |
| 10,041,127 | B2 | 8/2018 | Talasaz |
| 10,061,890 | B2 | 8/2018 | Rabinowitz et al. |
| 10,081,839 | B2 | 9/2018 | Rabinowitz et al. |
| 10,083,273 | B2 | 9/2018 | Rabinowitz et al. |
| 10,174,369 | B2 | 1/2019 | Rabinowitz et al. |
| 10,179,937 | B2 | 1/2019 | Babiarz et al. |
| 10,227,652 | B2 | 3/2019 | Rabinowitz et al. |
| 10,229,244 | B2 | 3/2019 | Ghosh |
| 10,240,202 | B2 | 3/2019 | Rabinowitz et al. |
| 10,260,096 | B2 | 4/2019 | Rabinowitz et al. |
| 10,262,755 | B2 | 4/2019 | Babiarz et al. |
| 10,266,893 | B2 | 4/2019 | Rabinowitz et al. |
| 10,308,981 | B2 | 6/2019 | Sparks et al. |
| 10,316,362 | B2 | 6/2019 | Babiarz et al. |
| 10,351,906 | B2 | 7/2019 | Zimmermann et al. |
| 10,385,396 | B2 | 8/2019 | Mitchell et al. |
| 10,392,664 | B2 | 8/2019 | Rabinowitz et al. |
| 10,450,597 | B2 | 10/2019 | Tafrate et al. |
| 10,472,680 | B2 | 11/2019 | Mitchell et al. |
| 10,522,242 | B2 | 12/2019 | Rabinowitz et al. |
| 10,526,658 | B2 | 1/2020 | Babiarz et al. |
| 10,538,814 | B2 | 1/2020 | Babiarz et al. |
| 10,557,172 | B2 | 2/2020 | Babiarz et al. |
| 10,597,708 | B2 | 3/2020 | Zimmermann et al. |
| 10,597,709 | B2 | 3/2020 | Zimmermann et al. |
| 10,597,723 | B2 | 3/2020 | Babiarz et al. |
| 10,640,819 | B2 | 5/2020 | Rosenfeld et al. |
| 10,655,180 | B2 | 5/2020 | Babiarz et al. |
| 10,683,552 | B2 | 6/2020 | Giulio et al. |
| 10,711,309 | B2 | 7/2020 | Rabinowitz et al. |
| 10,731,220 | B2 | 8/2020 | Babiarz et al. |
| 10,774,380 | B2 | 9/2020 | Ryan et al. |
| 10,793,912 | B2 | 10/2020 | Babiarz et al. |
| 10,894,976 | B2 | 1/2021 | Stray et al. |
| 11,111,543 | B2 | 9/2021 | Rabinowitz et al. |
| 11,111,544 | B2 | 9/2021 | Rabinowitz et al. |
| 11,111,545 | B2 | 9/2021 | Babiarz et al. |
| 11,130,995 | B2 | 9/2021 | Quake et al. |
| 11,319,596 | B2 | 5/2022 | Babiarz et al. |
| 11,371,100 | B2 | 6/2022 | Babiarz et al. |
| 11,519,035 | B2 | 12/2022 | Rabinowtiz et al. |
| 2001/0051341 | A1 | 12/2001 | Lo et al. |
| 2001/0053519 | A1 | 12/2001 | Fodor et al. |
| 2002/0006622 | A1 | 1/2002 | Bradley et al. |
| 2002/0107640 | A1 | 8/2002 | Ideker et al. |
| 2002/0119478 | A1 | 8/2002 | Umansky et al. |
| 2002/0182622 | A1 | 12/2002 | Nakamura et al. |
| 2002/0197630 | A1 | 12/2002 | Knapp et al. |
| 2003/0009295 | A1 | 1/2003 | Markowitz et al. |
| 2003/0040620 | A1 | 2/2003 | Langmore et al. |
| 2003/0044388 | A1 | 3/2003 | Lo et al. |
| 2003/0065535 | A1 | 4/2003 | Karlov et al. |
| 2003/0077586 | A1 | 4/2003 | Pavlovic et al. |
| 2003/0087276 | A1 | 5/2003 | Kopreski et al. |
| 2003/0101000 | A1 | 5/2003 | Bader et al. |
| 2003/0108900 | A1 | 6/2003 | Oliphant et al. |

(56) References Cited

U.S. PATENT DOCUMENTS

2003/0119004 A1 6/2003 Wenz et al.
2003/0138780 A1 7/2003 Gill et al.
2003/0148301 A1 8/2003 Aono et al.
2003/0191005 A1 10/2003 Coelho et al.
2003/0211489 A1 11/2003 Shen et al.
2003/0228613 A1 12/2003 Bornarth et al.
2003/0232348 A1 12/2003 Jones et al.
2003/0232353 A1 12/2003 Kennedy et al.
2003/0235848 A1 12/2003 Neville et al.
2004/0009518 A1 1/2004 Lo et al.
2004/0033596 A1 2/2004 Threadgill et al.
2004/0067493 A1 4/2004 Matsuzaki et al.
2004/0096874 A1 5/2004 Neville et al.
2004/0115629 A1 6/2004 Panzer et al.
2004/0117346 A1 6/2004 Stoffel et al.
2004/0126760 A1 7/2004 Broude
2004/0136967 A1 7/2004 Weiss et al.
2004/0137470 A1 7/2004 Dhallan et al.
2004/0146866 A1 7/2004 Fu
2004/0157243 A1 8/2004 Huang et al.
2004/0185495 A1 9/2004 Schueler et al.
2004/0197797 A1 10/2004 Inoko et al.
2004/0209299 A1 10/2004 Pinter et al.
2004/0229231 A1 11/2004 Frudakis et al.
2004/0236518 A1 11/2004 Pavlovic et al.
2004/0259100 A1 12/2004 Gunderson et al.
2005/0009069 A1 1/2005 Liu et al.
2005/0043894 A1 2/2005 Fernandez
2005/0049793 A1 3/2005 Paterlini-Brechot
2005/0053950 A1 3/2005 Ubani et al.
2005/0064476 A1 3/2005 Huang et al.
2005/0079521 A1 4/2005 Beaulieu et al.
2005/0079535 A1 4/2005 Kirchgesser et al.
2005/0123914 A1 6/2005 Katz et al.
2005/0130173 A1 6/2005 Leamon et al.
2005/0142577 A1 6/2005 Jones et al.
2005/0144664 A1 6/2005 Smith et al.
2005/0164241 A1 7/2005 Hahn et al.
2005/0164252 A1 7/2005 Yeung
2005/0216207 A1 9/2005 Kermani
2005/0221341 A1 10/2005 Shimkets et al.
2005/0227263 A1 10/2005 Green et al.
2005/0250111 A1 11/2005 Xie et al.
2005/0255508 A1 11/2005 Casey et al.
2005/0272073 A1 12/2005 Vaisberg et al.
2005/0282185 A1 12/2005 Lo et al.
2006/0014179 A1 1/2006 Roberts
2006/0019278 A1 1/2006 Lo et al.
2006/0040300 A1 2/2006 Dapprich et al.
2006/0046258 A1 3/2006 Lapidus et al.
2006/0051799 A1 3/2006 Iwaki et al.
2006/0052945 A1 3/2006 Rabinowitz et al.
2006/0057618 A1 3/2006 Piper et al.
2006/0068369 A1 3/2006 Coelho et al.
2006/0068394 A1 3/2006 Langmore et al.
2006/0088574 A1 4/2006 Manning et al.
2006/0088871 A1 4/2006 Finkelstein et al.
2006/0088912 A1 4/2006 Yan et al.
2006/0094010 A1 5/2006 Giles et al.
2006/0099614 A1 5/2006 Gill et al.
2006/0121452 A1 6/2006 Dhallan
2006/0134662 A1 6/2006 Pratt et al.
2006/0141499 A1 6/2006 Sher et al.
2006/0210997 A1 9/2006 Myerson et al.
2006/0216153 A1 9/2006 Wobben et al.
2006/0216738 A1 9/2006 Wada et al.
2006/0228721 A1 10/2006 Leamon et al.
2006/0229823 A1 10/2006 Liu
2006/0234264 A1 10/2006 Hardenbol
2006/0248031 A1 11/2006 Kates et al.
2006/0281105 A1 12/2006 Li et al.
2006/0292599 A1 12/2006 Ritz et al.
2007/0020640 A1 1/2007 McCloskey et al.
2007/0027636 A1 2/2007 Rabinowitz
2007/0031857 A1 2/2007 Makarov et al.
2007/0037166 A1 2/2007 Wohlgemuth et al.
2007/0042384 A1 2/2007 Li et al.
2007/0059700 A1 3/2007 Tao et al.
2007/0059707 A1 3/2007 Cantor et al.
2007/0122805 A1 5/2007 Cantor et al.
2007/0128624 A1 6/2007 Gormley et al.
2007/0134658 A1 6/2007 Bohmer
2007/0178478 A1 8/2007 Dhallan
2007/0178501 A1 8/2007 Rabinowitz et al.
2007/0184467 A1 8/2007 Rabinowitz et al.
2007/0202525 A1 8/2007 Quake et al.
2007/0202536 A1 8/2007 Yamanishi et al.
2007/0207466 A1 9/2007 Cantor et al.
2007/0212689 A1 9/2007 Bianchi et al.
2007/0231823 A1 10/2007 McKernan et al.
2007/0243549 A1 10/2007 Bischoff
2007/0259351 A1 11/2007 Chinitz
2008/0020390 A1 1/2008 Mitchell et al.
2008/0026390 A1 1/2008 Stoughton et al.
2008/0038733 A1 2/2008 Bischoff et al.
2008/0050739 A1 2/2008 Stoughton et al.
2008/0070792 A1 3/2008 Stoughton
2008/0071076 A1 3/2008 Hahn et al.
2008/0085836 A1 4/2008 Kearns et al.
2008/0090239 A1 4/2008 Shoemaker et al.
2008/0096766 A1 4/2008 Lee
2008/0102455 A1 5/2008 Poetter
2008/0138809 A1 6/2008 Kapur et al.
2008/0161420 A1 7/2008 Shuber et al.
2008/0164204 A1 7/2008 Hatamian et al.
2008/0182244 A1 7/2008 Tafas et al.
2008/0193927 A1 8/2008 Mann et al.
2008/0220422 A1 9/2008 Shoemaker et al.
2008/0234142 A1 9/2008 Lietz
2008/0243398 A1 10/2008 Rabinowitz et al.
2008/0280292 A1 11/2008 Wangh et al.
2008/0286783 A1 11/2008 Hosono et al.
2008/0293589 A1 11/2008 Shapero
2008/0299562 A1 12/2008 Oeth et al.
2008/0305473 A1 12/2008 Chowdary et al.
2009/0023190 A1 1/2009 Lao et al.
2009/0029377 A1 1/2009 Lo et al.
2009/0053719 A1 2/2009 Lo et al.
2009/0087847 A1 4/2009 Lo et al.
2009/0098534 A1 4/2009 Weier et al.
2009/0099041 A1 4/2009 Church et al.
2009/0143570 A1 6/2009 Jiang et al.
2009/0176234 A1 7/2009 Drmanac et al.
2009/0176662 A1 7/2009 Rigatti et al.
2009/0221620 A1 9/2009 Luke et al.
2009/0228299 A1 9/2009 Kangarloo et al.
2009/0233802 A1 9/2009 Bignell et al.
2009/0253183 A1 10/2009 Han
2009/0263800 A1 10/2009 Wohlgemuth et al.
2009/0280479 A1 11/2009 Hoon et al.
2009/0317817 A1 12/2009 Oeth et al.
2010/0012598 A1 1/2010 Dicesare et al.
2010/0035232 A1 2/2010 Ecker et al.
2010/0041048 A1 2/2010 Diehl et al.
2010/0086914 A1 4/2010 Bentley et al.
2010/0105049 A1 4/2010 Ehrich et al.
2010/0112575 A1 5/2010 Fan et al.
2010/0112586 A1 5/2010 Stoughton et al.
2010/0112590 A1 5/2010 Lo et al.
2010/0120038 A1 5/2010 Mir et al.
2010/0124751 A1 5/2010 Quake et al.
2010/0129361 A1 5/2010 Ho et al.
2010/0129792 A1 5/2010 Makrigiorgos et al.
2010/0129874 A1 5/2010 Mitra et al.
2010/0138165 A1 6/2010 Fan et al.
2010/0155343 A1 6/2010 Battles et al.
2010/0171954 A1 7/2010 Quake et al.
2010/0173394 A1 7/2010 Colston et al.
2010/0184043 A1 7/2010 Mitchell et al.
2010/0184069 A1 7/2010 Fernando et al.
2010/0184152 A1 7/2010 Sandler
2010/0196892 A1 8/2010 Quake et al.
2010/0203538 A1 8/2010 Dube et al.
2010/0216145 A1 8/2010 Duvdevani

(56) References Cited

U.S. PATENT DOCUMENTS

2010/0216151 A1 8/2010 Lapdus et al.
2010/0216153 A1 8/2010 Lapidus et al.
2010/0248231 A1 9/2010 Wei et al.
2010/0255492 A1 10/2010 Quake et al.
2010/0256013 A1 10/2010 Quake et al.
2010/0273159 A1 10/2010 Melo
2010/0273219 A1 10/2010 May et al.
2010/0273678 A1 10/2010 Alexandre et al.
2010/0285478 A1 11/2010 Chen et al.
2010/0285537 A1 11/2010 Zimmermann
2010/0291572 A1 11/2010 Stoughton et al.
2010/0291635 A1 11/2010 Peleg
2010/0323352 A1 12/2010 Lo et al.
2010/0326218 A1 12/2010 Boeckh et al.
2011/0015096 A1 1/2011 Chiu
2011/0033862 A1 2/2011 Rabinowitz et al.
2011/0039724 A1 2/2011 Lo et al.
2011/0045462 A1 2/2011 Fu et al.
2011/0064824 A1 3/2011 Lascoste et al.
2011/0071031 A1 3/2011 Khripin et al.
2011/0086769 A1 4/2011 Oliphant et al.
2011/0092763 A1 4/2011 Rabinowitz et al.
2011/0105353 A1 5/2011 Lo et al.
2011/0110931 A1 5/2011 Matsui
2011/0111410 A1 5/2011 Ryan et al.
2011/0130558 A1 6/2011 Ritt et al.
2011/0151442 A1 6/2011 Fan et al.
2011/0159499 A1 6/2011 Hindson et al.
2011/0160078 A1 6/2011 Fodor et al.
2011/0178719 A1 7/2011 Rabinowitz et al.
2011/0189677 A1 8/2011 Adli et al.
2011/0201507 A1 8/2011 Rava et al.
2011/0212446 A1 9/2011 Wang et al.
2011/0212846 A1 9/2011 Spier
2011/0224087 A1 9/2011 Quake et al.
2011/0246083 A1 10/2011 Fan et al.
2011/0251149 A1 10/2011 Perrine et al.
2011/0288780 A1 11/2011 Rabinowitz et al.
2011/0294699 A1 12/2011 Lee et al.
2011/0300608 A1 12/2011 Ryan et al.
2011/0301854 A1 12/2011 Curry et al.
2011/0312503 A1 12/2011 Chuu et al.
2012/0003635 A1 1/2012 Lo et al.
2012/0003637 A1 1/2012 Lo et al.
2012/0010085 A1 1/2012 Rava et al.
2012/0021442 A1 1/2012 Buhimschi et al.
2012/0028814 A1 2/2012 Toloue et al.
2012/0034603 A1 2/2012 Oliphant et al.
2012/0034685 A1 2/2012 Sparks et al.
2012/0108460 A1 5/2012 Quake et al.
2012/0115140 A1 5/2012 Rivkees et al.
2012/0122701 A1 5/2012 Ryan et al.
2012/0122702 A1 5/2012 Leproust et al.
2012/0135872 A1 5/2012 Chuu et al.
2012/0165203 A1 6/2012 Quake et al.
2012/0185176 A1 7/2012 Rabinowitz et al.
2012/0190020 A1 7/2012 Oliphant et al.
2012/0190021 A1 7/2012 Oliphant et al.
2012/0190557 A1 7/2012 Oliphant et al.
2012/0191358 A1 7/2012 Oliphant et al.
2012/0196754 A1 8/2012 Quake et al.
2012/0208706 A1 8/2012 Downing et al.
2012/0214678 A1 8/2012 Rava et al.
2012/0251411 A1 10/2012 Jeon
2012/0264121 A1 10/2012 Rava et al.
2012/0264618 A1 10/2012 Nygren
2012/0270212 A1 10/2012 Rabinowitz et al.
2012/0270739 A1 10/2012 Rava et al.
2012/0295810 A1 11/2012 Quake et al.
2012/0295819 A1 11/2012 Leamon et al.
2013/0017549 A1 1/2013 Hong
2013/0022973 A1 1/2013 Hansen et al.
2013/0024127 A1 1/2013 Stuelpnagel
2013/0034546 A1 2/2013 Rava et al.
2013/0040375 A1 2/2013 Sparks et al.
2013/0059733 A1 3/2013 Lo et al.
2013/0060483 A1 3/2013 Struble et al.
2013/0069869 A1 3/2013 Akao et al.
2013/0071844 A1 3/2013 Makino et al.
2013/0073214 A1 3/2013 Hyland et al.
2013/0085681 A1 4/2013 Deciu et al.
2013/0090250 A1 4/2013 Sparks et al.
2013/0116130 A1 5/2013 Fu et al.
2013/0123120 A1 5/2013 Zimmermann et al.
2013/0130923 A1 5/2013 Ehrich et al.
2013/0143219 A1 6/2013 Mitchell et al.
2013/0150253 A1 6/2013 Deciu et al.
2013/0157870 A1 6/2013 Pushkarev et al.
2013/0172211 A1 7/2013 Oliphant et al.
2013/0178373 A1 7/2013 Rabinowitz et al.
2013/0190653 A1 7/2013 Alvarez Ramos
2013/0196862 A1 8/2013 Rabinowitz et al.
2013/0210644 A1 8/2013 Stoughton et al.
2013/0225422 A1 8/2013 Rabinowitz et al.
2013/0231252 A1 9/2013 Mitchell et al.
2013/0237431 A1 9/2013 Lo et al.
2013/0252824 A1 9/2013 Rabinowitz
2013/0253369 A1 9/2013 Rabinowitz et al.
2013/0261004 A1 10/2013 Ryan et al.
2013/0274116 A1 10/2013 Rabinowitz et al.
2013/0274135 A1 10/2013 Zhang et al.
2013/0288252 A1 10/2013 Sparks et al.
2013/0303461 A1 11/2013 Iafrate et al.
2013/0310260 A1 11/2013 Kim et al.
2013/0323727 A1 12/2013 Huang et al.
2013/0323731 A1 12/2013 Lo et al.
2013/0325360 A1 12/2013 Deciu et al.
2013/0344066 A1 12/2013 Faham et al.
2014/0032128 A1 1/2014 Rabinowitz et al.
2014/0038830 A1 2/2014 Srinivasan et al.
2014/0045181 A1 2/2014 Lo et al.
2014/0051585 A1 2/2014 Prosen et al.
2014/0065621 A1 3/2014 Mhatre et al.
2014/0066317 A1 3/2014 Talasaz
2014/0087385 A1 3/2014 Rabinowitz et al.
2014/0094373 A1 4/2014 Zimmermann et al.
2014/0100121 A1 4/2014 Lo et al.
2014/0100126 A1 4/2014 Rabinowitz
2014/0100134 A1 4/2014 Rabinowitz et al.
2014/0106975 A1 4/2014 Stoughton et al.
2014/0113795 A1 4/2014 Emerson et al.
2014/0141981 A1 5/2014 Zimmermann et al.
2014/0154682 A1 6/2014 Rabinowitz et al.
2014/0155274 A1 6/2014 Xie et al.
2014/0162269 A1 6/2014 Rabinowitz
2014/0186827 A1 7/2014 Pieprzyk et al.
2014/0193816 A1 7/2014 Rabinowitz et al.
2014/0206552 A1 7/2014 Rabinowitz et al.
2014/0227691 A1 8/2014 May et al.
2014/0227705 A1 8/2014 Vogelstein et al.
2014/0242588 A1 8/2014 Van Den Boom et al.
2014/0256558 A1 9/2014 Varley et al.
2014/0256569 A1 9/2014 Rabinowitz et al.
2014/0272956 A1 9/2014 Huang et al.
2014/0274740 A1 9/2014 Srinivasan et al.
2014/0287934 A1 9/2014 Szelinger et al.
2014/0296081 A1 10/2014 Diehn et al.
2014/0329245 A1 11/2014 Spier et al.
2014/0336060 A1 11/2014 Rabinowitz
2015/0051087 A1 2/2015 Rabinowitz et al.
2015/0056617 A1 2/2015 Whitt et al.
2015/0064695 A1 3/2015 Katz et al.
2015/0086477 A1 3/2015 Mitchell et al.
2015/0087535 A1 3/2015 Patel
2015/0099673 A1 4/2015 Fodor
2015/0147815 A1 5/2015 Babiarz et al.
2015/0157606 A1 6/2015 Maneval et al.
2015/0167069 A1 6/2015 Schutz et al.
2015/0167077 A1 6/2015 Fehr et al.
2015/0197786 A1 7/2015 Osborne et al.
2015/0211050 A1 7/2015 Iafrate et al.
2015/0218631 A1 8/2015 Chuu et al.
2015/0232938 A1 8/2015 Mhatre
2015/0246103 A1 9/2015 Hazout

(56) References Cited

U.S. PATENT DOCUMENTS

| | | | |
|---|---|---|---|
| 2015/0265995 | A1 | 9/2015 | Head et al. |
| 2015/0299812 | A1 | 10/2015 | Talasaz |
| 2015/0315657 | A1 | 11/2015 | Rhodes et al. |
| 2015/0322507 | A1 | 11/2015 | Zimmermann et al. |
| 2015/0329891 | A1 | 11/2015 | Tan et al. |
| 2016/0024581 | A1 | 1/2016 | Sarwal et al. |
| 2016/0032396 | A1 | 2/2016 | Diehn et al. |
| 2016/0046986 | A1 | 2/2016 | Eltoukhy et al. |
| 2016/0053320 | A1 | 2/2016 | Schuh et al. |
| 2016/0115541 | A1 | 4/2016 | Schutz et al. |
| 2016/0138106 | A1 | 5/2016 | Schulze |
| 2016/0138112 | A1 | 5/2016 | Janne et al. |
| 2016/0145682 | A1 | 5/2016 | Woodward et al. |
| 2016/0186239 | A1 | 6/2016 | Sinha |
| 2016/0186253 | A1 | 6/2016 | Talasaz et al. |
| 2016/0201124 | A1 | 7/2016 | Donahue et al. |
| 2016/0239602 | A1 | 8/2016 | Shendure et al. |
| 2016/0244838 | A1 | 8/2016 | Babiarz et al. |
| 2016/0257993 | A1 | 9/2016 | Fu et al. |
| 2016/0265042 | A1 | 9/2016 | Schroeder et al. |
| 2016/0289740 | A1 | 10/2016 | Fu et al. |
| 2016/0289753 | A1 | 10/2016 | Osborne et al. |
| 2016/0312276 | A1 | 10/2016 | Fu et al. |
| 2016/0319345 | A1 | 11/2016 | Gnerre et al. |
| 2016/0369333 | A1 | 12/2016 | Babiarz et al. |
| 2017/0011166 | A1 | 1/2017 | Rabinowitz et al. |
| 2017/0107576 | A1 | 4/2017 | Babiarz et al. |
| 2017/0114411 | A1 | 4/2017 | Mitchell |
| 2017/0121716 | A1 | 5/2017 | Rodi et al. |
| 2017/0137882 | A1 | 5/2017 | Goossens et al. |
| 2017/0145475 | A1 | 5/2017 | Hunsley et al. |
| 2017/0152561 | A1 | 6/2017 | Hamamah et al. |
| 2017/0218458 | A1 | 8/2017 | Fan et al. |
| 2017/0275689 | A1 | 9/2017 | Maguire et al. |
| 2017/0283788 | A1 | 10/2017 | Khoja et al. |
| 2017/0298427 | A1 | 10/2017 | Buis et al. |
| 2017/0314014 | A1 | 11/2017 | Green et al. |
| 2017/0342477 | A1 | 11/2017 | Jensen et al. |
| 2017/0362649 | A1 | 12/2017 | Lieberman-Aiden et al. |
| 2018/0023128 | A1 | 1/2018 | Yanai et al. |
| 2018/0025109 | A1 | 1/2018 | Rabinowitz et al. |
| 2018/0105807 | A1 | 4/2018 | Lo et al. |
| 2018/0127744 | A1 | 5/2018 | Hu et al. |
| 2018/0142296 | A1 | 5/2018 | Mitchell et al. |
| 2018/0148777 | A1 | 5/2018 | Kirkizlar et al. |
| 2018/0155775 | A1 | 6/2018 | Zimmermann et al. |
| 2018/0155776 | A1 | 6/2018 | Zimmermann et al. |
| 2018/0155779 | A1 | 6/2018 | Zimmermann et al. |
| 2018/0155785 | A1 | 6/2018 | Rabinowitz et al. |
| 2018/0155786 | A1 | 6/2018 | Rabinowitz et al. |
| 2018/0155792 | A1 | 6/2018 | Rabinowitz et al. |
| 2018/0171409 | A1 | 6/2018 | Rabinowitz et al. |
| 2018/0171420 | A1 | 6/2018 | Babiarz et al. |
| 2018/0173845 | A1 | 6/2018 | Sigurjonsson et al. |
| 2018/0173846 | A1 | 6/2018 | Sigurjonsson et al. |
| 2018/0187241 | A1 | 7/2018 | Selvaraj et al. |
| 2018/0201995 | A1 | 7/2018 | Rabinowitz et al. |
| 2018/0237841 | A1 | 8/2018 | Stray et al. |
| 2018/0251553 | A1 | 9/2018 | Mcgranahan et al. |
| 2018/0265917 | A1 | 9/2018 | Barany et al. |
| 2018/0288982 | A1 | 10/2018 | Sinha |
| 2018/0298439 | A1 | 10/2018 | Ryan et al. |
| 2018/0300448 | A1 | 10/2018 | Rabinowitz et al. |
| 2018/0303870 | A1 | 10/2018 | Golobish et al. |
| 2018/0320171 | A1 | 11/2018 | Withey |
| 2018/0320239 | A1 | 11/2018 | Babiarz et al. |
| 2018/0371531 | A1 | 12/2018 | Quake et al. |
| 2019/0010543 | A1 | 1/2019 | Babiarz et al. |
| 2019/0106737 | A1 | 4/2019 | Underhill |
| 2019/0106751 | A1 | 4/2019 | Zimmermann et al. |
| 2019/0112661 | A1 | 4/2019 | Khan et al. |
| 2019/0153521 | A1 | 5/2019 | Mitchell et al. |
| 2019/0153525 | A1 | 5/2019 | Mitchell et al. |
| 2019/0185913 | A1 | 6/2019 | Zimmermann et al. |
| 2019/0185936 | A1 | 6/2019 | Babiarz et al. |
| 2019/0194743 | A1 | 6/2019 | Ryan et al. |
| 2019/0194758 | A1 | 6/2019 | Babiarz et al. |
| 2019/0194759 | A1 | 6/2019 | Babiarz et al. |
| 2019/0203290 | A1 | 7/2019 | Rabinowitz et al. |
| 2019/0203294 | A1 | 7/2019 | Babiarz et al. |
| 2019/0211376 | A1 | 7/2019 | Quake et al. |
| 2019/0211385 | A1 | 7/2019 | Sarwar et al. |
| 2019/0211391 | A1 | 7/2019 | Rabinowitz et al. |
| 2019/0211392 | A1 | 7/2019 | Rabinowitz et al. |
| 2019/0211393 | A1 | 7/2019 | Rabinowitz et al. |
| 2019/0211399 | A1 | 7/2019 | Rabinowitz et al. |
| 2019/0211402 | A1 | 7/2019 | Babiarz et al. |
| 2019/0211406 | A1 | 7/2019 | Babiarz et al. |
| 2019/0249241 | A1 | 8/2019 | Rabinowitz et al. |
| 2019/0256894 | A1 | 8/2019 | Zimmermann et al. |
| 2019/0256906 | A1 | 8/2019 | Rabinowitz et al. |
| 2019/0256907 | A1 | 8/2019 | Ryan et al. |
| 2019/0256908 | A1 | 8/2019 | Rabinowitz et al. |
| 2019/0256909 | A1 | 8/2019 | Rabinowitz et al. |
| 2019/0256912 | A1 | 8/2019 | Rabinowitz et al. |
| 2019/0256916 | A1 | 8/2019 | Babiarz et al. |
| 2019/0256917 | A1 | 8/2019 | Babiarz et al. |
| 2019/0256919 | A1 | 8/2019 | Babiarz et al. |
| 2019/0256924 | A1 | 8/2019 | Vogelstein et al. |
| 2019/0256931 | A1 | 8/2019 | Babiarz et al. |
| 2019/0264277 | A1 | 8/2019 | Rabinowitz et al. |
| 2019/0264280 | A1 | 8/2019 | Rabinowitz et al. |
| 2019/0264288 | A1 | 8/2019 | Rabinowitz et al. |
| 2019/0271043 | A1 | 9/2019 | Babiarz et al. |
| 2019/0276888 | A1 | 9/2019 | Rabinowitz et al. |
| 2019/0284623 | A1 | 9/2019 | Rabinowitz et al. |
| 2019/0300950 | A1 | 10/2019 | Rabinowitz et al. |
| 2019/0309358 | A1 | 10/2019 | Rabinowitz et al. |
| 2019/0309359 | A1 | 10/2019 | Zimmermann et al. |
| 2019/0309365 | A1 | 10/2019 | Babiarz et al. |
| 2019/0316177 | A1 | 10/2019 | Zimmermann et al. |
| 2019/0316184 | A1 | 10/2019 | Zimmermann et al. |
| 2019/0316200 | A1 | 10/2019 | Rabinowitz et al. |
| 2019/0323076 | A1 | 10/2019 | Rabinowitz et al. |
| 2019/0360033 | A1 | 11/2019 | Stamm et al. |
| 2019/0360036 | A1 | 11/2019 | Rabinowitz et al. |
| 2019/0367972 | A1 | 12/2019 | Mitchell et al. |
| 2020/0024653 | A1 | 1/2020 | Bethke |
| 2020/0032323 | A1 | 1/2020 | Talasaz et al. |
| 2020/0032340 | A1 | 1/2020 | Mitchell et al. |
| 2020/0109449 | A1 | 4/2020 | Stamm et al. |
| 2020/0121718 | A1 | 4/2020 | Novik et al. |
| 2020/0123612 | A1 | 4/2020 | Babiarz et al. |
| 2020/0126634 | A1 | 4/2020 | Sigurjonsson et al. |
| 2020/0140950 | A1 | 5/2020 | Babiarz et al. |
| 2020/0141925 | A1 | 5/2020 | Liaw et al. |
| 2020/0149111 | A1 | 5/2020 | Babiarz et al. |
| 2020/0157629 | A1 | 5/2020 | Babiarz et al. |
| 2020/0165678 | A1 | 5/2020 | Mitchell et al. |
| 2020/0172977 | A1 | 6/2020 | Rabinowitz et al. |
| 2020/0181681 | A1 | 6/2020 | Mitchell et al. |
| 2020/0181697 | A1 | 6/2020 | Rabinowitz et al. |
| 2020/0190570 | A1 | 6/2020 | Ryan et al. |
| 2020/0190573 | A1 | 6/2020 | Rabinowitz et al. |
| 2020/0190591 | A1 | 6/2020 | Rabinowitz et al. |
| 2020/0208196 | A1 | 7/2020 | Zimmermann et al. |
| 2020/0208221 | A1 | 7/2020 | Babiarz et al. |
| 2020/0224273 | A1 | 7/2020 | Rabinowitz et al. |
| 2020/0232036 | A1 | 7/2020 | Rabinowitz et al. |
| 2020/0232037 | A1 | 7/2020 | Babiarz et al. |
| 2020/0248264 | A1 | 8/2020 | Rabinowitz et al. |
| 2020/0248266 | A1 | 8/2020 | Swanton et al. |
| 2020/0316498 | A1 | 10/2020 | Mitchell |
| 2020/0318191 | A1 | 10/2020 | Babiarz et al. |
| 2020/0347454 | A1 | 11/2020 | Babiarz et al. |
| 2020/0350034 | A1 | 11/2020 | Rabinowitz et al. |
| 2020/0362415 | A1 | 11/2020 | Rabinowitz et al. |
| 2020/0370129 | A1 | 11/2020 | Quinn et al. |
| 2020/0385809 | A1 | 12/2020 | Ramani et al. |
| 2020/0407788 | A1 | 12/2020 | Ryan et al. |
| 2020/0407798 | A1 | 12/2020 | Babiarz et al. |
| 2021/0009990 | A1 | 1/2021 | Stray et al. |
| 2021/0025005 | A1 | 1/2021 | Babiarz et al. |
| 2021/0032692 | A1 | 2/2021 | Mitchell et al. |

(56) References Cited

U.S. PATENT DOCUMENTS

| | | | |
|---|---|---|---|
| 2021/0054459 | A1 | 2/2021 | Rabinowitz et al. |
| 2021/0071246 | A1 | 3/2021 | Zimmermann et al. |
| 2021/0139969 | A1 | 5/2021 | Mitchell et al. |
| 2021/0139983 | A1 | 5/2021 | Mitchell et al. |
| 2021/0139988 | A1 | 5/2021 | Mitchell et al. |
| 2021/0155988 | A1 | 5/2021 | Rabinowitz et al. |
| 2021/0189498 | A1 | 6/2021 | Babiarz et al. |
| 2021/0198733 | A1 | 7/2021 | Moshkevich et al. |
| 2021/0198742 | A1 | 7/2021 | Rabinowitz et al. |
| 2021/0198743 | A1 | 7/2021 | Rabinowitz et al. |
| 2021/0222230 | A1 | 7/2021 | Zimmermann et al. |
| 2021/0222240 | A1 | 7/2021 | Moshkevich et al. |
| 2021/0257048 | A1 | 8/2021 | Zimmermann et al. |
| 2021/0269879 | A1 | 9/2021 | Mitchell et al. |
| 2021/0301320 | A1 | 9/2021 | Mitchell et al. |
| 2021/0324463 | A1 | 10/2021 | Rabinowitz et al. |
| 2021/0327538 | A1 | 10/2021 | Egilsson et al. |
| 2021/0327542 | A1 | 10/2021 | Ryan et al. |
| 2021/0348229 | A1 | 11/2021 | Maguire et al. |
| 2021/0355536 | A1 | 11/2021 | Rabinowitz et al. |
| 2022/0025455 | A1 | 1/2022 | Zimmermann et al. |
| 2022/0025456 | A1 | 1/2022 | Rabinowitz et al. |
| 2022/0033908 | A1 | 2/2022 | Rabinowitz et al. |
| 2022/0033909 | A1 | 2/2022 | Babiarz et al. |
| 2022/0042103 | A1 | 2/2022 | Rabinowitz et al. |
| 2022/0056509 | A1 | 2/2022 | Zimmermann |
| 2022/0056534 | A1 | 2/2022 | Rivers |
| 2022/0073978 | A1 | 3/2022 | Rabinowitz et al. |
| 2022/0073979 | A1 | 3/2022 | Rabinowitz et al. |
| 2022/0098667 | A1 | 3/2022 | Rabinowitz et al. |
| 2022/0139495 | A1 | 5/2022 | Rabinowitz et al. |
| 2022/0145391 | A1 | 5/2022 | Mitchell et al. |
| 2022/0154249 | A1 | 5/2022 | Zimmermann et al. |
| 2022/0154290 | A1 | 5/2022 | Babiarz et al. |
| 2022/0195526 | A1 | 6/2022 | Rabinowitz et al. |
| 2022/0213561 | A1 | 7/2022 | Babiarz et al. |
| 2022/0251654 | A1 | 8/2022 | Hafez et al. |
| 2022/0267849 | A1 | 8/2022 | Mitchell et al. |
| 2022/0282335 | A1 | 9/2022 | Babiarz et al. |
| 2022/0307086 | A1 | 9/2022 | Babiarz et al. |
| 2022/0340963 | A1 | 10/2022 | North et al. |
| 2022/0356522 | A1 | 11/2022 | Mitchell et al. |
| 2022/0356526 | A1 | 11/2022 | Babiarz et al. |
| 2022/0356530 | A1 | 11/2022 | Sharma |
| 2022/0403461 | A1 | 12/2022 | Kirkizlar et al. |
| 2022/0411875 | A1 | 12/2022 | Rabinowitz et al. |
| 2023/0053752 | A1 | 2/2023 | Rabinowitz et al. |
| 2023/0054494 | A1 | 2/2023 | Rabinowitz et al. |
| 2023/0060579 | A1 | 3/2023 | Bethke et al. |
| 2023/0360723 | A1 | 11/2023 | Rabinowitz et al. |
| 2023/0368865 | A1 | 11/2023 | Rabinowitz et al. |
| 2023/0383348 | A1 | 11/2023 | Rabinowitz et al. |
| 2023/0420071 | A1 | 12/2023 | Rabinowitz et al. |
| 2024/0002938 | A1 | 1/2024 | Rabinowitz et al. |
| 2024/0038328 | A1 | 2/2024 | Rabinowitz et al. |
| 2024/0060124 | A1 | 2/2024 | Ryan et al. |
| 2024/0062846 | A1 | 2/2024 | Rabinowitz |
| 2024/0068031 | A1 | 2/2024 | Rabinowitz |
| 2024/0132957 | A1 | 4/2024 | Mitchell et al. |
| 2024/0132960 | A1 | 4/2024 | Demko |
| 2024/0158855 | A1 | 5/2024 | Babiarz et al. |
| 2024/0185957 | A1 | 6/2024 | Rabinowitz et al. |
| 2024/0271214 | A1 | 8/2024 | Rabinowitz et al. |

FOREIGN PATENT DOCUMENTS

| | | | |
|---|---|---|---|
| CN | 1650032 | A | 8/2005 |
| CN | 1674028 | A | 9/2005 |
| CN | 101675169 | A | 3/2010 |
| CN | 102892901 | A | 1/2013 |
| CN | 104736722 | A | 6/2015 |
| CN | 105229175 | A | 1/2016 |
| CN | 107365769 | A | 11/2017 |
| CN | 107849604 | A | 3/2018 |
| CN | 109661476 | A | 4/2019 |
| CN | 116287197 | A | 6/2023 |
| EA | 201792389 | A1 | 5/2018 |
| EP | 0270017 | A2 | 6/1988 |
| EP | 1325963 | A1 | 7/2003 |
| EP | 1524321 | A1 | 4/2005 |
| EP | 1325963 | B1 | 9/2006 |
| EP | 1524321 | B1 | 7/2009 |
| EP | 2163622 | A1 | 3/2010 |
| EP | 2128169 | A1 | 12/2010 |
| EP | 2551356 | A1 | 1/2013 |
| EP | 2653562 | A1 | 10/2013 |
| EP | 2902500 | A1 | 8/2015 |
| EP | 3026124 | A1 | 6/2016 |
| EP | 2315849 | B1 | 11/2017 |
| EP | 3285193 | A1 | 2/2018 |
| EP | 2877594 | B1 | 12/2019 |
| EP | 3187597 | B1 | 6/2020 |
| EP | 3134541 | B1 | 8/2020 |
| EP | 3760730 | A1 | 1/2021 |
| EP | 3760731 | A1 | 1/2021 |
| EP | 3760732 | A1 | 1/2021 |
| EP | 3824470 | | 5/2021 |
| EP | 3443119 | B1 | 2/2022 |
| GB | 2488358 | | 8/2012 |
| JP | 2965699 | | 8/1999 |
| JP | 2002-530121 | A | 9/2002 |
| JP | 2002-300894 | A | 10/2002 |
| JP | 2003/521252 | A | 7/2003 |
| JP | 2004502466 | A | 1/2004 |
| JP | 2004121087 | A | 4/2004 |
| JP | 2004533243 | A | 11/2004 |
| JP | 2005514956 | A | 5/2005 |
| JP | 2005160470 | A | 6/2005 |
| JP | 2006-254912 | A | 9/2006 |
| JP | 2008-263974 | A | 11/2008 |
| JP | 2008/271980 | A | 11/2008 |
| JP | 2010-509922 | A | 4/2010 |
| JP | 2011/508662 | A | 3/2011 |
| JP | 2011/516069 | A | 5/2011 |
| JP | 2012085556 | A | 5/2012 |
| JP | 2013509883 | A | 3/2013 |
| JP | 2014118334 | A1 | 8/2014 |
| JP | 2015-535681 | | 12/2015 |
| JP | 2016502849 | A | 2/2016 |
| RU | 2290078 | C1 | 12/2006 |
| WO | 95/01796 | | 1/1995 |
| WO | WO9623067 | A1 | 8/1996 |
| WO | 1996036736 | A2 | 11/1996 |
| WO | 98/39474 | | 9/1998 |
| WO | 98/44151 | | 10/1998 |
| WO | WO9937773 | A1 | 7/1999 |
| WO | 00/18957 | | 4/2000 |
| WO | 2001007640 | A2 | 2/2001 |
| WO | 0134844 | A1 | 5/2001 |
| WO | 01/57269 | A2 | 8/2001 |
| WO | 2001/079851 | A1 | 10/2001 |
| WO | 200190419 | A2 | 11/2001 |
| WO | 2002004672 | A2 | 1/2002 |
| WO | 02/44411 | A1 | 6/2002 |
| WO | 2002055985 | A2 | 7/2002 |
| WO | 02/070751 | A1 | 9/2002 |
| WO | 2002076377 | | 10/2002 |
| WO | 02/090505 | A2 | 11/2002 |
| WO | 03/000919 | A2 | 1/2003 |
| WO | 03/018757 | A3 | 3/2003 |
| WO | 03/020974 | A3 | 3/2003 |
| WO | 2003031646 | A1 | 4/2003 |
| WO | 2003/050532 | A1 | 6/2003 |
| WO | 2003062441 | A1 | 7/2003 |
| WO | 2003/102595 | A1 | 12/2003 |
| WO | 2003/106623 | A2 | 12/2003 |
| WO | 2004/051218 | A2 | 6/2004 |
| WO | 2004069849 | A2 | 8/2004 |
| WO | 2004070005 | A2 | 8/2004 |
| WO | 2004070007 | A2 | 8/2004 |
| WO | 2004081183 | | 9/2004 |
| WO | WO2004078999 | A1 | 9/2004 |
| WO | 2004087863 | A2 | 10/2004 |
| WO | 2005003375 | A2 | 1/2005 |

(56) References Cited

FOREIGN PATENT DOCUMENTS

WO 2005021793 A1 3/2005
WO 2005023091 A2 3/2005
WO 2005030999 A1 4/2005
WO 2005035725 A2 4/2005
WO 2005/039389 A3 5/2005
WO 2005100401 A2 10/2005
WO 2005123779 A2 12/2005
WO 2007145612 A1 6/2006
WO 2006110855 A2 10/2006
WO 2006/128192 A2 11/2006
WO 2007/011903 A3 1/2007
WO 2007/052006 A1 5/2007
WO 2007057647 A1 5/2007
WO 2007062164 A3 5/2007
WO 2007/073171 A2 6/2007
WO 2007070280 A2 6/2007
WO 2007070482 A2 6/2007
WO 2007075836 A2 7/2007
WO 2007/092473 A2 8/2007
WO 2007086935 A2 8/2007
WO 2007/117256 A1 10/2007
WO 2007117039 A1 10/2007
WO 2007132167 A2 11/2007
WO 2007/147073 A2 12/2007
WO 2007/147076 A2 12/2007
WO 2007140417 A2 12/2007
WO 2007147074 A2 12/2007
WO 2007147079 A2 12/2007
WO 2008024473 A2 2/2008
WO 2008048931 A1 4/2008
WO 2008/061213 A2 5/2008
WO 2008051928 A2 5/2008
WO 2008056937 A1 5/2008
WO 2008059578 A1 5/2008
WO 2008079374 A2 7/2008
WO 2008081451 A2 7/2008
WO 2008084405 A2 7/2008
WO 2008115427 A2 9/2008
WO 2008115497 A2 9/2008
WO 2008118988 A1 10/2008
WO 2008135837 A2 11/2008
WO 2008157264 A2 12/2008
WO 2009009769 A2 1/2009
WO 2009013492 A1 1/2009
WO 2009013496 A1 1/2009
WO 2009019215 A1 2/2009
WO 2009019455 A2 2/2009
WO 2009/032779 A2 3/2009
WO 2009/036525 A2 3/2009
WO 2009030100 A1 3/2009
WO 2009032781 A2 3/2009
WO 2009033178 A1 3/2009
WO 2009049889 A1 4/2009
WO 2009017784 A2 5/2009
WO 2009064897 A2 5/2009
WO 2009091934 A1 7/2009
WO 2009092035 A2 7/2009
WO 2009/105531 A1 8/2009
WO 2009099602 A1 8/2009
WO 2009100029 A1 8/2009
WO 2009117122 A2 9/2009
WO 2009120808 A2 10/2009
WO 2009145828 A2 12/2009
WO 2009146335 A1 12/2009
WO 2010014920 A1 2/2010
WO 2010017214 A1 2/2010
WO 2010/033639 A2 3/2010
WO 2010/033652 A1 3/2010
WO 2010033578 A2 3/2010
WO 2010042831 A2 4/2010
WO 2010045617 A2 4/2010
WO 2010075459 7/2010
WO 2010/088288 A2 8/2010
WO 2010115016 A2 10/2010
WO 2010115154 A1 10/2010
WO 2010118016 A2 10/2010
WO 2010/127186 A1 11/2010
WO WO2011015944 A2 2/2011
WO 2011/023078 A1 3/2011
WO 2011/032078 A1 3/2011
WO 2011041485 A1 4/2011
WO 2011/051283 A1 5/2011
WO 2011057094 5/2011
WO WO2011057061 A1 5/2011
WO 2011/090556 A1 7/2011
WO 2011087760 7/2011
WO 2011102998 A2 8/2011
WO WO2011094646 A1 8/2011
WO 2011/118603 9/2011
WO 2011109440 A1 9/2011
WO WO2011118603 A1 9/2011
WO 2011/142836 A2 11/2011
WO 2011140433 A2 11/2011
WO 2011146632 A1 11/2011
WO 2012/019200 A2 2/2012
WO 2012/028746 A1 3/2012
WO 2012042374 A2 4/2012
WO 2012/058488 A1 5/2012
WO 2012-083189 A2 6/2012
WO 201283250 6/2012
WO 2012088456 A2 6/2012
WO 20120071621 6/2012
WO 2012092426 7/2012
WO 2012108920 A1 8/2012
WO WO2012122374 A2 9/2012
WO 2012/142531 A2 10/2012
WO 2007/149791 A2 12/2012
WO 2013030577 3/2013
WO 2013/045432 A1 4/2013
WO 2013/049892 A1 4/2013
WO 2013052557 A2 4/2013
WO 2013/078470 A2 5/2013
WO 2013/086464 A1 6/2013
WO 2013/123220 A1 8/2013
WO 2013/138510 A1 9/2013
WO 2013/138510 A9 9/2013
WO 20130130848 9/2013
WO WO2013159035 A2 10/2013
WO 2013/169339 A1 11/2013
WO 2013/177220 A1 11/2013
WO 2013/181651 A1 12/2013
WO 2013190441 A2 12/2013
WO 2014/004726 A1 1/2014
WO 2014/014497 A1 1/2014
WO 20140018080 1/2014
WO 2014026277 A1 2/2014
WO 2014/035986 A1 3/2014
WO 2014039556 A1 3/2014
WO WO2014099919 A2 6/2014
WO 2014/122288 A1 8/2014
WO 2014/1424290 A1 8/2014
WO 2014/145078 A1 9/2014
WO 2014/145232 A2 9/2014
WO 2014/149134 A2 9/2014
WO 2014/150300 A2 9/2014
WO 2014/151117 A1 9/2014
WO WO2014143989 A1 9/2014
WO WO2014194113 A2 12/2014
WO 2015/006668 A1 1/2015
WO 2015035177 A1 3/2015
WO 2015134552 A1 3/2015
WO 2015/048535 A1 4/2015
WO 2015/070086 A1 5/2015
WO WO2015069933 A1 5/2015
WO 2015/100427 A1 7/2015
WO 2015138997 A1 9/2015
WO 2015/148494 A1 10/2015
WO 2015/164432 A1 10/2015
WO WO2015169947 A1 11/2015
WO WO2015178978 A2 11/2015
WO 2016/009059 A1 1/2016
WO 2016009224 A1 1/2016
WO WO2016001411 A1 1/2016
WO WO2016028316 A1 2/2016

(56) References Cited

FOREIGN PATENT DOCUMENTS

| | | | |
|---|---|---|---|
| WO | 2016/065295 | A1 | 4/2016 |
| WO | WO2016063122 | A1 | 4/2016 |
| WO | 2016/077313 | A1 | 5/2016 |
| WO | WO2016123698 | A1 | 8/2016 |
| WO | 2016/138080 | A1 | 9/2016 |
| WO | 2016/183106 | A1 | 11/2016 |
| WO | WO2016176662 | A1 | 11/2016 |
| WO | 2016/193490 | A1 | 12/2016 |
| WO | 2016192956 | A1 | 12/2016 |
| WO | WO2017011329 | A1 | 1/2017 |
| WO | 2017-045654 | A1 | 3/2017 |
| WO | 2017/058784 | A1 | 4/2017 |
| WO | WO2017091865 | A1 | 6/2017 |
| WO | 2017/176852 | A1 | 10/2017 |
| WO | 2017/181146 | A1 | 10/2017 |
| WO | 2017/181202 | A2 | 10/2017 |
| WO | 2017205540 | A1 | 11/2017 |
| WO | WO2017190106 | A1 | 11/2017 |
| WO | 2018/009723 | A1 | 1/2018 |
| WO | 2018/083467 | A1 | 5/2018 |
| WO | WO2018085597 | A1 | 5/2018 |
| WO | WO2018085603 | A1 | 5/2018 |
| WO | 2018/106798 | A1 | 6/2018 |
| WO | WO2018119422 | A1 | 6/2018 |
| WO | 2018/136562 | A2 | 7/2018 |
| WO | 2018/156418 | A1 | 8/2018 |
| WO | 2018/237081 | A1 | 12/2018 |
| WO | WO2018237078 | A1 | 12/2018 |
| WO | WO2019006561 | A1 | 1/2019 |
| WO | WO2019008408 | A1 | 1/2019 |
| WO | 2019/046817 | A1 | 3/2019 |
| WO | WO2019053243 | A1 | 3/2019 |
| WO | WO2019109053 | A1 | 6/2019 |
| WO | WO2019118926 | A1 | 6/2019 |
| WO | 2019/140298 | A1 | 7/2019 |
| WO | 2019/161244 | A1 | 8/2019 |
| WO | 2019/200228 | A1 | 10/2019 |
| WO | 2019/241349 | A1 | 12/2019 |
| WO | 2020/010255 | A1 | 1/2020 |
| WO | 2020/018522 | A1 | 1/2020 |
| WO | 2020/041449 | A1 | 2/2020 |
| WO | 2020/076957 | A1 | 4/2020 |
| WO | 2020/106987 | A1 | 5/2020 |
| WO | 2020104670 | A1 | 5/2020 |
| WO | 2020/131699 | A2 | 6/2020 |
| WO | WO2020131955 | A1 | 6/2020 |
| WO | 2020/214547 | A1 | 10/2020 |
| WO | WO2020206290 | A1 | 10/2020 |
| WO | 2020/247263 | A1 | 12/2020 |
| WO | 2021/055968 | A1 | 3/2021 |
| WO | 2007100911 | A2 | 9/2021 |
| WO | 2021/243045 | A1 | 12/2021 |
| WO | 2021/243206 | | 12/2021 |
| WO | 2022/015676 | A1 | 1/2022 |
| WO | 2022182878 | | 9/2022 |
| WO | 2022197864 | | 9/2022 |
| WO | 2023014597 | A1 | 2/2023 |
| WO | 2023034090 | A1 | 3/2023 |
| WO | 2023/244735 | A2 | 12/2023 |
| WO | 2012/024543 | A1 | 2/2024 |
| WO | 2024/076485 | A1 | 4/2024 |
| WO | 2024076469 | A1 | 4/2024 |
| WO | 2024076484 | A1 | 4/2024 |
| WO | 2024/148019 | A1 | 7/2024 |

OTHER PUBLICATIONS

"HumanOmni 1—Quad BeadChip", Illumina DNA Analysis, HumanOmni 1 array product information datasheet, 2009, 1 page.

"HumanOmni2.5-8 BeadChips", Illumina; Data Sheet: DNA Analysis, HumanOmni2.5-8 array product information datasheet, 2011, 1 page.

"Quantitative Detection of Circulating Donor-Specific DNA in Organ Transplant Recipients (DTRT-Multi-Center Study) (DTRT)", ClinicalTrials.gov Identifier: NCT02109575., Apr. 10, 2014, Last updated Mar. 26, 2021, 9 pages.

"The Journal of Heart and Lung Transplantation", Apr. 2012., vol. 31, Issue 4, Supplement, pp. A1-A4, S1-S310. https://www.google.de/search q=The+Journal+of+Heart+and+Lung+Transplantation+Volume+31,+Issue+4, +Supplement&sourceid=ie7&rls=com.microsoft:en-US:IE-Address&ie=&OE=#spf=1604593918239, Last Accessed: Oct. 13, 2015., A1-A4.

18820195.8, "Extended European Search Report", mailed Jan. 27, 2021, 9 pages.

18821381.3, "Extended European Search Report", mailed Feb. 15, 2021, 9 pages.

Abbosh, et al., "Phylogenetic ctDNA analysis depicts early-stage lung cancer evolution", Nature, 2017, 446-453.

Adamek, Martina et al., "A fast and simple method for detecting and quantifying donor-derived cell-free DNA in sera of solid organ transplant recipients as a biomarker for graft function", Clinical Chemistry and Laboratory Medicine : Journal of the Forum of the European Societies of Clinical Chemistry, vol. 54, No. 7, doi: 10.1515/CCLM-2015-0622, ISSN 1437-4331, (Jul. 1, 2016), pp. 1147-1155.

Agbor-Enoh, et al., "Applying rigor and reproducibility standards to assay donor-derived cell-free DNA as a non-invasive method for detection of acute rejection and graft injury after heart transplantation", J Heart Lung Transplant, 36(9):1004-1012. doi: 10.1016/j.healun.2017.05.026. Epub May 20, 2017, 17 pages.

Agbor-Enoh, et al., "Cell-Free DNA to Detect Heart Allograft Acute Rejection", Circulation, Mar. 23, 2021;143(12): doi: 10.1161/CIRCULATIONAHA. 120.049098. Epub Jan. 13, 2021, 1184-1197.

Ahmadian, A. et al., "Analysis of the p53 Tumor Suppressor Gene by Pyrosequencing", BioTechniques, vol. 28, Jan. 2000, 140-147.

Ahmed, et al., "Cell Free DNA and Procalcitonin as Early Markers of Complications in ICU Patients with Multiple Trauma and Major Surgery", Clin Lab, Dec. 1, 2016;62(12) ; doi: 10.7754/Clin.Lab.2016.160615., 2395-2404.

Alachkar, , "Serum and urinary biomarkers in acute kidney transplant rejection", Nephrol Ther., Feb. 2012;8(1): doi: 10.1016/j.nephro.2011.07.409. Epub Oct. 21, 2011, 13-19.

Almeida, et al., "Evaluation of 16 SNPs allele-specific to quantify post hSCT chimerism by SYBR green-based qRT-PCR", J Clin Pathol., Mar. 2013;66(3):. doi: 10.1136/jclinpath-2012-201224. Epub Jan. 2, 2013, 238-242.

Andargie, et al., "Cell-free DNA maps COVID-19 tissue injury and risk of death and can cause tissue injury", JCI Insight, Apr. 8, 2021;6(7):e147610. doi: 10.1172/jci.insight.147610, 20 pages.

Arshad, et al., "Elevated Cell-Free Mitochondrial DNA in Filtered Plasma Is Associated With HIV Infection and Inflammation", J Acquir Immune Defic Syndr., May 1, 2018;78(1): doi: 10.1097/QAI.0000000000001650., 111-118.

Avriel, et al., "Admission Cell Free DNA Levels Predict 28-Day Mortality in Patients with Severe Sepsis in Intensive Care", PLoS One., Jun. 23, 2014;9(6):e100514. doi: 10.1371/journal.pone.0100514. eCollection 2014., 7 pages.

Ayyadevara, et al., "Discrimination of primer 3'-nucleotide mismatch by taq DNA polymerase during polymerase chain reaction", Anal Biochem. Aug. 15, 2000, 284(1), 11-18.

Bai, et al., "Detection and quantification of heteroplasmic mutant mitochondrial DNA by real-time amplification refractory mutation system quantitative PCR analysis: a single-step approach", Clin Chem., Jun. 2004; 50(6); Epub Apr. 8, 2004., 996-1001.

Benesova, et al., "Mutation-based detection and monitoring of cell-free tumor DNA in peripheral blood of cancer patients", Analytical Biochemistry, vol. 433, 2013, 227-234.

Benn, Peter et al., "Current Controversies in Prenatal Diagnosis 2: NIPT results suggesting maternal cancer should always be disclosed", Prenetal Diagnosis, vol. 39, No. 5, 2018, 339-343.

Bergallo, et al., "A novel TaqMAMA assay for allelic discrimination of TLR9 rs352140 polymorphism", J Virol Methods, May 2017;243. doi: 10.1016/j.jviromet.2017.01.015. Epub Jan. 28, 2017, 25-30.

Bergallo, et al., "Evaluation of IFN-y polymorphism+874 T/A in patients with recurrent tonsillitis by PCR real time mismatch amplification mutation assay (MAMA real time PCR)", Cytokine., Feb. 2015; 71(2): Epub Dec. 2014, 278-282.

(56) References Cited

OTHER PUBLICATIONS

Bewersdorf, Jan Philipp et al., "From clonal hematopoiesis to myeloid leukemia and what happens in between: Will improved understanding lead to new therapeutic and preventive opportunities?", Blood Reviews, vol. 37, 2019, 6.
Bezieau, et al., "High incidence of N and K-Ras activating mutations in multiple myeloma and primary plasma cell leukemia at diagnosis", Hum Mutat., Sep. 2001;18(3):. doi: 10.1002/humu.1177, 212-224.
Bianchi, Diana W. et al., "Noninvasive Prenatal Testing and Incidental Detection of Occult Maternal Malignancies", Jama the Journal of the American Medical Association, vol. 314, No. 2, 2015, 162.
Bienkowski, et al., "Liquid biopsy for minimally invasive heart transplant monitoring: a pilot study", J Clin Pathol., Aug. 2020;73(8): doi: 10.1136/jclinpath-2019-205926. Epub Dec. 5, 2019, 507-510.
Birkenkamp-Demtroder, et al., "Longitudinal assessment of multiplex patient-specific ctDNA biomarkers in bladder cancer for diagnosis, surveillance and recurrence", Annals of Oncology, Oxford University Press Nld, vol. 29, No. Supplement 8, 2018, viii26.
Blomquist, et al., "Targeted RNA-Sequencing with Competitive Multiplex-PCR Amplicon Libraries", PLOS ONE, 2013, vol. 8, Issue 11.
Board, et al., "Detection of PIK3CA mutations in circulating free DNA in patients with breast cancer", Breast Cancer Res Treat, Apr. 2010;120(2): doi: 10.1007/s10549-010-0747-9. Epub Jan. 28, 2010, 461-467.
Board, et al., "Multiplexed assays for detection of mutations in PIK3CA", Clin Chem., Apr. 2008; 54(4), 757-760.
Bolotin, D. A. et al., "MiXCR: software for comprehensive adaptive immunity profiling", Nature, vol. 12, No. 5, May 2015, 380-381.
Braun, et al., "Limitation of Circulating cfDNA Under the Use of a Cytokine Elimination Adsorber (CytoSorb) in Cardiac Surgery", The Thoracic and Cardiovascular Surgeon, Jan. 2018; 66(S01): S1-S110, 1 page.
Brochet, X et al., "IMGT/V-QUEST: the highly customized and integrated system for IG and TR standardized V-J and V-D-J sequence analysis", Nucleic Acids Research, vol. 36, May 23, 2008, W503-W508.
Bronkhorst, et al., "The emerging role of cell-free DNA as a molecular marker for cancer management", Biomol Detect Quantif, Mar. 18, 2019;17:100087. doi: 10.1016/j.bdq.2019.100087., 23 pages.
Bunnapradist, S. et al., "Using both the fraction and Quantity of Donor-Derived Cell-free DNA to Detect Kidney Allograft Rejection", JASN, vol. 32, 2021, 2439-2441.
Burgstaller, et al., "Mitochondrial DNA heteroplasmy in ovine fetuses and sheep cloned by somatic cell nuclear transfer", BMC Dev Biol., Dec. 21, 2007;7:141, 10 pages.
Burnham, P. et al., "Single-stranded DNA library preparation uncovers the origin and diversity of ultrashort cell-free DNA in plasma", Scientific Reports, vol. 6, No. 27859, Jun. 14, 2016, 9 pages.
Cabel, et al., "Circulating tumor DNA changes for early monitoring of anti-PD1 immunotherapy: a proof-of-concept study", Ann Oncol., Aug. 1, 2017;28(8); doi: 10.1093/annonc/mdx212., 1996-2001.
Cagliani, et al., "Deoxyribonuclease Reduces Tissue Injury and Improves Survival After Hemorrhagic Shock", J Surg Res., May 2020;249: doi: 10.1016/j.jss.2019.11.036. Epub Jan. 8, 2020., 104-113.
Castells, et al., "K-ras mutations in DNA extracted from the plasma of patients with pancreatic carcinoma: diagnostic utility and prognostic significance", J Clin Oncol., Feb. 1999;17(2): doi: 10.1200/JCO.1999.17.2.578., 578-584.
Castleberry, et al., "Quantification of Circulating Cell-Free DNA in Pediatric Heart Transplant Recipients", Journal of Heart and Lung Transplantation, Apr. 1, 2011; 30(4): ISSN: 1053-2498, DOI: 10.1016/j.healun.2011.01.415, S139.
Cawkwell, L. et al., "Rapid detection of allele loss in colorectal tumours using microsatellites and fluorescent DNA technology", Br. J. Cancer, vol. 67, 1993, 1262-1267.
Chan, et al., "Bioinformatics analysis of circulating cell-free DNA sequencing data", Clin Biochem., Oct. 2015;48(15); doi: 10.1016/j.clinbiochem.2015.04.022. Epub May 9, 2015, 962-975.
Chang, et al., "Identification of individual DNA molecule of Mycobacterium tuberculosis by nested PCR-RLFP and capillary electrophoresis", National Library of Medicine, 2008, 182-8.
Chen, et al., "Non-invasive prenatal diagnosis using fetal DNA in maternal plasma: a preliminary study for identification of paternally-inherited alleles using single nucleotide polymorphisms", BMJ Open, Jul. 22, 2015;5(7):e007648. doi: 10.1136/bmjopen-2015-007648., 8 pages.
Chen, et al., "Non-invasive prenatal diagnosis using fetal DNA in maternal plasma: a preliminary study for identification of paternally-inherited alleles using single nucleotide polymorphisms", BMJ Open, 5(7), 2015, 1-8.
Chen, Ke et al., "Multiplex PCR with the Blunt Hairpin Primers for Next Generation Sequencing", Biotechnology and Bioprocess Engineering, vol. 22, 2017, 347-351.
Cheng, et al., "Cell-Free DNA in Blood Reveals Significant Cell, Tissue and Organ Specific injury and Predicts COVID-19 Severity", medRxiv., Jul. 29, 2020;2020.07.27.20163188. doi: 10.1101/2020.07.27.20163188., 16 pages.
Chiu, et al., "Effects of blood-processing protocols on fetal and total DNA quantification in maternal plasma", Clin Chem., Sep. 2001;47(9): PubMed PMID: 11514393., 1607-1613.
Chiu, et al., "Noninvasive prenatal exclusion of congenital adrenal hyperplasia by maternal plasma analysis: a feasibility study", Clin Chem., May 2002;48(5), 778-780.
Chothia, C. et al., "Canonical structures for the hypervariable regions of immunoglobulins", Journal of Molecular Biology, vol. 196, No. 4, Aug. 20, 1987, 901-917.
Chu, et al., "A novel approach toward the challenge of accurately quantifying fetal DNA in maternal plasma", Prenat Diagn., Dec. 2010;30(12-13): doi: 10.1002/pd.2656, 1226-1229.
Chun, et al., "Dual priming oligonucleotide system for the multiplex detection of respiratory viruses and SNP genotyping of CYP2C19 gene", Nucleic Acids Research, vol. 35, No. 6, 2007, 1-6.
Chung, et al., "Cell-free DNA fetal fraction and pregnancy outcome", American Journal of Obstetrics & Gynecology, vol. 222, No. 1, 2019, S157.
Clementi, et al., "The Role of Cell-Free Plasma DNA in Critically Ill Patients with Sepsis", Blood Purif., 2016;41(1-3): doi: 10.1159/000440975. Epub Oct. 20, 2015, 34-40.
Coombs, Catherine et al., "Therapy-Related Clonal Hematopoiesis in Patients with Non-hematologic Cancers Is Common and Associated with Adverse Clinical Outcomes", Cell Stem Cell, vol. 21, No. 3, 2017, 374.
Costa, J.-M. et al., "Fetal RHD genotyping in maternal serum during the first trimester of pregnancy", British Journal of Haematology, vol. 119, 2002, 255-260.
Croft, Jr., Daniel et al., "Performance of Whole-Genome Amplified DNA Isolated from Serum and Plasma on High-Density Single Nucleotide Polymorphism Arrays", Journal of Molecular Diagnostics, 10(3), 2008, 249-257.
Daly, "Circulating donor-derived cell-free DNA: a true biomarker for cardiac allograft rejection?", Ann Transl Med., Mar. 2015;3(4):47. doi: 10.3978/j.issn.2305-5839.2015.01.35, 6 pages.
Dandel, et al., "Non-invasive cardiac allograft rejection surveillance: reliability and clinical value for prevention of heart failure", Heart Fail Rev., Mar. 2021;26(2): doi: 10.1007/s10741-020-10023-3. Epub Sep. 5, 2020, 319-336.
Daniels, G. et al., "Fetal blood group genotyping from DNA from maternal plasma: an important advance in the management and prevention of haemolytic disease of the fetus and newborn", Vox Sanguinis, vol. 87, 2004, 223-232.
Dastsooz, et al., "Multiplex ARMS PCR to Detect 8 Common Mutations of ATP7B Gene in Patients With Wilson Disease", Hepat Mon., May 16, 2013;13(5):e8375. doi: 10.5812/hepatmon.8375. eCollection 2013., 7 pages.
De Vlaminck, et al., "Circulating cell-free DNA enables noninvasive diagnosis of heart transplant rejection", Sci Transl Med., Jun. 18, 2014;6(241):241ra77. doi: 10.1126/scitranslmed.3007803, 20 pages.

(56) References Cited

OTHER PUBLICATIONS

De Vlaminck, et al., "Circulating cell-free DNA enables noninvasive diagnosis of heart transplant rejection", Sci Transl Med., Jun. 18, 2014;6(241):241ra77. Supplemental Materials., 6 pages.
De Vlaminck, et al., "Noninvasive monitoring of infection and rejection after lung transplantation", Proc Natl Acad Sci U S A, Oct. 27, 2015;112(43): doi: 10.1073/pnas. 1517494112. Epub Oct. 12, 2015, 13336-13341.
Delgado, et al., "Characterization of cell-free circulating DNA in plasma in patients with prostate cancer", Tumour Biol., Apr. 2013;34(2): doi: 10.1007/s13277-012-0634-6. Epub Dec. 27, 2012, 983-986.
Deshpande, et al., "Relationship Between Donor Fraction Cell-Free DNA and Treatment for Rejection in Heart Transplantation", Pediatric Transplantation, Jun. 2022; 26(4):e14264. https://doi.org/10.1111/petr.14264, 11 pages.
Deusen, et al., "Comprehensive Detection of Driver Mutations in Acute Myeloid Leukemia Including Internal Tandem Duplications with Anchored Multiplex PCR and Next-Generation Sequencing", Blood, vol. 128, No. 22, 2016, 5251.
Dey, et al., "A plasma telomeric cell-free DNA level in unaffected women with BRCA1 or/and BRCA2 mutations: a pilot study. Oncotarget", Oncotarget, Dec. 29, 2017;9(3): doi: 10.18632/oncotarget.23767. eCollection Jan. 9, 2018, 4214-4222.
Dharajiya, Nilesh et al., "Incidental Detection of Maternal Neoplasia in Noninvasive Prenatal Testing", Clinical Chemistry, vol. 64, No. 2, 2018, 329-335.
Diaz, et al., "Liquid Biopsies: Genotyping Circulating Tumor DNA", Journal of Clinical Oncology, vol. 32, No. 6, 2014, 579-586.
Diehl, et al., "Detection and quantification of mutations in the plasma of patients with colorectal tumors", Proceedings of the National Academy of Sciences, vol. 102, 2005, 16368-16373.
Ding, et al., "New Progress in Plasma Cell-free DNA in Clinical Applications", Progress in Modern Biomedicine, 2016; 18: 3476, 3593-3596.
Dwivedi, et al., "Prognostic utility and characterization of cell-free DNA in patients with severe sepsis", Crit Care, Aug. 13, 2012;16(4):R151. doi: 10.1186/cc11466., 11 pages.
Ehlayel, A. et al., "Emerging monitoring technologies in kidney transplantation", Pediatric Nephrology, vol. 36, 2021, 3077-3087.
Findlay, I. et al., "Allelic drop-out and preferential amplification in single cells and human blastomeres: implications for preimplantation diagnosis of sex and cystic fibrosis", Molecular Human Reproduction, vol. 1, 1995, 1609-1618.
Fire, et al., "Rolling replication of short DNA circles", PNAS, 1995, 4641-4645.
Fleischhacker, et al., "Circulating nucleic acids (CNAs) and cancer—a survey", Biochim Biophys Acta, Jan. 2007;1775(1): doi: 10.1016/j.bbcan.2006.10.001. Epub Oct. 7, 2006, 181-232.
García Moreira, et al., "Cell-free DNA as a noninvasive acute rejection marker in renal transplantation", Clin Chem., Nov. 2009;55(11): doi:10.1373/clinchem.2009.129072. Epub Sep. 3, 2009, 1958-1966.
Garnacho-Montero, et al., "Prognostic and diagnostic value of eosinopenia, C-reactive protein, procalcitonin, and circulating cell-free DNA in critically ill patients admitted with suspicion of sepsis", Crit Care, Jun. 5, 2014;18(3):R116. doi: 10.1186/cc13908, 9 pages.
Ghanta, et al., "Non-invasive prenatal detection of trisomy 21using tandem single nucleotide polymorphisms", PLoS One, Oct. 8, 2010;5(10):e13184. doi: 10.1371/journal.pone.0013184, 10 pages.
Gielis, et al., "Cell-Free DNA: An Upcoming Biomarker in Transplantation", Am J Transplant, Oct. 2015;15(10): doi: 10.1111/ajt.13387. Epub Jul. 16, 2015, 2541-2551.
Gielis, et al., "Plasma donor-derived cell-free DNA kinetics after kidney transplantation using a single tube multiplex PCR assay", PLoS One, 2018; 13(12): e0208207, 16 pages.
Giulio, Genovese et al., "Hematopoiesis and Blood-Cancer Risk Inferred from Blood DNA Sequence", The New England Journal of Medicine, vol. 371, No. 26, 2014, 2477-2487.
Glaab, et al., "A novel assay for allelic discrimination that combines the fluorogenic 5' nuclease polymerase chain reaction (TaqMan) and mismatch amplification mutation assay", Mutat Res., Nov. 29, 1999;430(1), 1-12.
Glaab, W. E. et al., "A novel assay for allelic discrimination that combines the fluorogenic 5' nuclease polymerase chain reaction (TaqMan) and mismatch amplification mutation assay", Mutation Research, vol. 430, 1999, 12 pgs.
Gordon, et al., "An Algorithm Measuring Donor Cell-Free DNA in Plasma of Cellular and Solid Organ Transplant Recipients That Does Not Require Donor or Recipient Genotyping", Front Cardiovasc Med., Sep. 22, 2016;3:33. eCollection 2016., 10 pages.
Gordon, Paul et al., "An Algorithm Measuring Donor Cell-Free DNA in Plasma of Cellular and Solid Organ Transplant Recipients That Does Not Require Donor or Recipient Genotyping", Frontiers in Cardiovascular Medicine, 2016, vol. 3.
Gormally, et al., "Amount of DNA in plasma and cancer risk: a prospective study", Int J Cancer, Sep. 20, 2004;111(5): doi: 10.1002/ijc.20327, 746-749.
Gotoh, et al., "Prediction of MYCN amplification in neuroblastoma using serum DNA and real-time quantitative polymerase chain reaction", J Clin Oncol., Aug. 1, 2005;23(22): PubMed PMID: 16051962., 5205-5210.
Grenda, R. , "Torque teno (TTV) viral load as a biomarker of immunosuppressive strength after kidney transplantation in children", Pediatric Nephrology, vol. 36, May 27, 2020, 3 pages.
Gripp, et al., "*Homo sapiens* KRAS proto-oncogene, GTPase (KRAS), RefSeqGene (LRG_344) on chromosome 12", GenBank Submission; Accession No. NG_007524, version NG_007524.2, Aug. 16, 2020., 16 Pages.
Grskovic, et al., "Validation of a Clinical-Grade Assay to Measure Donor-Derived Cell-Free DNA in Solid Organ Transplant Recipients", J Mol Diagn., Nov. 2016;18(6): doi: 10.1016/j.jmoldx.2016.07.003. Epub 2016, 890-902.
Guedj, et al., "A refined molecular taxonomy of breast cancer", Oncogene, Mar. 1, 2012;31(9):1196-206. doi: 10.1038/onc.2011.301. Epub Jul. 25, 2011, 34 pages.
Gusella, J. et al., "Precise localization of human B-globin gene complex on chromosome 11*", Proc. Natl. Acad. Sci USA, vol. 76, No. 10, Oct. 1979, 5239-5243.
Hainer & Fazzio, , "High-Resolution Chromatin Profiling Using CUT&RUN", Current Protocols in Molecular Biology, 2019, 1-22.
Hasi, et al., "Acetaldehyde dehydrogenase 2 SNP rs671 and susceptibility to essential hypertension in Mongolians: a case control study", Genet Mol Res., Mar. 29, 2011;10(1). doi: 10.4238/vol10-1gmr1056., 537-543.
Hidestrand, et al., "Highly sensitive noninvasive cardiac transplant rejection monitoring using targeted quantification of donor-specific cell-free deoxyribonucleic acid", J Am Coll Cardiol., Apr. 1, 2014;63(12). doi: 10.1016/j.jacc.2013.09.029. Epub Oct. 16, 2013, 1224-1226.
Hidestrand, et al., "Highly Sensitive Transplant Rejection Surveillance Using Targeted Detection of Donor Specific Cell Free DNA", J Heart Lung Transplant, Apr. 2012; 31(4), S91-S92.
Hidestrand, et al., "Influence of temperature during transportation on cellfree DNA analysis", Fetal Diagn Ther., 2012; 31, 122-128.
Hidestrand, et al., "Quantification of Circulating Donor Specific Cell Free DNA Is an Exquisitely Sensitive Non-Invasive Indicator of Injury to the Donor Heart", J Heart Lung Transplant, 2013; 32, S101-S102.
Hiendleder, et al., "Functional genomics: tools for improving farm animal health and welfare", Rev. Sci. Tech. Off. Int. Epiz., 24 (1), 2005, 354-377.
Hoerning, et al., "Quantitative real-time ARMS-qPCR for mitochondrial DNA enables accurate detection of microchimerism in renal transplant recipients", Pediatr Transplant, Dec. 2011; 15(8). doi: 10.1111/j.1399-3046.2011.01581.x. Epub Oct. 4, 2011, 809-818.
Hou, et al., "Application of tetra primer ARMS-PCR approach for detection of Fusarium graminearum genotypes with resistance to carbendazim", Australian Plant Pathology, Jan. 1, 2013; 42(1), 73-78.
Huang, et al., "Circulating cell-free DNA levels correlate with postresuscitation survival rates in out-of-hospital cardiac arrest

(56) References Cited

OTHER PUBLICATIONS patients", Resuscitation, Feb. 2012;83(2): doi: 10.1016/j.resuscitation.2011.07.039. Epub Aug. 22, 2011, 213-218.
Huang, et al., "*Homo sapiens* TSC complex subunit 1 (TSC1), RefSeqGene (LRG_486) on chromosome 9", GenBank Submission; Accession No. NG_012386, version NG_012386.1, Sep. 21, 2020, 20 Pages.
Hudecova, "Digital PCR analysis of circulating nucleic acids", Clin Biochem., Oct. 2015;48(15): doi: 10.1016/j.clinbiochem.2015.03.015. Epub Mar. 28, 2015, 948-956.
Hugon, et al., "Influence of intention to adhere, beliefs and satisfaction about medicines on adherence in solid organ transplant recipients", Transplantation., Jul. 27, 2014;98(2): doi: 10.1097/TP.0000000000000221, 222-228.
Illumina, "HumanOmni1-Quad BeadChip", Illumina DNA Analysis, Pub. No. 370-21009-007, 2009, 1 page.
Illumina, "HumanOmni2.5-8 BeadChips: Next-Generation GWAS Content for Genotyping and CNV Analysis", Data Sheet: DNA Analysis, Pub. No. 370-2011-008, 2011, 1 page.
Illumina, "Illumina Adapter Sequences", Published by Illumina, 2018, 1-45.
Jaiswal, Siddhartha et al., "Clonal hematopoiesis in human aging and disease", Science, vol. 366, No. 6465, 2019, 4.
Ji, Xing et al., "Copy number variation profile in noninvasive prenatal testing (NIPT) can identify co-existing maternal malignancies: Case reports and a literature review", Taiwanese Journal of Obstetrics and Gynecology, vol. 57, No. 6, 2018, 871-877.
Jing, et al., "Cell-free DNA: characteristics, detection and its applications in myocardial infarction", Curr Pharm Des., 2013;19(28): doi: 10.2174/1381612811319280012., 5135-5145.
Jordan, et al., "Donor-derived Cell-free DNA Identifies Antibody-mediated Rejection in Donor Specific Antibody Positive Kidney Transplant Recipients", Transplant Direct, 2018;4(9):e379, 5 pages.
Jordens, et al., "Amplification with molecular beacon primers and reverse line blotting for the detection and typing of human papillomaviruses", Journal of Virological Methods, vol. 89, 2000, 29-37.
Jung, et al., "Cell-free DNA in the blood as a solid tumor biomarker—a critical appraisal of the literature", Clin Chim Acta., Nov. 11, 2010;411(21-22): doi: 10.1016/j.cca.2010.07.032. Epub Aug. 2, 2010, 1611-1624.
Kaboev, et al., "PCR hot start using primers with the structure of molecular beacons (hairpin-like structure)", Nucleic Acids Research, vol. 28, 2000, 1-2.
Kane, et al., "Application of less primer method to PCR", DNA Polymorphism, 2004, vol. 13, pp. 34-37.
Karapetis, et al., "K-ras mutations and benefit from cetuximab in advanced colorectal cancer", N Engl J Med., Oct. 23, 2008;359(17). doi: 10.1056/NEJMoa0804385., 1757-1765.
Keshavjee, S. H. et al., "The role of dextran 40 and potassium in extended hypothermic lung preservation for transplantation", The Journal of Thoracic and Cardiovascular Surgery, vol. 103, No. 2, 1992.
Khater & Khauli, "Pseudorejection and true rejection after kidney transplantation: classification and clinical significance", Urol Int., 90(4), 2012, 373-80.
Khush, et al., "Circulating cell-free DNA as a non-invasive marker of pediatric heart transplant rejection and immunosuppressive treatment", J Heart Lung Transplantation, Apr. 2016. 35(4):Abstract 181, S75.
Khush, et al., "Noninvasive detection of graft injury after heart transplant using donor/\derived cell/\free DNA: A prospective multicenter study", Am J Transplant, Oct. 2019;19(10): doi: 10.1111/ajt.15339. Epub Apr. 8, 2019, 2889-2899.
Kim, et al., "Personalized therapy on the horizon for squamous cell carcinoma of the lung", Lung Cancer, vol. 80, 2013, 249-255.
Kindel, et al., "Early Changes in Donor Fraction Cell-free DNA in Newly Transplanted Heart Transplant Patients", ISHLT DF cfDNA declanation poster, 2018, 1 Page.
Kirkizlar, et al., "Detection of Clonal and Subclonal Copy-Number Variants in Cell-Free DNA from Patients with Breast Cancer Using a Massively Multiplexed PCR Methodology", Transl Oncol., Oct. 2015;8(5): doi: 10.1016/j.tranon.2015.08.004., 407-416.
Kittler, R. et al., "A Whole Genome Amplification Method to Generate Long Fragments from Low Quantities of Genomic DNA", Analytical Biochemistry, vol. 300, 2002, 237-244.
Kiyomi, Morita et al., "Clearance of Somatic Mutations at Remission and the Risk of Relapse in Acute Myeloid Leukemia", J Clin Oncol, vol. 36, No. 18, 2018, 1788-1797.
Koeppe, et al., "HIV-1-Specific CD4+ T-Cell Responses Are Not Associated With Significant Viral Epitope Variation in Persons With Persistent Plasma Viremia", J Acquir Immune Defic Syndr, 2006, 41:140-148.
Krishnakumar, S. et al., "A comprehensive assay for targeted multiplex amplification of human DNA sequences", PNAS, vol. 105, No. 27, Jul. 8, 2008, 9296-9301.
Ku, et al., "Exome versus transcriptome sequencing in identifying coding region variants", Expert Review of Molecular Diagnostics, vol. 12, 2012, 241-251.
Kulifaj, D. et al., "Development of a standardized real time PCR for Torque teno viruses (TTV) viral load detection and quantification: A new tool for immune monitoring", Journal of Clinical Virology, vol. 105, 2018, 118-127.
Kuo, et al., "Preimplantation and prenatal genetic diagnosis of aromatic L-amino acid decarboxylase deficiency with an amplification refractory mutation system-quantitative polymerase chain reaction", Taiwan J Obstet Gynecol, Dec. 2011;50(4): doi: 10.1016/j.tjog.2011.10.012., 468-473.
Kustanovich, et al., "Life and death of circulating cell-free DNA", Cancer Biol Ther., 2019;20(8): doi: 10.1080/15384047.2019.1598759. Epub Apr. 16, 2019, 1057-1067.
Lajin, et al., "A quadruplex tetra-primer ARMS-PCR method for the simultaneous detection of TP53 Arg72Pro, IVS3 16bp Del/Ins and IVS6+62A>G, and NQO1 C609T polymorphisms", Gene., Aug. 10, 2012;504(2): Epub May 23, 2012, 268-273.
Lajoie, B. R. et al., "The Hitchhiker's Guide to Hi-C Analysis: Practical guidelines", Methods: Author manuscript, vol. 72, Jan. 2015, 65-75.
Landegren, U. et al., "Reading Bits of Genetic Information: Methods for Single-Nucleotide Polymorphism Analysis", Genome Research, vol. 8, No. 8, 769-776, 1997.
Lang, et al., "Optimized allele-specific real-time PCR assays for the detection of common mutations in KRAS and BRAF", J Mol Diagn., Jan. 2011;13(1): doi: 10.1016/j.jmoldx.2010.11.007. Epub Dec. 23, 2010, 23-28.
Laurent-Puig, et al., "Clinical relevance of KRAS-mutated subclones detected with picodroplet digital PCR in advanced colorectal cancer treated with anti-EGFR therapy", Clin Cancer Res., Mar. 1, 2015;21(5): doi: 10.1158/1078-0432.CCR-14-0983. Epub Sep. 23, 2014, 1087-1097.
Lecomte, et al., "Detection of free-circulating tumor-associated DNA in plasma of colorectal cancer patients and its association with prognosis", Int J Cancer, Aug. 10, 2002;100(5): doi: 10.1002/ijc.10526., 542-548.
Lee, et al., "Allele-Specific Quantitative PCR for Accurate, Rapid, and Cost-Effective Genotyping", Hum Gene Ther., Jun. 2016;27(6): doi: 10.1089/hum.2016.011. Epub Mar. 17, 2016, 425-435.
Lefebure, et al., "Prognostic value of circulating mutant DNA in unresectable metastatic colorectal cancer", Ann Surg., Feb. 2010;251(2): doi: 10.1097/SLA.0b013e3181c35c87, 275-280.
Lenaerts, Liesbeth et al., "Noninvasive Prenatal Testing and Detection of Occult Maternal Malignancies", Clinical Chemistry, vol. 65, No. 12, 2019, 1484-1486.
Levy, et al., "Analysis of Cell-Free DNA to Assess Risk of Tumoremia Following Endoscopic Ultrasound Fine-Needle Aspiration of Pancreatic Adenocarcinomas", Clin Gastroenterol Hepatol., Oct. 2018;16(10): e1. doi: 10.1016/j.cgh.2018.02.048. Epub Mar. 8, 2018, 1632-1640.
Li, et al., "Multiplex co-amplification of 24 retinoblastoma gene exons after pre-amplification by long-distance PCR", Nucleic Acids Res., Feb. 1, 1996;24(3), 538-539.
Liang, et al., "Cationic nanoparticle as an inhibitor of cell-free DNA-induced inflammation", Nat Commun., Oct. 16, 2018;9(1):4291. doi: 10.1038/s41467-018-06603-5, 14 pages.

(56) References Cited

OTHER PUBLICATIONS

Lievre, et al., "KRAS mutations as an independent prognostic factor in patients with advanced colorectal cancer treated with cetuximab", J Clin Oncol., Jan. 20, 2008;26(3): doi: 10.1200/JCO.2007.12.5906., 374-379.
Lin, et al., "A new diagnostic system for ultra-sensitive and specific detection and quantification of Candidatus Liberibacter asiaticus, the bacterium associated with citrus Huanglongbing", J Microbial Methods, 2010, 17-25.
Liu, et al., "ABO chimerism determined by real-time polymerase chain reaction analysis after ABO-incompatible haematopoietic stem cell transplantation", Blood Tranfus, Jan. 2013;11(1): doi: 10.2450/2012.0013-12. Epub Jul. 4, 2012, 43-52.
Liu, et al., "Comparison of next-generation sequencing systems", J Biomed Biotechnol., 2012;2012: doi: 10.1155/2012/251364. Epub Jul. 5, 2012, 1-11.
Livergood, "Adverse perinatal outcomes and cell free DNA no calls: Beyond low fetal fraction", American Journal of Obstetrics & Gynecology, vol. 218, No. 1, 2018, S169.
Lizardi, et al., "Mutation detection and single-molecule counting using isothermal rolling-circle amplification", Nature Genetics, 1998, 225-232.
Llop, et al., "Development of a highly sensitive nested-PCR procedure using a single closed tube for detection of Erwinia amylovora in asymptomatic plant material", Appl Environ Microbial., 2000, 2071-8.
Lo, et al., "Plasma placental RNA allelic ratio permits noninvasive prenatal chromosomal aneuploidy detection", Nat Med., Feb. 2007;13(2): doi: 10.1038/nm1530. Epub Jan. 7, 2007, 218-223.
Lo, et al., "Transplantation monitoring by plasma DNA sequencing", Clin Chem., Jul. 2011;57(7): doi: 10.1373/clinchem.2011.166686. PubMed PMID: 21566070, 941-942.
Lo, Y.M. D. et al., "Prenatal Diagnosis of Fetal RhD Status by Molecular Analysis of Maternal Plasma", The New England Journal of Medicine, vol. 339, No. 24, 1998, 1734-1738.
Luo, et al., "Detection of usual and atypical aldehyde dehydrogenase alleles by mismatch amplification mutation assay", Clin Chem Lab Med., Dec. 2001;39(12): doi: 10.1515/CCLM.2001.189., 1195-1197.
Maheswaran, S. et al., "Detection of Mutations in EGFR in Circulating Lung-Cancer Cells", N Engl J Med, vol. 359, No. 4, Jul. 24, 2008, 366-377.
Mak, et al., "Rapid diagnosis of Wilson disease by a 28-mutation panel: real-time amplification refractory mutation system in diagnosing acute Wilsonian liver failure", Clin Chim Acta., Dec. 2008; 398(1-2): doi: 10.1016/j.cca.2008.08.002. Epub Aug. 8, 2008, 39-42.
Mamanova, L. et al., "Target-enrichment strategies for next-generation sequencing", Nat Methods, vol. 7, 2010, 111-118.
Mamun, et al., "The *Escherichia coli* UVM response is accompanied by an SOS-independent error-prone DNA replication activity demonstrable in vitro", Molecular Microbiology, 2000, 368-380.
Manage, et al., "Genotyping single nucleotide polymorphisms in human genomic DNA with an automated and self-contained PCR cassette", J Mol Diagn., Sep. 2014;16(5): doi:10.1016/j.jmoldx.2014.04.004. Epub Jul. 2, 2014, 550-557.
Margulies, et al., "Genome Sequencing in Open Microfabricated High Density Picoliter Reactors", Nature, 437(7057), 2005, 376-380.
Martinez-Herrero, et al., "Cancer protection elicited by a single nucleotide polymorphism close to the adrenomedullin gene", J Clin Endocrinol Metab., Apr. 2013;98(4): doi: 10.1210/jc.2012-4193. Epub Feb. 28, 2013, E807-E810.
Marusyk, et al., "Causes and consequences", Biochimica et Biophysica Acta, vol. 1805, 2010, 105-117.
Mehra, et al., "Gene expression profiles and B-type natriuretic peptide elevation in heart transplantation: more than a hemodynamic marker", Circulation, Jul. 4, 2006;114(1 Suppl), I21-I26.
Mehra, et al., "International Society for Heart and Lung Transplantation working formulation of a standardized nomenclature for cardiac allograft vasculopathy-2010", J Heart Lung Transplant, Jul. 2010;29(7) .doi: 10.1016/j.healun.2010.05.017., 717-727.
Mengel, et al., "The molecular phenotype of heart transplant biopsies: relationship to histopathological and clinical variables", Am J Transplant, Sep. 2010;10(9): doi: 10.1111/j.1600-6143.2010.03182.x., 2105-2115.
Metzker, Michael, Declaration of Michael L. Metzker, Ph.D. from IPR2018-01317, 2004.
Misale, et al., "Emergence of KRAS mutations and acquired resistance to anti-EGFR therapy in colorectal cancer", Nature, Jun. 28, 2012;486(7404): doi: 10.1038/nature11156., 532-536.
Mouliere, et al., "Circulating Cell-Free DNA from Colorectal Cancer Patients May Reveal High KRAS or BRAF Mutation Load", Transl Oncol., Jun. 1, 2013;6(3): doi: 10.1593/tlo.12445. Print Jun. 2013., 319-328.
Mueller, P. R. et al., "In Vivo Footprinting of a Muscle Specific Enhancer by Ligation Mediated PCR", Science, vol. 249, Nov. 10, 1989, 780-786.
Myers, et al., "ACB-PCR quantification of somatic oncomutation", Methods Mol Biol., 2014; 1105: doi: 10.1007/978-1-62703-739-6_27, 345-363.
Namlos, H.M. et al., "Use of liquid biopsies to monitor disease progression in a sarcoma patient: a case report", BMC Cancer, vol. 17, No. 1, 2017, 2-3.
Nelson, C. M. et al., "Whole genome transcription profiling of Anaplasma phagocytohilum in human and tick host cells by tiling array analysis", BMC Genomics, vol. 9, No. 364, Jul. 31, 2008, 16 pgs.
Newton, et al., "Analysis of any point mutation in DNA. The amplification refractory mutation system (ARMS)", Nucleic Acids Res., Apr. 11, 1989;17(7): doi: 10.1093/nar/17.7.2503, 2503-2516.
Nilsson, et al., "Analyzing genes using closing and replicating circles", Trends in Biotechnology, 24, 2006, 83-88.
No Author Listed, "Jury Rules in Favor of Natera, Finding All Asserted Patents Valid and Infrindged by ArcherDX/Invitae; Awards $19.35 Million in Past Damages for Royalties and Lost Profits", Natera Press Release, 2023, 4 pgs.
No Author Listed, "*Natera Inc.* vs. *ArcherDx* Verdict Form, Case 1:20-CV-00125-GBW", 2023, 1-12.
North, et al., "Cell-free DNA donor fraction analysis in pediatric and adult heart transplant patients by multiplexed allele-specific quantitative PCR: Validation of a rapid and highly sensitive clinical test for stratification of rejection probability", PLoS One, Jan. 13, 2020;15(1):e0227385. doi: 10.1371/journal.pone.0227385. eCollection 2020, 48 pages.
Norton, et al., "Perinatal and genetic outcomes associated with no call cfDNA results in 18,496 pregnancies", American Journal of Obstetrics & Gynecology, vol. 224, No. 2, 2021, S3.
Oeth, et al., "Qualitative and quantitative genotyping using single base primer extension coupled with matrix-assisted laser desorption/ionization time-of-flight mass spectrometry (MassARRAY®).", Methods Mol. Biol., 2009; 578, 307-343.
Ohya, K. et al., "Detection of the CTG Repeat Expansion in Congenital Myotonic Dystrophy", Jpn J. Human Genet, vol. 42, 1997, 169-180.
Orou, et al., "Allele-specific competitive blocker PCR: a one-step method with applicability to pool screening", Hum Mutat., 1995;6(2): doi: 10.1002/humu.1380060209., 163-169.
Parsons, et al., "Allele-specific competitive blocker-PCR detection of rare base substitution", Methods Mol Biol., 2005;291, 235-245.
PCT/US2017/059808, "International Preliminary Report on Patentability", mailed May 16, 2019, 8 pages.
PCT/US2017/059808, "International Search Report and Written Opinion for Application", mailed Jan. 25, 2018, 12 pages.
PCT/US2018/038598, "International Preliminary Report on Patentability", mailed Jan. 2, 2020, 6 pages.
PCT/US2018/038598, "International Search Report and Written Opinion", mailed Sep. 7, 2018, 8 pages.
PCT/US2018/038609, "International Preliminary Report on Patentability", mailed Jan. 2, 2020, 7 pages.
PCT/US2018/038609, "International Search Report and Written Opinion", mailed Sep. 10, 2018, 9 pages.

(56) References Cited

OTHER PUBLICATIONS

Peng, et al., "Comparison of K-ras mutations in lung, colorectal and gastric cancer", Oncol Lett., Aug. 2014;8(2): doi: 10.3892/ol.2014.2205. Epub May 30, 2014, 561-565.
Peng, Q et al., "Reducing amplification artifacts in high multiplex amplicon sequencing by using molecular barcodes", BMC Genomics, vol. 16. No. 586, 2015, 12 pages.
Peyster, et al., "Advanced Morphologic Analysis for Diagnosing Allograft Rejection: The Case of Cardiac Transplant Rejection", Transplantation, Aug. 2018;102(8): doi: 10.1097/TP.0000000000002189., 1230-1239.
Price, et al., "Cost-effective interrogation of single nucleotide polymorphisms using the mismatch amplification mutation assay and capillary electrophoresis", Electrophoresis, Dec. 2010;31(23-24): doi: 10.1002/elps.201000379., 3881-3888.
Purhonen, et al., "Human plasma cell-free DNA as a predictor of infectious complications of neutropenic fever in hematological patients", Infect Dis (Lond)., Apr. 2015;47(4): doi: 10.3109/00365548.2014.985711. Epub Feb. 9, 2015, 255-259.
Qin, et al., "Quantitative assessment of hematopoietic chimerism by quantitative real-time polymerase chain reaction of sequence polymorphism systems after hematopoietic stem cell transplantation", Chin Med J (Engl), Aug. 2011;124(15), 2301-2308.
Quail, et al., "A tale of three next generation sequencing platforms: comparison of lon torrent, pacific biosciences and illumina MiSeq sequencers", BMC Genomics, Jul. 24, 2012; 13:341. doi: 10.1186/1471-2164-13-341, 13 pages.
Raemdonck, Dirk Van et al., "Ex-vivo lung perfusion", Transplant International, vol. 28, Issue 6, Special Issue: Focus Issue: Machine Perfusion, 2014, 643-656.
Ragalie, et al., "Description of Longitudinal Measurement of Donor Fraction of Cell-Free DNA and Correlation to Clinical Outcomes", ISHLT poster, 2018, 1 page.
Ragalie, et al., "Noninvasive Assay for Donor Fraction of Cell-Free DNA in Pediatric Heart Transplant Recipients", J Am Coll Cardiol., Jun. 26, 2018;71(25): doi: 10.1016/j.jacc.2018.04.026, 2982-2983.
Rechitsky, S. et al., "Allele Dropout in Polar Bodies and Blastomeres", Journal of Assisted Reproduction and Genetics, vol. 15, No. 5, 1998, 253-257.
Reinert, et al., "Analysis of Plasma Cell-Free DNA by Ultradeep Sequencing in Patients With Stages I to UI Colorectal Cancer", JAMA Oncology, 2019, 1-74.
Richmond, et al., "Donor fraction cell-free DNA and rejection in adult and pediatric heart transplantation", J Heart Lung Transplant, May 2020;39(5): doi: 10.1016/j.healun.2019.11.015. Epub Nov. 29, 2019, 454-463.
Roedder, et al., "Biomarkers in solid organ transplantation: establishing personalized transplantation medicine", Genome Med., Jun. 8, 2011;3(6):37, 12 pages.
Sanmamed, et al., "Quantitative cell-free circulating BRAFV600E mutation analysis by use of droplet digital PCR in the follow-up of patients with melanoma being treated with BRAF inhibitors", Clin Chem., Jan. 2015;61(1): doi: 10.1373/clinchem.2014.230235. Epub Nov. 19, 2014, 297-304.
Sapio, et al., "Detection of BRAF mutation in thyroid papillary carcinomas by mutant allele-specific PCR amplification (MASA)", Eur J Endocrinol., Feb. 2006;154(2): doi: 10.1530/eje.1.02072, 341-348.
Saukkonen, et al., "Cell-free plasma DNA as a predictor of outcome in severe sepsis and septic shock.", Clin Chem., Jun. 2008;54(6): doi: 10.1373/clinchem.2007.101030. Epub Apr. 17, 2008. PubMed PMID: 18420731, 1000-1007.
Scheffer, et al., "Association between low fetal fraction in cell-free DNA testing and adverse pregnancy outcome: A systematic review", Prenatal Diagnosis, vol. 41, No. 10, 2021, 1287-1295.
Schnittger, et al., "Development and validation of a real-time quantification assay to detect and monitor BRAFV600E mutations in hairy cell leukemia", Blood., Mar. 29, 2012;119(13): doi: 10.1182/blood-2011-10-383323. Epub Feb. 13, 2012, 3151-3154.
Schutz, et al., "Graft-derived cell-free DNA, a noninvasive early rejection and graft damage marker in liver transplantation: A prospective, observational, multicenter cohort study", PLoS Med., Apr. 25, 2017;14(4):e1002286. doi: 10.1371/journal.pmed. 1002286. eCollection Apr. 2017., 19 pages.
Schutz, E. et al., "Graft-derived cell-free DNA, a noninvasive early rejection and graft damage marker in liver transplantation: A prospective, observational, multicenter cohort study", PLOS Medicine, vol. 14, No. 4, Apr. 25, 2017, 19 pgs.
Schwarzenbach, et al., "Cell-free nucleic acids as biomarkers in cancer patients", Nat Rev Cancer, Jun. 2011;11(6): doi: 10.1038/nrc3066. Epub May 12, 2011, 426-437.
Scott, et al., "Elevated nuclear and mitochondrial cell-free deoxyribonucleic acid measurements are associated with death after infant cardiac surgery", J Thorac Cardiovasc Surg., Aug. 2022; 164(2): doi: 10.1016/j.jtcvs.2021.10.066. Epub Dec. 24, 2021, 367-375.
Scott, et al., "Total Cell-Free DNA Predicts Death and Infection Following Pediatric and Adult Heart Transplantation", Ann Thorac Surg., Oct. 2021;112(4): doi: 10.1016/j.athoracsur.2020.08.006. Epub Oct. 8, 2020., 1282-1289.
Sefrioui, et al., "Clinical value of chip-based digital-PCR platform for the detection of circulating DNA in metastatic colorectal cancer", Dig Liver Dis., Oct. 2015;47(10): doi: 10.1016/j.dld.2015.05.023. Epub Jun. 5, 2015, 884-890.
Selzner, Markus et al., "Normothermic Ex Vivo Liver Perfusion Using Steen Solution as Perfusate for Human Liver Transplantation: First North American Results", Liver Transplantation, vol. 22, Issue 11, 2016.
Sethi, Himanshu et al., "Analytical validation of the Signatera (TM) RUO assay, a highly sensitive patient-specific multiplex PCR NGS-based noninvasive cancer recurrence detection and therapy monitoring assay", Cancer Research, vol. 78, No. 13, 2018, 4542.
Sheffield, et al., "Attachment of a 40-base-pair G + C-rich sequence (GC-clamp) to genomic DNA fragments by the polymerase chain reaction results in improved detection of single-base changes", Proc Natl Acad Sci USA, Jan. 1989;86(1), 232-236.
Shi, et al., "Development of a single multiplex amplification refractory mutation system PCR for the detection of rifampin-resistant Mycobacterium tuberculosis", Gene., Nov. 1, 2013; 530(1): Epub Aug. 19, 2013, 95-99.
Shimabukuro-Vornhagen, et al., "Cytokine release syndrome", J Immunother Cancer, Jun. 15, 2018;6(1):56. doi: 10.1186/s40425-018-0343-9, 14 pages.
Sigdel, et al., "A rapid noninvasive assay for the detection of renal transplant injury", Transplantation, Jul. 15, 2013;96(1): doi: 10.1097/TP.0b013e318295ee5a., 97-101.
Sigdel, Tara et al., "Optimizing Detection of Kidney Transplant Injury by Assessment of Donor-Derived Cell-Free DNA via Massively Multiplex PCR", Journal of Clinical Medicine, vol. 8, No. 1, 2018, 19.
Sigdel, Tara et al., "Plasma Donor-Derived Cell-Free DNA Quantification by massively multiplex PCR Distinguishes Kidney Transplant Acute Rejection", Transplantation, vol. 102, No. 7s, 2018, s178-s179.
Singh, et al., "Aspergillus infections in transplant recipients", Clin Microbiol Rev., Jan. 2005;18(1), 44-69.
Snyder, et al., "Universal noninvasive detection of solid organ transplant rejection", Proc Natl Acad Sci U S A, Apr. 12, 2011;108(15); doi: 10.1073/pnas.1013924108. Epub Mar. 28, 2011. PubMed PMID: 21444804; PubMed Central PMCID: PMC3076856, 6229-6234.
Sparks, et al., "Noninvasive prenatal detection and selective analysis of cell-free DNA obtained from maternal blood: evaluation for trisomy 21 and trisomy 18", Am J Obstet Gynecol., Apr. 2012;206(4): doi: 10.1016/j.ajog.2012.01.030. Epub Jan. 26, 2012, 319.e1-319.e9.
Sparks, et al., "Selective analysis of cell-free DNA in maternal blood for evaluation of fetal trisomy", Prenat Diagn., Jan. 2012;32(1). Epub Jan. 6, 2012, 3-9.
Spindler, et al., "Cell-free DNA in healthy individuals, noncancerous disease and strong prognostic value in colorectal cancer", Int J Cancer, Dec. 15, 2014;135(12): doi: 10.1002/ijc.28946. Epub Jun. 17, 2014, 2984-2991.

(56) References Cited

OTHER PUBLICATIONS

Spindler, et al., "KRAS-mutated plasma DNA as predictor of outcome from irinotecan monotherapy in metastatic colorectal cancer", Br J Cancer, Dec. 10, 2013;109(12). doi: 10.1038/bjc.2013.633. Epub Nov. 21, 2013, 3067-3072.
Spindler, et al., "Quantitative cell-free DNA, KRAS, and BRAF mutations in plasma from patients with metastatic colorectal cancer during treatment with cetuximab and irinotecan", Clin Cancer Res., Feb. 15, 2012;18(4). doi: 10.1158/1078-0432.CCR-11-0564. Epub Jan. 6, 2012, 1177-1185.
Steensma, D. P. et al., "Clonal hematopoiesis of indeterminate potential and its distinction from myelodysplastic syndromes", Blood, vol. 126, No. 1, 2015, 9-16.
Stein, "Next-Generation Sequencing Update", Genetic Engineering & Biotechnology News, Sep. 1, 2008; 28(15). https://www.genengnews.com/magazine/97/next-generation-sequencing-update/, 10 pages.
Steinborn, et al., "Coexistence of Bos taurus and B. indicus mitochondrial DNAs in nuclear transfer-derived somatic cattle clones", Genetics, Oct. 2002;162(2), 823-829.
Stemmer, et al., "Use of magnetic beads for plasma cell-free DNA extraction: toward automation of plasma DNA analysis for molecular diagnostics", Clin Chem., Nov. 2003;49(11): PubMed PMID: 14578335., 1953-1955.
Stone, J. P. et al., "Altered Immunogenicity of Donor Lungs via Removal of Passenger Leukocytes Using Ex Vivo Lung Perfusion", American Journal of Transplantation, vol. 16, 2016, 33-43.
Strausberg, et al., "*Homo sapiens* placenta-specific 4, mRNA (cDNA clone MGC: 120720 IMAGE:7939530), complete cds", GenBank Submission; Accession No. BC093685, version BC093685.1., Jan. 18, 2007, 2 Pages.
Strohmeier, et al., "Multiplex genotyping of KRAS point mutations in tumor cell DNA by allele-specific real-time PCR on a centrifugal microfluidic disk segment", Microchimica Acta., 2014;181 (13-14), 1681-1688.
Suzuki, et al., "Characterization of circulating DNA in healthy human plasma", Clin Chim Acta., Jan. 2008;387(1-2): doi: 10.1016/j.cca.2007.09.001. Epub Sep. 8, 2007, 55-58.
Swinkels, et al., "Effects of blood-processing protocols on cell-free DNA quantification in plasma", Clin Chem., Mar. 2003;49(3): PubMed PMID: 12600978, 525-526.
Tabernero, et al., "Analysis of circulating DNA and protein biomarkers to predict the clinical activity of regorafenib and assess prognosis in patients with metastatic colorectal cancer: a retrospective, exploratory analysis of the CORRECT trial", Lancet Oncol., Aug. 2015;16(8): doi: 10.1016/S1470-2045(15)00138-2. Epub Jul. 13, 2015, 937-948.
Taira, et al., "Novel high-speed droplet-allele specific-polymerase chain reaction: application in the rapid genotyping of single nucleotide polymorphisms", Clin Chim Acta., Sep. 23, 2013;424: doi: 10.1016/j.cca.2013.04.024. Epub May 17, 2013, 39-46.
Taira, et al., "Quantitative monitoring of single nucleotide mutations by allele-specific quantitative PCR can be used for the assessment of minimal residual disease in patients with hematological malignancies throughout their clinical course", Clin Chim Acta., Jan. 14, 2011;412(1-2): doi: 10.1016/j.cca.2010.09.011. Epub Sep. 16, 2010, 53-58.
Takai, et al., "Clinical utility of circulating tumor DNA for molecular assessment in pancreatic cancer", Sci Rep., Dec. 16, 2015;5:18425. doi: 10.1038/srep18425, 10 pages.
Taly, et al., "Multiplex picodroplet digital PCR to detect KRAS mutations in circulating DNA from the plasma of colorectal cancer patients", Clin Chem., Dec. 2013;59(12): doi: 10.1373/clinchem.2013.206359. Epub Aug. 12, 2013, 1722-1731.
Tamkovich, et al., "Circulating nucleic acids in blood of healthy male and female donors", Clin Chem., Jul. 2005; 51(7): PubMed PMID: 15976134., 1317-1319.
Tanem, et al., "Abstract 16873: Association of Preoperative Cell-Free DNA Levels and Outcome Following Pediatric Cardiopulmonary Bypass", Circulation, Nov. 17, 2020; 142(S3): https://doi.org/10.1161/circ.142.suppl_3.16873., 1-6.
Thermofisher Scientific, "How Ion AmpliSeq Targeted Sequencing Technology Works", https://www.thermofisher.com/us/en/home/life-science/ sequencing/next-generation-sequencing/ion-torrent-next-generation-sequencing-workflow/ion-torrent-next-generation-sequencing-select-targets/ampliseq-target-selection/how-ampliseq-technology-work.
Thierry, et al., "A Targeted Q-PCR-Based Method for Point Mutation Testing by Analyzing Circulating DNA for Cancer Management Care", Methods Mol Biol., 2016; 1392: doi: 10.1007/978-1-4939-3360-0_1, 1-16.
Thierry, et al., "Clinical validation of the detection of KRAS and BRAF mutations from circulating tumor DNA", Nat Med., Apr. 2014;20(4): doi: 10.1038/nm.3511. Epub Mar. 23, 2014, 430-435.
Tie, et al., "Circulating tumor DNA as an early marker of therapeutic response in patients with metastatic colorectal cancer", Annals of Oncology, vol. 26, No. 8, 2015, 1715-1722.
Tomita-Mitchell, et al., "Human gene copy No. spectra analysis in congenital heart malformations", Physiol Genomics, May 1, 2012;44(9): doi: 10.1152/physiolgenomics.00013.2012. Epub Feb. 7, 2012, 518-541.
Tong, et al., "Diagnostic developments involving cell-free (circulating) nucleic acids", Clin Chim Acta., Jan. 2006;363(1-2): Epub Aug. 26, 2005. Review. PubMed PMID: 16126188, 187-196.
Toth, T. et al., "Prenatal Detection of Trisomy 13 From Amniotic Fluid by Quantitative Fluorescent Polymerase Chain Reaction", Prenatal Diagnosis, vol. 18, 1998, 669-674.
Tungwiwat, et al., "Non-invasive fetal sex determination using a conventional nested PCR analysis of fetal DNA in maternal plasma", Clinica Chimica Acta, vol. 334, No. 1-2, 2003, 173-177.
Valenza, F. et al., "The Consumption of Glucose During Ex Vivo Lung Perfusion Correlates with Lung Edema", Transplantation Proceedings, vol. 43, 2011, 993-996.
Van Orsouw, et al., "Rapid design of denaturing gradient-based two-dimensional electrophoretic gene mutational scanning tests", Nucleic Acids Res., May 15, 1998;26(10), 2398-2406.
Vandekerkhove, G et al., "Circulating Tumor DNA Reveals Clinically Actionable Somatic Genome of Metastatic Bladder Cancer", Clinical Cancer Research, 2017, 6487-6497.
Vannucchi, et al., "A quantitative assay for JAK2(V617F) mutation in myeloproliferative disorders by ARMS-PCR and capillary electrophoresis", Leukemia, Jun. 2006;20(6), 1055-1060.
Ventura-Aguiar, P. et al., "Donor-derived Cell-free DNA Shows High Sensitivity for the Diagnosis of Pancreas Graft Rejection in Simultaneous Pancreas-Kidney Transplantation", Transplantation, vol. 00, No. 00, 2022, 8 pages.
Veseloskva, "The use of cell-free nucleic acids in maternal plasma for non-invasive prenatal diagnosis of monogenic diseases, placental insufficiency-related complications and Down syndrome", Thesis from Charles University in Prague, 2011, 104 pages.
Volckmar, et al., "A field guide for cancer diagnostics using cell-free DNA: From principles to practice and clinical applications", Genes Chromosomes Cancer, 2018, 123-139.
Wagner, F. F. et al., "RHD gene deletion occurred in the Rhesus box", Blood, vol. 95, No. 12, 2000, 3662-3668.
Wang, et al., "DNA Degradation Test Predicts Success in Whole-Genome Amplification from Diverse Clinical Samples", Journal of Molecular Diagnostics, vol. 9, 2007, 441-451.
Wang, et al., "Molecular inversion probes: a novel microarray technology and its application in cancer research", Cancer Genetics, 205, 2012, 341-355.
Wangkumhang, et al., "WASP: a Web-based Allele-Specific PCR assay designing tool for detecting SNPs and mutations", BMC Genomics, Aug. 14, 2007;8:275, 9 Pages.
Wangkumhang, P. et al., "WASP: a Web-based Allele-Specific PCR assay designing tool for detecting SNPs and mutations", BMC Genomics, vol. 8, No. 275, Aug. 14, 2007, 9 pgs.
Wapner, et al., "Expanding the scope of noninvasive prenatal testing: detection of fetal microdeletion syndromes", Am J Obstet Gynecol., Mar. 2015;212(3): doi: 10.1016/j.ajog.2014.11.041. Epub Dec. 2, 2014, 332.e1-332.e9.
Whitlam, J. B. et al., "Diagnostic application of kidney allograft-derived absolute cell-free DNA levels during transplant dysfunction", Am J Transplant, vol. 19, 2019, 1037-1049.

(56) References Cited

OTHER PUBLICATIONS

Wilkins, et al., "IMP PCR primers detect single nucleotide polymorphisms for Anopheles gambiae species identification, Mopti and Savanna rDNA types, and resistance to dieldrin in Anopheles arabiensis", Malar J., Dec. 1, 20069;5:125., 7 pages.
Wood, et al., "Molecular histology of lung cancer: From targets to treatments", Cancer Treatment Reviews, vol. 41, 2015, 361-375.
Woude, et al., "Methods of identifying drugs with selective effects against cancer cells", Oct. 7, 1997, Nucleic acid sequence search reports AC: 151794, Accession I51796., 2 Pages.
Xie, et al., "Designing highly multiplex PCR primer sets with Simulated Annealing Design using Dimer Likelihood Estimation (SADDLE )", Nat Commun., 2022, 1881.
Yamada, et al., "Detection of K-ras gene mutations in plasma DNA of patients with pancreatic adenocarcinoma: correlation with clinicopathological features", Clin Cancer Res., Jun. 1998;4(6), 1527-1532.
Yamauchi Medical Clinic, "Chromosome abnormality", http://www.yamauchi-iin.com/kaisetu/1241.htm, (Dec. 10, 2015 updated), Dec. 10, 2015, 3 pages.
Ye, et al., "Primer-BLAST: a tool to design target-specific primers for polymerase chain reaction", BMC Bioinformatics, 13:134, 2012, 11 pages.
Yi, et al., "PCR/LDR/capillary electrophoresis for detection of single-nucleotide differences between fetal and maternal DNA in maternal plasma", Prenat Diagn., Mar. 2009;29(3): doi: 10.1002/pd.2072., 217-222.
Zangwill, et al., "Effect of endomyocardial biopsy on levels of donor- specific cell-free DNA", J Heart Lung Transplant, Oct. 2019; 38(10): doi: 10.1016/j.healun.2019.06.005. Epub Jun. 28, 2019, 1118-1120.
Zhang, et al., "A novel multiplex tetra-primer ARMS-PCR for the simultaneous genotyping of six single nucleotide polymorphisms associated with female cancers", PLoS One, Apr. 17, 2013;8(4):e62126. doi: 10.1371/journal.pone.0062126. Print 2013, 8 pages.
Zheng, et al., "Whole-exome sequencing to identify novel somatic mutations in squamous cell lung cancers", International Journal of Oncology, vol. 43, 2015, 755-764.
Vargas, D. Y. et al., "Multiplex Real-Time PCR Assays that Measure the Abundance of Extremely Rare Mutations Associated with Cancer", PLOS One, vol. 11, No. 5, May 31, 2016, 26 pgs.
"European Application No. 014198110, European Search Report Mailed Apr. 28, 2015, 3 pages."
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010), 3 pages.
"Abstracts for CNAPS III Circulating Nucleic Acids in Plasma and Serum and Serum Proteomics", Clinical Chemistry, vol. 49, No. 11, 2003, 33 pages.
"Abstracts for CNAPS IV Circulating Nucleic Acids in Plasma/Serum", Fourth International Conference on Circulating Nucleic Acids in Plasma/Serum (CNAPS-IV), 2005, 40 pages.
"How Many Carbs in a Potato?, [Online]", New Health Guide, Nov. 1, 2014, 3 pages.
"Random variable", The Penguin Dictionary of Mathematics, 2008, 1 page.
Abaan, O. D. et al., "The Exomes of the NCI-60 Panel: A Genomic Resource for Cancer Biology and Systems Pharmacology", Cancer Res., vol. 73, No. 14, Jul. 15, 2013, 4372-4382.
Abbosh, C. et al., "Phylogenetic ctDNA analysis depicts early-stage lung cancer evolution", NATURE, vol. 545, May 25, 2017, 446-451.
Abd-Elsalam, Kamel A. , "Bioinformatic Tools and Guideline for PCR Primer Design", African Journal of Biotechnology, vol. 2, 2003, pp. 91-95.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Academic Press, "Fixed Medium", 1996, 1 pg.
Adalsteinsson, V. A. et al., "Scalable whole-exome sequencing of cell-free DNA reveals high concordance with metastatic tumors", Nature Communications, vol. 18, No. 1324, 2017, 13 pages.
Adinolfi, M. et al., "Rapid Detection of Aneuploidies by Microsatellite and the Quantitative Fluorescent Polymerase Chain Reaction", Prenatal Diagnosis, vol. 17, No. 13, 1997, 1299-1311.
Agarwal, Ashwin. et al., "Commercial Landscape of Noninvasive Prenatal Testing in the United States", Prenatal Diagnosis, 33, 2013, 521-531.
Agbor-Enoh, S. et al., "Donor-derived cell-free DNA predicts allograft failure and mortality after lung transplantation", EBioMedicine, vol. 40, 2019, 541-553.
Alaeddini, R. et al., "Forensic implications of genetic analyses from degraded DNA—A review", Forensic Science International: Genetics, vol. 4, 2010, 148-157.
Alberts, B. et al., "Chapter 20: Germ Cells and Fertilization", Molecular Biology of the Cell, Fourth Edition, 2002, 1127-1156.
Alberts, B. et al., "Chapter 4: Dna and Chromosomes", Molecular Biology of the Cell, Fourth Edition, 2002, 191-234.
Alizadeh, Mehdi et al., "Quantitative Assessment of Hematopoietic Chimerism after Bone Marrow Transplantation by Real-time Quantitative Polymerase Chain Reaction", Blood, vol. 99, No. 12, Jun. 15, 2002, 4618-4625.
Alkan, Can et al., "Personalized Copy Number and Segmental Duplication Maps Using Next-Generation Sequencing", Nature Genetics, 41, 10, 2009, 1061-1068.
Allaire, F R. , "Mate selection by selection index theory", Theoretical Applied Genetics, 57(6), 1980, 267-272.
Allan, J. et al., "Micrococcal Nuclease Does Not Substantially Bias Nucleosome Mapping", Journal of Molecular Biology, vol. 417, Jan. 30, 2012, 152-164.
Allawi, Hatim T. et al., "Thermodynamics of internal C.T Mismatches in DNA", Nucleic Acids Research, 26 (11), 1998, 2694-2701.
Ambardar, S. et al., "High Throughput Sequencing: An Overview of Sequencing Chemistry", Indian J. Microbiol., vol. 56, No. 4, 2016, 394- 404.
Amicucci, P. et al., "Prenatal Diagnosis of Myotonic Dystrophy Using Fetal DNA Obtained from Maternal Plasma", Clinical Chemistry, vol. 46, No. 2, 2000, 301-302.
Andras, S. C. et al., "Strategies for Signal Amplification in Nucleic Acid Detection", Molecular Biotechnology, vol. 19, 2001, 29-44.
Anker, P. et al., "Circulating DNA in Plasma or Serum", Medicina, vol. 60, 2000, 699-702.
Anker, P. et al., "Detection of circulating tumour DNA in the blood (plasma/serum) of cancer patients", Cancer and Metastasis Reviews, vol. 18, 1999, 65-73.
Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.
Ansorge, Wilhelm J. , "Next-generation DNA Sequencing Techniques", New Biotechnology, vol. 25, No. 4, Feb. 2, 2009, 195-203.
Antonarakis, S. E. et al., "Chromosome 21 and Down Syndrome: From Genomics to Pathophysiology", Nature Reviews Genetics, vol. 5, Oct. 2004, 725-738.
Aoki, Yasuhiro , "Statistical and Probabilistic Bases of Forensic DNA Testing", The Journal of the Iwate Medical Association, 2002, vol. 54, p. 81-94.
Arandjelovic, M. et al., "Two-Step Multiplex Polymerase Chain Reaction improves the Speed and Accuracy of Genotyping Using DNA from Noninvasive and Museum Samples", Molecular Ecology Resources, vol. 9, 2009, pp. 28-36.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.

(56) References Cited

OTHER PUBLICATIONS

Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Auld, D. S. , "Use of Chelating Agents to Inhibit Enzymes", Methods in Enzymology, vol. 158, 1988, 110-114.
Avent, Neil D. et al., "Cell-free Fetal DNA in The Maternal Serum And Plasma: Current And Evolving Applications", Current Opinion in Obstretrics and Gynecology, vol. 21, No. 2, Apr. 1, 2009, 175-179.
Avgidou, K. et al., "Prospective first-trimester screening for trisomy 21 in 30,564 pregnancies", American Journal of Obstetrics and Gynecology, vol. 192, 2005, 1761-1767.
Ayala, et al., "Long-Term Follow-Up of Donor Chimerism Tolerance After Human Liver Transplantation", Liver Transplantation, vol. 15, No. 6,, May 28, 2009, 581-591.
Bada, Michael A. et al., "Computational Modeling of Structural Experimental Data", Methods in Enzymology,317, 2000, 470-491.
Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.
Balavoine, Guillaume , "Identification of Members of Several Homeobox Genes in a Planarian Using a Ligation-Mediated Polymerase Chain Reaction Technique", Nucleic Acids Research, vol. 24, 1996, pp. 1547-1553.
Balduini, et al., "Utility of Biochemical Markers in The Follow-up Heart Transplant Recipients", Transplantation Proceedings, vol. 35, No. 8, Dec. 1, 2003, 3075-3078.
Bale, J. R. et al., "Reducing Birth Defects: Meeting the Challenge in the Developing World", Institute of Medicine of the National Academies, 2003, 270 pgs.
Ballif, B. C. et al., "Detection of Low-Level Mosaicism by Array CGH in Routine Diagnostic Specimens", American Journal of Medical Genetics Part A, vol. 140A, 2006, 2757-2767.
Banfi, G. et al., "The role of ethylenediamine tetraacetic acid (EDTA) as in vitro anticoagulant for diagnostic purposes", Clin. Chem., vol. 45, No. 5, 2007, 565-576.
Barbazuk, et al., "SNP Discovery via 454 Transcriptome Sequencing", The Plant Journal, vol. 51, Jul. 27, 2007, 910-918.
Barra, G. B. et al., "EDTA-mediated inhibition of DNases protects circulating cell-free DNA from ex vivo degradation in blood samples", Clinical Biochemistry, vol. 48, 2015, 976-981.
Barski, A. et al., "High-Resolution Profiling of Histone Methylations in the Human Genome", Cell, vol. 129, May 18, 2007, 823-837.
Bartlett, John M. et al., "PCR Protocols", PCR Protocols, vol. 226, 2003, 519 pages.
Bashashati, A. et al., "Distinct evolutionary trajectories of primary high-grade serous ovarian cancers revealed through spatial mutational profiling", Journal of Pathology, vol. 231, 2013, 21-34.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter, L. L. et al., "Discovery and genetic localization of Down syndrome cerebellar phenotypes using the Ts65Dn mouse", Human Molecular Genetics, vol. 9, No. 2, Jan. 2000, 195-202.
Baxter-Lowe, et al., "Tracking Microchimeric DNA in Plasma to Diagnose and Manage Organ Transplant Rejection", Clinical Chemistry, vol. 52, No. 4, Apr. 1, 2006, 559-561.
Beaumont, Mark A et al., "The Bayesian Revolution in Genetics", Nature Reviews Genetics, 5, 2004, 251-261.
Beck, et al., "Next Generation Sequencing of Serum Circulating Nucleic Acids from Patients with Invasive Ductal Breast Cancer Reveals Differences to Healthy and Nonmalignant Controls", Molecular Cancer Research, vol. 8, No. 3, Mar. 1, 2010, 335-342.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
Beck, J. et al., "Profile of the Circulating DNA in Apparently Healthy Individuals", Clinical Chemistry, vol. 55, No. 4, 2009, 730-738.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Belostotsky, Dmitry A. et al., "Plant Systems Biology", Methods in Molecular Biology, vol. 553, Aug. 25, 2009, 3-408.
Bender, et al., "A Multiplex SNP Typing Approach for the DNA Pyrosequencing Technology", International Congress Series, vol. 1288, Apr. 20, 2006, 73-75.
Benjamini, Y. et al., "Controlling the False Discovery Rate: A Practical and Powerful Approach to Multiple Testing", Journal of the Royal Statistical Society, Series B (Methodological), vol. 57, No. 1, 1995, 289-300.
Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bennett, S. T. et al., "Toward the $1000 human genome", Pharmacogenomics, vol. 6, No. 4, 2005, 373-382.
Bentley, et al., "High-resolution, High-throughput HLA Genotyping by Next-generation Sequencing", Tissue Antigens, vol. 74, No. 5, Nov. 1, 2009, 393-403.
Bentley, David R et al., "Accurate Whole Human Genome Sequencing Using Reversible Terminator Chemistry", Nature, 456, 6, 2008, 53-59.
Bergen, A. W. et al., "Effects of DNA mass on multiple displacement whole genome amplification and genotyping performance", BMC Biotechnology, vol. 5, No. 24, Sep. 16, 2005, 11 pgs.
Bermudez, M. et al., "Single-cell sequencing and mini-sequencing for preimplantation genetic diagnosis", Prenatal Diagnosis, 23, 2003, 669-677.
Beroud, C. et al., "Prenatal diagnosis of spinal muscular atrophy by genetic analysis of circulating fetal cells", The Lancet, vol. 361, Mar. 22, 2003, 1013-1014.
Bevinetto, Gina , Bevinetto (5 Foods All Pregnant Women Need, American Baby, available at http://www.parents.com/pregnancy/mybody/nutrition/5greatpregnancyfoods/, Apr. 15, 2008), 8 pgs.
Bianchi, D W. et al., "Fetal gender and aneuploidy detection using fetal cells maternal blood: analysis of NIFTY I data", Prenat Diagn 2002; 22, 2002, 609-615.
Bianchi, D W. et al., "Insights Into Fetal and Neonatal Development Through Analysis of Cell-Free RNA in Body Fluids", Early Human Development, vol. 86, No. 11, Nov. 2010, 747-752.
Bianchi, D. W. , "Circulating Fetal DNA: Its Origin and Diagnostic Potential—A Review", Placenta, vol. 25, Supplemental A, May 2004, S93-S101.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Bianchi, D. W. , "Review: Fetal Cells in the Maternal Circulation: Feasibility for Prenatal Diagnosis", British Journal of Haematology, vol. 105, 1999, 574-583.
Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.

(56) References Cited

OTHER PUBLICATIONS

Bischoff, F. Z. et al., "Cell-free fetal DNA in maternal blood: kinetics, source and structure", Human Reproduction Update, vol. 11, No. 1, 2005, 59-67.
Bischoff, F. Z. et al., "Intact fetal cells in maternal plasma: are they really there?", Lancet, vol. 361, 2003, 139-140.
Bisignano, et al., "PGD and Aneuploidy Screening for 24 Chromosomes: Advantages and Disadvantages of Competing Platforms", Reproductive BioMedicine Online, 23, 2011, 677-685.
Blomquist, T M. et al., "Targeted RNA-Sequencing with Competitive Multiplex- PCR Amplicon Libraries", Plos One, vol. 8, Issue 11, Nov. 2013, 14 pages.
Blow, N. , "The personal side of genomics", Nature, vol. 449, Oct. 4, 2007, 627-630.
Board, R.E. et al., "Detection of BRAF mutations in the tumour and serum of patients enrolled in the AZD6244 (ARRY-142886) advanced melanoma phase II study", British Journal of Cancer, vol. 101, 2009, 1724 - 1730.
Bodenreider, O. , "The Unified Medical Language System (UMLS): Integrating Biomedical Terminology", Nucleic Acids Research, 32, (Database issue), 2004, D267-D270.
Bordoni, et al., "Evaluation of Human Gene Variant Detection in Amplicon Pools by the GS-FLX Parallel Pyrosequencer", BMC Genomics, vol. 9, Oct. 8, 2008, 1-8.
Boudsocq, F. et al., "Sulfolobus solfataricus P2 Dna polymerase IV (Dpo4): an archael DinB-like DNA polymerase with lesion-bypass properties akin to eukaryotic poln", Nucleic Acids Research, vol. 29, No. 22, 2001, 4607-4616.
Bouma, B. N. et al., "Human Blood Coagulation Factor", The Journal of Biological Chemistry, vol. 252, No. 18, 1977, 6432-6437.
Brastianos, P. K. et al., "Genomic Characterization of Brain Metastases Reveals Branched Evolution and Potential Therapeutic Targets", Cancer Discovery, vol. 5, Sep. 26, 2015, 1164-1177.
Breithaupt, Holger , "The Future of Medicine", EMBO Reports, 21(61), 2001, 465-467.
Brinza, D. et al., "2SNP: scalable phasing based on 2-SNP haplotypes", Bioinformatics, vol. 22, No. 3, 2006, 371-373.
Brockman, et al., "Quality Scores and SNP Detection in Sequencing-by-synthesis Systems", Genome Research, vol. 18, No. 5, May 1, 2008, 763-770.
Broude, N E. et al., "High-Level Multiplex DNA Amplification", Antisense & Nucleic Acid Drug Development, vol. 11, 2001, 327-332.
Broude, N. E. et al., "High Multiplexity PCR Based on PCR Suppression", DNA Amplification Current Technologies and Applications, 2004, 61-76.
Broude, N. E. et al., "Multiplex Allele-specific Target Amplification based on PCR Suppression", PNAS, vol. 98, No. 1, Jan. 2, 2001, 206-211.
Brownie, Jannine et al., "The Elimination of Primer-Dimer Accumulation in PCR", Nucleic Acids Research, 25(16), 1997, 3235-3241.
Browning, S. R. et al., "Rapid and Accurate Haplotype Phasing and Missing-Data Inference for Whole-Genome Association Studies By Use of Localized Haplotype Clustering", The American Journal of Human Genetics, vol. 81, Nov. 2007, 1084-1097.
Bryant, A. P., "Terminology of Sugars", Ind. Eng. Chem., vol. 26, No. 2, 1933, 231.
Burkey, B. F. et al., "Hepatic apolipoprotein J is secreted as a lipoprotein", Journal of Lipid Research, vol. 33, 1992, 1517-1526.
Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.
Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.
Bustamante- Aragones, Ana et al., "New Strategy for The Prenatal Detection/Exclusion of Paternal Cystic Fibrosis Mutations in Maternal Plasma", Journal of Cystic Fibrosis, vol. 7, Issue 6, Nov. 1, 2008, 505-510.
Butler, et al., "Cardiovascular Magnetic Resonance in the Diagnosis of Acute Heart Transplant Rejection: A Review", Journal of Cardiovascular Magnetic Resonance, vol. 11, No. 1, Mar. 12, 2009, 1-11.
Butler, J. et al., "The Development of Reduced Size STR Amplicons as Tools for Analysis of Degraded DNA*", Journal of Forensic Sciences, vol. 48, No. 5, 2003, 1054-1064.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela , "Multiplex PCR and Emerging Technologies for the Detection of Respiratory Pathogens", Clinical Infectious Diseases, 52(4), 2011, S326-S330.
Calin, G. A. et al., "A MicroRNA Signature Associated with Prognosis and Progression in Chronic Lymphocytic Leukemia", N Engl J Med, vol. 353, 2005, 1793-1801.
Campbell, P. J. et al., "Subclonal phylogenetic structures in cancer revealed by ultra-deep sequencing", PNAS, vol. 105, No. 35, Sep. 2, 2008, 13081-13086.
Canick, J. A. et al., "The impact of maternal plasma DNA fetal fraction on next generation sequencing tests for common fetal aneuploidies", Prenatal Diagnosis, vol. 33, 2013, 667-674.
Cansar, , "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.
Cao, Y. et al., "Clinical Evaluation of Branched DNA Signal Amplification for Quantifying HIV Type 1 in Human Plasma", AIDS Research and Human Retroviruses, vol. 11, No. 3, 1995, 353-361.
Carnevale, Alessandra et al., "Attitudes of Mexican Geneticists Towards Prenatal Diagnosis and Selective Abortion", American Journal of Medical Genetics, 75, 1998, 426-431.
Carvalho, B. et al., "Exploration, normalization, and genotype calls of high-density oligonucleotide SNP array data", Biostatistics, vol. 8, No. 2, 2007, 485-499.
Casbon, J. A. et al., "A method for counting PCR template molecules with application to next-generation sequencing", Nucleic Acids Research, vol. 39, No. 12, Apr. 13, 2011, 1-8.
Castleberry, C. D. et al., "Quantification of Circulating Cell—Free DNA in Pediatric Heart Transplant Recipients", Journal of Heart and Lung Transplantation, vol. 30, No. 4, Apr. 1, 2011, S139.
Chakraborty, R. et al., "Paternity Exclusion by DNA Markers: Effects of Paternal Mutations", Journal of Forensic Sciences, vol. 41, No. 4, Jul. 1996, 671-677.
Chan, Allen K. et al., "Cell-free Nucleic Acids In Plasma, Serum And Urine: A New Tool in Molecular Diagnosis", Annals of Clinical Biochemistry, vol. 40, Issue 2, Mar. 1, 2003, 122-130.
Chan, K.C. et al., "Size Distributions of Maternal and Fetal DNA in Maternal Plasma", Clinical Chemistry, vol. 50, No. 1, 2004, 88-92.
Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.
Chavali, Sreenivas et al., "Oligonucleotide Properties Determination And Primer Designing: A Critical Examination of Predictions", Bioinformatics, vol. 21, 2005, pp. 3918-3925.
Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.
Chen, Bing-Yuan et al., "PCR Cloning Protocols", PCR Cloning Protocols, vol. 192, 2002, 434 pages.
Chen, C. P. et al., "Fetal DNA in maternal plasma: the prenatal detection of a paternally inherited fetal aneuploidy", Prenatal Diagnosis, vol. 20, 2000, 353-357.

(56) References Cited

OTHER PUBLICATIONS

Chen, X. Q. et al., “Microsatallite alterations in plasma DNA of small cell lung cancer patients”, Nature Medicine, vol. 2, No. 9, Sep. 1996, 1033- 1035.
Chetty, Shilpa et al., “Uptake of Noninvasive Prenatal Testing (NIPT) in Women Following Positive Aneuploidy Screening”, Prenatal Diagnosis,33, 2013, 542-546.
Cheung, S. W. et al., “Rapid Publication: Microarray-Based CGH Detects Chromosomal Mosaicism Not Revealed by Conventional Cytogenetics”, American Journal of Medical Genetics Part A, vol. 143A, 2007, 1679-1686.
Cheung, V. G. et al., “Whole genome amplification using a degenerate oligonucleotide primer allows hundreds of genotypes to be performed on less than one nanogram of genomic DNA”, Proceedings of the National Academy of Sciences, USA, vol. 93, Dec. 1996, 14676-14679.
Chim, S. S. et al., “Detection and Characterization of Placental MicroRNAs in Maternal Plasma”, Clinical Chemistry, vol. 54, No. 3, 2008, 482-490.
Chinnapapagari, S. K. et al., “Treatment of Maternal Blood Samples with Formaldehyde Does Not Alter the Proportion of Circulatory Fetal Nucleic Acids (DNA and mRNA) in Maternal Plasma”, Clinical Chemistry, vol. 51, No. 3, 2005, 653-655.
Chitty, L. S. et al., “Noninvasive Prenatal Screening for Genetic Diseases Using Massively Parallel Sequencing of Maternal Plasma DNA”, Cold Spring Harbor Perspectives in Medicine, vol. 5, No. 9, 2015, 20 pages.
Chiu, R. et al., “Non-Invasive Prenatal Assessment of Trisomy 21 by Multiplexed Maternal Plasma DNA Sequencing: Large Scale Validity Study”, BMJ, 342, c7401, 2011, 9 pgs.
Chiu, R.W.K. et al., “Hypermethylation of RASSF1A in Human and Rhesus Placentas”, The American Journal of Pathology, vol. 170, No. 3, Mar. 2007, 941-950.
Chiu, Rossa W. et al., “Effects of Blood-Processing Protocols on Fetal and Total DNA Quantification in Maternal Plasma”, Clinical Chemistry, 47(9), 2001, 1607-1613.
Chiu, Rossa W.K. et al., “Maternal Plasma DNA Analysis with Massively Parallel Sequencing by Litigation for Noninvasive Prenatal Diagnosis of Trisomy 21”, Clinical Chemistry, 56, 3, 2010, 459-463.
Chiu, Rossa W.K. et al., “Non-Invasive Prenatal Diagnosis by Single Molecule Counting Technologies”, Trends in Genetics, 25 (7), 2009, 324-331.
Chiu, Rossa W.K. et al., “Noninvasive Prenatal Diagnosis of Fetal Chromosomal Aneuploidy by Massively Parallel Genomic Sequencing of DNA in Maternal Plasma (with Supporting Information)”, PNAS, vol. 105, No. 51, 2008, 20458-20463.
Choi, M. et al., “Genetic diagnosis by whole exome capture and massively parallel DNA sequencing”, PNAS, vol. 106, No. 45, Nov. 10, 2009, 19096-19101.
Choi, Y. et al., “Comparison of phasing strategies for whole human genomes”, PLOS Genetics, Apr. 5, 2018, 26 pages.
Chu, T. et al., “Statistical Considerations for Digital Approaches to Non-Invasive Fetal Genotyping”, Bioinformatics (Advance Access publication), 26 (22), 2010, 2863-2866.
Chu, Tianjiao et al., “Statistical Model for Whole Genome Sequencing and its Application to Minimally Invasive Diagnosis of Fetal Genetic Disease”, Bioinformatics, 25(10), 2009, 1244-1250.
Chu, Tianjiao et al., “A Novel Approach Toward the Challenge of Accurately Quantifying Fetal DNA in Maternal Plasma”, Prenatal Diagnosis,30, 2010, 1226-1229.
Chung, G. T. et al., “Lack of Dramatic Enrichment of Fetal DNA in Maternal Plasma by Formaldehyde Treatment”, Clinical Chemistry, vol. 51, No. 3, 2005, 655-658.
Church, et al., “Multiplex DNA Sequencing”, Science, vol. 240, No. 4849, Apr. 8, 1988, 185-188.
Ciriello, G. et al., “Emerging landscape of oncogenic signatures across human cancers”, Nature Genetics, vol. 45, No. 10, Oct. 2013, 1127-1135.
Clausen, F. B. et al., “Improvement in fetal DNA extraction from maternal plasma. Evaluation of the NucliSens Magnetic Extraction system and the QIAamp DSP Virus Kit in comparison with the QIAamp DNA Blood Mini Kit”, Prenatal Diagnosis, vol. 27, 2007, 6-10.
Cole, Neal W. et al., “Hyperglycemia-Induced Membrane Lipid Peroxidation and Elevated Homocysteine Levels Are Poorly Attenuated by Exogenous Folate in Embryonic Chick Brains”, Comparative Biochemistry and Physiology, Part B, 150, 2008, 338-343.
Colella, S. et al., “QuantiSNP: an Objectives Bayes Hidden-Markov Model to Detect and Accurately Map Copy Number Variation Using SNP Genotyping Data”, Nucleic Acids Research, 35 (6), 2007, 2013-2025.
Conlin, L. K. et al., “Mechanisms of mosaicism, chimerism and uniparental disomy identified by single nucleotide polymorphism array analysis”, Human Molecular Genetics, vol. 19, No. 7, Jan. 6, 2010, 1263-1275.
Coombes, R. C. , “Abstract P4-01-02: Early detection of residual breast cancer through a robust, scalable and personalized analysis of circulating tumour DNA (ctDNA) antedates overt metastatic recurrence”, Cancer Research, vol. 79, No. 4 Supplement, Feb. 15, 2019.
Cossu, Gianfranco et al., “Rh D/d Genotyping by Quantitative Polymerase Chain Reaction and Capillary Zone Electrophoresis”, Electrophoresis, 17, 1996, 1911-1915.
Couraud, S. et al., “Noninvasive Diagnosis of Actionable Mutations by Deep Sequencing of Circulating Free DNA in lung Cancer from Never-Smokers: A Proof-of-Concept Study from BioCAST / IFCT-1002”, Clinical Cancer Research, vol. 20, No. 17, Jul. 10, 2014, 4613-4624.
Couraud, S. et al., “Supplementary Data for Noninvasive Diagnosis of Actionable Mutations by Deep Sequencing of Circulating Free DNA in lung Cancer from Never-Smokers: A Proof-of-Concept Study from BioCAST / IFCT-1002”, 2014, 13 pages.
Coyle, J. F. et al., “Standards for detailed clinical models as the basis for medical data exchange and decision support”, International Journal of Medical Informatics, 69(2-3), 2003, 157-174.
Craig, D. W. et al., “Identification of genetic variants using barcoded multiplexed sequencing”, Nature Methods, vol. 5, Oct. 2008, 887-893.
Crespo-Leiro, et al., “Gene Expression Profiling for Monitoring Graft Rejection in Heart Transplant Recipients”, Transplantation Proceedings, vol. 41, No. 6, Jul. 1, 2009, 2240-2243.
Cronn, R. et al., “Multiplex sequencing of plant chloroplast genomes using Solexa sequencing-by-synthesis technology”, Nucleic Acids Research, vol. 36, No. 19, Aug. 27, 2008, 11 pgs.
Cross, Jillian et al., “Resolution of trisomic mosaicism in prenatal diagnosis: estimated performance of a 50K SNP microarray”, Prenat Diagn 2007; 27, 2007, 1197-1204.
Cunningham, K. S. et al., “An approach to endomyocardial biopsy interpretation”, Journal of Clinical Pathology, vol. 59, No. 2, Mar. 2006, 121-129.
Dahl, et al., “Multigene Amplification and Massively Parallel Sequencing for Cancer Mutation Discovery”, Proceedings of the National Academy of Sciences, vol. 104, No. 22, May 29, 2007, 9387-9392.
Dambrin, et al., “A New Rejection Criteria in the Heterotopically Placed Rat Heart By Non-invasive Measurement of DP/DTMAX”, The Journal of Heart and Lung Transplantation, vol. 18, No. 6, Jun. 18, 1999, 524-531.
D'Aquila, Richard et al., “Maximizing sensitivity and specificity of PCR by pre-amplification heating”, Nucleic Acids Research, 19(13), 1991, p. 3749.
Daruwala, Raoul-Sam et al., “A Versatile Statistical Analysis Algorithm to Detect Genome Copy No. Variation”, PNAS, 101(46), 2004, 16292-16297.
Dawson, S.J. et al., “Analysis of Circulating Tumor DNA to Monitor Metastatic Breast Cancer”, The New England Journal of Medicine, vol. 368, No. 13, Mar. 28, 2013, 1199-1209.
De Bruin, E. et al., “Spatial and temporal diversity in genomic instability processes defines lung cancer evolution”, Science, vol. 346, No. 6206, Oct. 10, 2014, 251-256.
De Jong, M. M. et al., “Genes other than BRCA 1 and BRCA2 involved in breast cancer susceptibility”, J. Med. Genet., vol. 39, 2009, 225-242.

(56) References Cited

OTHER PUBLICATIONS

De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research, 23 (22), 1995, 4742-4743.
Deb, Mahua et al., "Development of a Multiplexed PCR Detection Method for Barley and Cereal Yellow Dwarf Viruses, Wheat Spindle Streak Virus, Wheat Streak Mosaic Virus and Soil-Borne Wheat Mosaic Virus", Journal of Virological Methods, vol. 148, 2008, pp. 17-24.
Delaneau, O. et al., "Shape-IT: new rapid and accurate algorithm for haplotype inference", BMC Bioinformatics, vol. 9, No. 540, Dec. 16, 2008, 14 pages.
Delgado, P. O. et al., "Characterization of cell-free circulating DNA in plasma in patients with prostate cancer", Tumor Biol., vol. 34, 983-986, 2013.
Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.
Deutsch, S. et al., "Detection of aneuploidies by paralogous sequence quantification", J Med Genet, vol. 41, 2004, 908-915.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Di, X. et al., "Dynamic model based algorithms for screening and genotyping", Bioinformatics, vol. 21, No. 9, 2005, 1958-1963.
Dias-Santagata, D. et al., "Braf V600E Mutations Are Common in Pleomorphic Xanthoastrocytoma: Diagnostic and Therapeutic Implications", PLoS One, vol. 6, No. 3, Mar. 2011, 9 pages.
Dickover, R. E. et al., "Optimization of Specimen-Handling Procedures for Accurate Quantitation of Levels of Human Immunodeficiency Virus RNA in Plasma by Reverse Transcriptase PCR", Journal of Clinical Microbiology, vol. 36, No. 4, 1998, 1070-1073.
Dieffenbach, C W. et al., "General concepts for PCR primer design", Genome Research. PCR methods and Applications vol. 3, 1993, S30-S37.
Diehl, F. et al., "Circulating mutant DNA to assess tumor dynamics", Nature Medicine, vol. 14, No. 9, Jul. 31, 2008, 985-990.
Diehl, F. et al., "Detection and quantification of mutations in the plasma of patients with colorectal tumors", PNAS, vol. 102, No. 45, Nov. 8, 2005, 16368-16373.
Dietmaier, W. et al., "Multiple Mutation Analyses in Single Tumor Cells with Improved Whole Genome Amplification", American Journal of Pathology, vol. 154, No. 1, Jan. 1999, 83-95.
Ding, C. et al., "Direct molecular haplotyping of long-range genomic DNA with M1-PCR", Pnas 100(13), 2003, 7449-7453.
Ding, C. et al., "MS analysis of single-nucleotide differences in circulating nucleic acids: Application to noninvasive prenatal diagnosis", PNAS, vol. 101, No. 29, Jul. 20, 2004, 10762-10767.
Dodge, Y. , "Bayes' Theorem", The Concise Encyclopedia of Statistics, 2008, 30-31.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na -K+ -Cl-Cotransporter (NKCC1) in Asthmatic Subjects", Genome Res., 11, 2001, 1473-1483.
Donaghue, C. et al., "Detection of mosaicism for primary trisomies in prenatal samples by QF-PCR and karyotype analysis", Prenatal Diagnosis, vol. 25, 2005, 65-72.
Donohoe, Gerard G. et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Doostzadeh, et al., "High Throughput Automated Allele Frequency Estimation by Pyrosequencing", PLoS ONE, vol. 3, No. 7, Jul. 16, 2008, 1-4.
Dorit, D. L. , "cDNA Amplification Using One-sided (Anchored) Pcr", Current Protocols in Molecular Biology, vol. 17, 1992, pp. 15.6.1-15.6.10.
Dorit, Robert L. et al., "One-sided Anchored Polymerase Chain Reaction for Amplification and Sequencing of Complementary DNA", Methods in Enzymology, vol. 218 1993, pp. 36-47.
Dowd, P. et al., "On the mechanism of the anticlotting action of vitamin R quinone", Proc. Natl. Acad. Sci. USA, vol. 92, 1995, 8171-8175.
Downward, J. , "Targeting RAS Signalling Pathways in Cancer Therapy", Nature Reviews, vol. 3, Jan. 2003, 11-22.
Dressman, D. et al., "Transforming single DNA molecules into fluorescent magnetic particles for detection and enumeration of genetic variations", PNAS, vol. 100, No. 15, Jul. 22, 2003, 8817-8822.
Echeverri, et al., "Caffeine's Vascular Mechanisms of Action", International Journal of Vascular Medicine vol. 2010(2010), 10 pages, Aug. 25, 2010.
Edwards, M. C. et al., "Multiplex PCR: Advantages, Development, and Applications", Genome Research, vol. 3, 1994, S65-S75.
Efron, B. et al., "Bootstrap Methods for Standard Errors, Confidence Intervals, and Other Measures of Statistical Accuracy", Statistical Science, vol. 1, No. 1, 1986, 54-77.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H , "Mild Course of Fetal Rh D Haemolytic Disease due to Maternal Alloimmunisation to Paternal HLA Class I and II Antigens", Vox Sang, 68, 1995, 243-247.
Ellison, Aaron M. , "Bayesian Inference in Ecology", Ecology Letters, vol. 7, 2004, 509-520.
Ellonen, P. et al., "Development of SNP Microarray for Supplementary Paternity Testing", International Congress Series, 1261, 2004, 12-14.
Elnifro, Elfath M. , "Multiplex PCR: Optimization and Application in Diagnostic Virology", Clinical Microbiology Reviews, vol. 13, 2000, pp. 559-570.
Eltoukhy, H. et al., "Modeling and Base-Calling for DNA Sequencing-By-Synthesis", IEEE, 2006, II-1032-II-1035.
EP06838311.6, "European Communication and Extended European Search Report", mailed Dec. 30, 2008, 8 pgs.
EP08742125.1, "European Communication pursuant to Article 94(3) EPC and Examination Report", mailed Feb. 12, 2010, 5 pgs.
Erijman, Ariel et al., "Transfer-PCR (TPCR): A Highway For DNA Cloning and Protein Engineering", Journal of Structural Biology, vol. 175, 2011, pp. 171-177.
Erlich, R. L. et al., "Next-generation sequencing for HLA typing of class loci", BMC Genomics, vol. 12, No. 42, 2011, 13 pages.
Eronen, L. et al., "HaploRec: efficient and accurate large-scale reconstruction of haplotypes", BMC Bioinformatics, vol. 7, No. 542, Dec. 22, 2006, 18 pages.
European Commission, , "The 7th International Conference on Circulating Nucleic Acids in Plasma and Serum (CNAPS VII) in Madrid—Spain", The International Conference on Circulating Nucleic Acids in Plasma and Serum, Oct. 24, 2011, 2 pgs.
Everitt, B. S. , "Medical Statistics From A to Z", 2003, 3 pages.
Fackenthal, J. D. et al., "Aberrant RNA splicing and its functional consequences in cancer cells", Disease Models & Mechanisms, vol. 1, 2008, 37-42.
Faham, M. et al., "Deep-sequencing approach for minimal residual disease detection in acute lymphoblastic leukemia", Blood Journal, vol. 120, No. 26, Dec. 20, 2012, 5173-5180.

(56) References Cited

OTHER PUBLICATIONS

Falcon, O. , "Screening for trisomy 21 by fetal tricuspid regurgitation, nuchal translucency and maternal serum free b-hCG and PAPP-A at 11 + 0 to 13 + 6 weeks", Ultrasound Obstet Gynecol, vol. 27, 2006, 151-155.
Fan, et al., "Whole-genome molecular haplotyping of single cells", Nature Biotechnology, vol. 29, No. 1, Jan. 1, 2011, 51-57.
Fan, C H. et al., "Detection of Aneuploidy with Digital Polymerase Chain Reaction", Analytical Chemistry, vol. 79, No. 19, Oct. 1, 2007, 7576-7579.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "In Principle Method for Noninvasive Determination of the Fetal Genome", Nat. Prec., 2010, 16 pgs.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Fan, J.-B. et al., "Highly Parallel SNP Genotyping", Cold Spring Harbor Symposia on Quantitative Biology, vol. LXVIII, Feb. 2003, 69-78.
Fan, Jian-Bing et al., "Highly Parallel Genomic Assay", Nature Reviews, 7, 2006, 632-644.
Fat Secret, "5 Foods to Never Eat", https://www.fatsecret.com/calories-nutrition/food/white-bread/carboyhydrate (printed from internet Nov. 1, 2014)., 2 pages.
Fazio, Gennaro et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Fitzgerald, , "Intravascular Ultrasound Imaging of Coronary Arteries: Is Three Layers The Norm?", Circulation, vol. 86, No. 1, Jul. 1, 1992, 154-158.
Ford, E. et al., "A method for generating highly multiplexed ChIP-seq libraries", BMC Research Notes, vol. 7, No. 312, May 22, 2014, 1-5.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Fortina, P. et al., "Detection of the most common mutations causing beta-thalassemia in Mediterraneans using a multiplex amplification refractory mutation system (MARMS)", Genome Res., vol. 2, 1992, 163-166.
Fortina, P. et al., "DOP-PCR Amplification of Whole Genomic DNA and Microchip-Based Capillary Electrophoresis", Methods in Molecular Biology: Capillary Electrophoresis of Nucleic Acids, vol. II Practical Applications of Capillary Electrophoresis, 2001, 211-219.
Fouquet, C. et al., "Rapid and Sensitive p53 Alteration Analysis in Biopsies from Lung Cancer Patients Using a Functional Assay and a Universal Oligonudeotide Array: A Prospective Study", Clinical Cancer Research, vol. 10, May 15, 2004, 3479-3489.
Fournie, et al., "Plasma DNA as a Marker of Cancerous Cell Death. Investigations in Patients Suffering From Lung Cancer and in Nude Mice Bearing Human Tumours", Cancer Letters, vol. 91, No. 2, May 8, 1995, 221-227.
Fredriksson, et al., "Multiplex amplification of all coding sequences within 10 cancer genes by Gene-Collector", Nucleic Acids Research, 2007, vol. 35, No. 7 e47, 1-6.
Fredriksson, M et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.
Freeman, Jennifer L. et al., "Copy Number Variation: New Insights in Genome Diversity", Genome Research, 16, 2006, 949-961.
Frohman, M A. et al., "On Beyond Classic RACE (Rapid Amplification of cDNA Ends)", Genome Research, vol. 4, 1994, S40-S58.
Frost, Mackenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.
Fu, Yao-Wen et al., "Presence of Donor-and-recipientderived Dna Microchimerism in the Cell-free Blood Samples of Renal Transplantation Recipients Associates With the Acceptance of Transplanted Kidneys", Asian Journal of Andrology, vol. 8, No. 4, Jul. 1, 2006, 477-482.
Gadi, V. K. et al., "Soluble Donor DNA Concentrations in Recipient Serum Correlate with Pancreas-Kidney Rejection", Clinical Chemistry, vol. 52, No. 3, 2006, 379-382.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gao, et al., "Relation of Donor Age and Preexisting Coronary Artery Disease on Angiography and Intracoronary Ultrasound to Later Development of Accelerated Allograft Coronary Artery Disease", The American Journal of Cardiology, vol. 29, No. 3, Mar. 1, 1997, 623-629.
Gao, F. et al., "Characterizing Immunoglobulin Repertoire from Whole Blood by a Personal Genome Sequencer", PLOS One, vol. 8, No. 9, Sep. 13, 2013, 8 pgs.
Gao, Ming et al., "Characterization of dull1, a Maize Gene Coding for a Novel Starch Synthase", The Plant Cell, vol. 10, 1998, pp. 399-412.
Garcia Moreira, V. et al., "Cell-Free DNA as a Noninvasive Acute Rejection Marker in Renal Transplantation", Clinical Chemistry, vol. 55, No. 11, 2009, 1958-1966.
Garcia-Murillas, I. et al., "Mutation tracking in circulating tumor DNA predicts relapse in early breast cancer", Science Translational Medicine, vol. 7, No. 302, Aug. 26, 2015, 34 pgs.
Gardina, P. et al., "Ploidy Status and Copy No. Aberrations in Primary Glioblastomas Defined by Integrated Analysis of Allelic Ratios, Signal Ratios and Loss of Heterozygosity Using 500K Snp Mapping Arrays", BMC Genomics, 9 (489), (doi:10.1186/1471-2164-9-489), 2008, 16 pgs.
Gautier, E. et al., "Fetal RhD genotyping by maternal serum analysis: A two-year experience", American Journal of Obstetrics and Gynecology, vol. 192, 2005, 666-669.

(56) References Cited

OTHER PUBLICATIONS

Geifman- Holtzman, et al., "Prenatal Diagnosis: Update on Invasive Versus Noninvasive Fetal Diagnostic Testing From Maternal Blood", Expert Review of Molecular Diagnostics, vol. 8, No. 6, Nov. 1, 2008, 727-751.
Geiss, G. K. et al., "Direct multiplexed measurement of gene expression with color-coded probe pairs", Nature Biotechnology, vol. 26, No. 3, Feb. 17, 2008, 317-325.
Ghanta, Sujana et al., "Non-Invasive Prenatal Detection of Trisomy 21 Using Tandem Single Nucleotide Polymorphisms", PLoS ONE, 5 (10), 2010, 10 pgs.
Gholami, M. et al., "A tailed PCR procedure for cost-effective, two-order multiplex sequencing of candidate genes in polyploid plants", Plant Biotechnology Journal, vol. 10, 2012, 635-645.
Gielis, E. M. et al., "Cell-Free DNA: An Upcoming Biomarker in Transplantation", American Journal of Transplantation, vol. 15, 2015, 2541-2551.
Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.
Gineikiene, Egle et al., "Single Nucleotide Polymorphism-based System Improves the Applicability of Quantitative PCR for Chimerism Monitoring", Journal of Molecular Diagnostics, vol. 11, No. 1, Jan. 1, 2009, 66-74.
Gingeras, et al., "Fifty Years of Molecular (DNA/RNA) Diagnostics", Clinical Chemistry, vol. 51, No. 3, Jan. 13, 2005, 661-671.
Girnita, Diana M. et al., "Disparate Distribution of 16 Candidate Single Nucleotide Polymorphisms Among Racial and Ethnic Groups of Pediatric Heart Transplant Patients", Transplantation, vol. 82, No. 12, Dec. 27, 2006, 1774-1780.
Gjertson, David W. et al., "Assessing Probability of Paternity and the Product Rule in DNA Systems", Genetica, 96, 1995, 89-98.
Gnirke, A. et al., "Solution hybrid selection with ultra-long oligonucleotides for massively parallel targeted sequencing", Nature Biotechnology, vol. 27, No. 2, Feb. 2009, 182-189.
Go, A. T. et al., "Non-invasive aneuploidy detection using free fetal DNA and RNA in maternal plasma: recent progress and future possibilities", Human Reproduction Update, vol. 17, No. 3, 2011, 372-382.
Goncalves-Primo, A. et al., "Investigation of Apoptosis-Related Gene Expression Levels in Preimplantation Biopsies as Predictors of Delayed Kidney Graft Function", Transplantation, vol. 97, No. 12, Jun. 27, 2014.
Gordon, et al., "Disease-Specific Motifs Can Be Identified in Circulating Nucleic Acids From Live Elk and Cattle Infected With Transmissible Spongiform Encephalopathies", Nucleic Acids Research, vol. 37. No. 2, Feb. 1, 2009, 550-556.
Gorringe, et al., "Large-scale Genomic Analysis of Ovarian Carcinomas", Molecular oncology, vol. 3, No. 2, Apr. 1, 2009, 157-164.
Gouya, et al., "Coronary Artery Stenosis In High-risk Patients: 64-section Ct and Coronary Angiography—Prospective Study and Analysis of Discordance", Radiology, vol. 252, No. 2, Aug. 1, 2009, 377-385.
Greenwalt, T. et al., "The Quantification of Fetomaternal Hemorrhage by an Enzyme-Linked Antibody Test with Glutaraldehyde Fixation", Vox Sang, 63, 1992, 268-271.
Gregory, et al., "Comparison of Sixty-Four-Slice Multidetector Computed Tomographic Coronary Sngiography to Coronary Angiography With Intravascular Ultrasound for the Detection of Transplant Vasculopathy", The American Journal of Cardiology, vol. 98, No. 7, Aug. 4, 2006, 877-884.
Griffiths, A. J. et al., "An Introduction to Genetic Analysis", Sixth Edition, 1996, 5 pages.
Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix S1, Nov. 2016, 890-902.
Grunenwald, H. , "Optimization of Polymerase Chain Reactions", Methods in Biology, vol. 226, 2003, 89-99.
Gu, H. et al., "Diagnostic role of microRNA expression profile in the serum of pregnant women with fetuses with neural tube defects", Journal of Neurochemistry, vol. 122, 2012, 641-649.
Guerra, J. , "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Gunderson, K. L. et al., "A genome-wide scalable SNP genotyping assay using microarray technology", Nature Genetics, vol. 37, No. 5, May 2005, 549-554.
Gundry, C. N. et al., "Base-pair neutral homozygotes can be discriminated by calibrated high-resolution melting of small amplicons", Nucleic Acids Research, vol. 36, No. 10, Apr. 29, 2008, 3401-3408.
Guo, H et al., "A Specific and Versatile Genome Walking Technique", Gene, vol. 381, 2006, 18-23.
Gwee, Pai-Chung et al., "Simultaneous Genotyping of Seven Single-nucleotide Polymorphisms in the Mdr1 Gene by Single-tube Multiplex Minisequencing", Pai-Chung Gwee et al., "Simultaneous Genotyping of Seven Single-nucleotide Polymorphisms in the Mdr1 Gene by Single-tube Multiplex Minisequencing", Clinical chemistry, Apr. 2003, vol. 49, Issue. 3, pp. 672-676., Apr. 1, 2003, 672-676.
Hahn, et al., "Non-invasive Prenatal Diagnostics Using Next Generation Sequencing: Technical, Legal And Social Challenges", Expert Opinion on Medical Diagnostics, vol. 6, No. 6, Nov. 1, 2012, 517-528.
Hahn, S. et al., "Current applications of single-cell PCR", CMLS Cellular and Molecular. Life Sciences, vol. 57, 2000, 96-105.
Hahn, S. et al., "Quantification of Circulating DNA: In the Preparation Lies the Rub", Clinical Chemistry, vol. 47, No. 9, 2001, 1577-1578.
Halford, William P. , "The Essential Prerequisites for Quantitative RT-PCR", Nature Biotechnology, vol. 17, 1999, 1 page.
Hall, M. , "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.
Handley, D. et al., "Noninvasive prenatal chromosomal aneuploidy detection using plasma cell-free nucleic acid", Expert Rev Obstet. Gynecol, vol. 5, No. 5, 2010, 581-590.
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hao, T. B. et al., "Circulating cell-free DNA in serum as a biomarker for diagnosis and prognostic prediction of colorectal cancer", British Journal of Cancer, vol. 111, Aug. 26, 2014, 1482-1489.
Hara, Eiji et al., "Subtractive eDNA cloning using oligo(dT)30-latex and PCR: isolation of eDNA clones specific to undifferentiated human embryonal carcinoma cells", Nucleic Acids Research, 19(25), 1991, 7097-7104.
Hardenbol, P. , "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.

(56) References Cited

OTHER PUBLICATIONS

Hartwell, L. H. et al., "Chapter 11: The Direct Detection of Genotype Distinguishes Individual Genomes", Genetics: From Genes to Genomes, Second Edition, 2004, 371-414.
Hartwell, L. H. et al., "Chapter 13: Chromosomal Rearrangements and Changes in Chromosome Number Reshape Eukaryotic Genomes", Genetics: From Genes to Genomes, Second Edition, 2004, 441-486.
Hattori, M. et al., "The DNA sequence of human chromosome 21", NATURE, vol. 405, May 18, 2000, 311-319.
Hawkins, T. et al., "Whole genome amplification—applications and advances", Current Opinion in Biotechnology, 13, 2002, 65-67.
Hayden, et al., "Multiplex-Ready PCR: A new method for multiplexed SSR and SNP genotyping", BMC Genomics 2008, 9(80), 1-12.
He, QZ et al., "A method for improving the accuracy of non-invasive prenatal screening by cell-free foetal DNA size selection", British Journal of Biomedical science, vol. 75, No. 3, Jul. 2018, 133-138.
Heaton, Paul R. et al., "Heminested PCR Assay for Detection of Six Genotypes of Rabies and Rabies-related Viruses", Journal of Clinical Microbiology, vol. 35, 1997, pp. 2762-2766.
Heidary, M. et al., "The dynamic range of circulating tumor DNA in metastatic breast cancer", Breast Cancer Research, vol. 16, No. 421, 2014, 10 pages.
Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Henegariu, O. et al., "Multiplex PCR: Critical Parameters and Step-by-Step Protocol", Biotechniques, vol. 23, 1997, pp. 504-511.
Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.
Hoberman, Rose et al., "A Probabilistic Approach for SNP Discovery in High-throughput Human Resequencing Data", Genome Research, vol. 19, Jul. 15, 2009, 1542-1552.
Hochberg, et al., "A Novel Rapid Single Nucleotide Polymorphism (SNP)-Based Method for Assessment of Hematopoietic Chimerism After Allogeneic Stem Cell Transplantation", Blood, vol. 101, No. 1, Jan. 1, 2003, 363-369.
Hodges, et al., "Genome-wide In Situ Exon Capture for Selective Resequencing", Nature Genetics, vol. 39, No. 12, Nov. 4, 2007, 1522- 1527.
Hodgkinson, C. L. et al., "Tumorigenicity and genetic profiling of circulating tumor cells in small-cell lung cancer", Nature Medicine, vol. 20, No. 8, Aug. 2014, 897-905.
Hoffmann, Steven et al., "Donor Genomics Influence Graft Events: The Effect of Donor Polymorphisms on Acute Rejection and Chronic Allograft Nephropathy", Kidney International, vol. 66, No. 4, Oct. 1, 2004, 1686-1693.
Hojsgaard, S. et al., "BIFROST—Block recursive models induced from relevant knowledge, observations, and statistical techniques", Computational Statistics & Data Analysis, 19(2), 1995, 155-175.
Hollas, B. et al., "A stochastic approach to count RN A molecules using DNA sequencing methods", Lecture Notes in Computer Science, vol. 2812, 2003, 55-62.
Holleley, et al., "Multiplex Manager 1.0: a Cross-Platform Computer Program that Plans and Optimizes Multiplex PCR" BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Holt, et al., "Detecting SNPS and Estimating Allele Frequencies in Clonal Bacterial Populations by Sequencing Pooled DNA", Bioinformatics, vol. 25, No. 16, Aug. 15, 2009, 2074-2075.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Horai, et al., "Novel Implantable Device to Detect Cardiac Allograft Rejection", Circulation, vol. 120, No. Suppl 1, Sep. 15, 2009, 185-190.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Hosmillo, Myra D. et al., "Development of Universal SYBR Green Real-time RT-PCR for the Rapid Detection and Quantitation of Bovine and Porcine Toroviruses", Journal of Virological Methods, vol. 168, 2010, pp. 212-217.
Hosono, S. et al., "Unbiased Whole-Genome Amplification Directly From Clinical Samples", Genome Research, vol. 13, 2003, 954-964.
Hospital, F. et al., "A General Algorithm to Compute Multilocus Genotype Frequencies Under Various Mating Systems" vol. 12, No. 6, Jan. 1, 1996 (Jan. 1, 1996), pp. 455-462.
Hou, X. et al., "Analysis of the Repertoire Features of TCR Beta Chain CDR3 in Human by High-Throughput Sequencing", Cellular Physiology and Biochemistry, vol. 39, Jul. 21, 2019, 651-667.
Howie, et al., "Fast and accurate genotype imputation in genome-wide association studies through pre-phasing", Nature Genetics, vol. 44, No. 8, Jul. 22, 2012, 955-959.
Howie, B. N. et al., "A Flexible and Accurate Genotype Imputation Method for the Next Generation of Genome-Wide Association Studies", PLOS Genetics, vol. 5, No. 6, Jun. 2009, 15 pages.
Hu, Dong Gui et al., "Aneuploidy Detection in Single Cells Using DNA Array-Based Comparative Genomic Hybridization", Molecular Human Reproduction, 10(4), 2004, 283-289.
Hu, Hao et al., "Mutation Screening in 86 Known X-linked Mental Retardation Genes by Droplet-based Multiplex Pcr and Massive Parallel Sequencing", Hao Hu. et al., "Mutation Screening in 86 Known X-linked Mental Retardation Genes by Droplet-based Multiplex Pcr and Massive Parallel Sequencing", Hugo J, Dec. 2009, vol. 3, pp. 41-49., Dec. 1, 2009, 41-49.
Hu, Y. et al., "Detection of Extrahepatic Hepatitis C Virus Replication by a Novel, Highly Sensitive, Single-Tube Nested Polymerase Chain Reaction", Am. J. Clin Pathol., vol. 119, 2003, 95-100.
Huang, D. J. et al., "Reliable detection of Trisomy 21 using MALDI-TOF mass spectrometry", Genetics in Medicine, vol. 8, Nov. 2006, 728-734.
Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.
Huang, J. et al., "Whole genome DNA copy number changes identified by high density oligonucleotide arrays", Human Genomics, vol. 1, No. 4, May 2004, 287-299.
Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593- 1595.
Hug, H. et al., "Measurement of the No. of molecules of a single mRNA species in a complex mRNA preparation", J. Theor. Biol., vol. 221, 2003, 615-624.
Hultin, E. et al., "Competitive enzymatic reaction to control allele-specific extensions", Nucleic Acids Research, vol. 33, No. 5, Mar. 14, 2005, 1-10.
Hung, E.C.W. et al., "Detection of circulating fetal nucleic acids: a review of methods and applications", J. Clin. Pathol., vol. 62, 2009, 308-313.
Hyndman, D L. et al., "PCR Primer Design", Methods in Molecular Biology, vol. 226, Second Edition, 2003, 81-88.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina, "Automated GoldenGate™ Genotyping on the BeadStation 500", Pub. No. 970-2004-002, 2004, 2 pages.

(56) References Cited

OTHER PUBLICATIONS

Illumina, "Genomic Sequencing", Data Sheet: Sequencing, 2010, 38939-38944.
Illumina, "GoldenGate" Assay Workflow: Illumina's GoldenGate assay protocol provides high-quality, high-multiplex genotyping results with a streamlined workflow, Pub. No. 370-2004-006, 2004, 2 pages.
Illumina, "HiSeq 2500 Sequencing System", System Specification Sheet: Sequencing, available via URL https://www.illumina.com/documents/products/datasheets/datasheet_hiseq2500.pdf, 2015, 4 pgs.
Illumina, "History of Sequencing by Synthesis", https://www.illumina.com/science/technology/next-generation-sequencing/illumina-sequencing-history.html, 2020, 3 pages.
Illumina, "Illumina Extends BeadArray Technology to Address Wider Range of SNP Genotyping Projects; New Microarray Offerings Enable Genotyping at 384 and 786 Multiplex", Businesswire, May 4, 2004, 2 pages.
Illumina, "Illumina® Beadstation 500: A Scalable System That Grows With Your Research Requirements", Pub. No. 970-2005-003, Jul. 1, 2005, 4 pages.
Illumina, "Illumina Announces Benchtop SNP Genotyping System", Press Release, Nov. 5, 2003, 3 pages.
Illumina, "Illumina Begins Shipment of BeadStation 500G Benchtop Genotyping System", Press Release, Apr. 15, 2004, 3 pages.
Illumina, "MiSeq System Information Sheet", 2018, 3 pgs.
Illumina, "Patent Owner Illumina's Preliminary Response to Petition", Oct. 17, 2018, 75 pgs.
Illumina, "Petition for Inter Partes Review of U.S. Pat. No. 8,682,592", Jun. 13, 2019, 91 pages.
Illumina, "Plaintiff/Counterclaim Defendant Illumina, Inc.'S Amended Patent L.R. 3-3 Preliminary Invalidity Contentions for U.S. Pat. No. 8,682,592", Oct. 30, 2018, 22 pages.
Illumina, "Plaintiff/Counterclaim-Defendant Illumina, Inc.'S Patent L.R. 3-3 Contentions for U.S. Patent Preliminary Invalidity Contentions for U.S. Pat. No. 8,682,592", Oct. 9, 2018, 81 pages.
Illumina, "Preparing Samples for Sequencing Genomic DNA", Part # 11251892 Rev. A, 2007, 18 pages.
Illumina, "Preparing Samples for Sequencing Genomic DNA", Part # 1003806 Rev. A, 2007, 20 pages.
Illumina, "Products & Services", Product Literature, Mar. 21, 2007, 3 pages.
Illumina, "Technology: Solexa Sequencing Technology", May 21, 2007, 1 page.
Illumina, "TruSeq™ RNA and DNA Library Preparation Kits v2", Data Sheet: Illumina® Sequencing, 2014, 4.
Illumina Catalog, "Paired-End Sample Preparation Guide, Illumina Catalog# PE-930-1 001, Part# 1005063 Rev. E", 2011, 1-40.
Illumina, Inc., "Declaration of David Peters, Ph.D. in Support of Petition for Inter Partes Review of U.S. Pat. No. 8,682,592", Jun. 13, 2019, 136 pages.
*Illumina, Inc.* v. *Natera, Inc.*, "Order Re: Claim Construction", Jan. 30, 2019, 16 pgs.
Imielinski, M. et al., "Mapping the Hallmarks of Lung Adenocarcinoma with Massively Parallel Sequencing", Cell, vol. 150, Sep. 14, 2012, 1107-1120.
Ingman, et al., "SNP Frequency Estimation Using Massively Parallel Sequencing of Pooled DNA", European Journal of Human Genetics, vol. 17, No. 3, Oct. 15, 2008, 383-386.
Innan, H. et al., "The Pattern of Polymorphism on Human Chromosome 21", Genome Research, vol. 13, 2003, 1158-1168.
Interewicz, B. et al., "DNA Released from Ischemic and Rejecting Organs as an Indicator of Graft Cellular Damage", Annals of Transplantation, vol. 9, No. 2, May 1, 2004, 42-45.
International Human, Genome Sequencing Consortium , "Finishing the Euchromatic Sequence of the Human Genome", Nature, vol. 431, Oct. 21, 2004, 931-945.
Ishii, et al., "Optimization of Annealing Temperature to Reduce Bias Caused by a Primer Mismatch in Multitemplate PCR", Applied and Environmental Microbiology, Aug. 2001, p. 3753-3755.
Iskow, R. C. et al., "Natural Mutagenesis of Human Genomes by Endogenous Retrotransposons", Cell, vol. 141, Jun. 25, 2010, 1253-1261.
Ivanov, M. et al., "Non-random fragmentation patterns in circulating cell-free DNA reflect epigenetic regulation", BMC Genomics, vol. 16 (Suppl 13):S1, Jun. 2015, 12 pgs.
Jabara, C. B. et al., "Accurate sampling and deep sequencing of the HIV-1 protease gene using a Primer ID", PNAS, vol. 108, No. 50, Dec. 13, 2011, 20166-20171.
Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.
Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.
Jamal-Hanjani, M. et al., "Tracking Genomic Cancer Evolution for Precision Medicine: The Lung TRACERx Study", PLOS Biology, vol. 12, No. 7, Jul. 2014, 1-7.
Jamal-Hanjani, M. et al., "Tracking the Evolution of Non-Small-Cell Lung Cancer", The New England Journal of Medicine, vol. 376, No. 22, Jun. 1, 2017, 2109-2121.
Jarvie, T. , "Next generation sequencing technologies", Drug Discovery Today: Technologies, vol. 2, No. 3, 2005, 255-260.
Jen, J. et al., "An Overview on the Isolation and Analysis of Circulating Tumor DNA in Plasma and Serum", Annals New York Academy of Sciences, 2000, 8-12.
Jenkins, S. et al., "High-throughput SNP genotyping", Comparative and Functional Genomics, vol. 3, Dec. 5, 2001, 57-66.
Jennings, C. et al., "Investigation of Effects of Acid Citrate Dextrose and EDTA on Ability to Quantitatively Culture Human Immunodeficiency Virus", Journal of Clinical Microbiology, vol. 38, No. 9, 2000, 3522.
Jett, K. et al., "Clinical and genetic aspects of neurofibromatosis 1", Genetics In Medicine, vol. 12, No. 1, Jan. 2010, 11 pages.
Jewesburty, E.C.O. , "Reactions after Transfusion of Stored Blood", The British Medical Journal, vol. 1, No. 4191, 1941, 664-665.
Jiang, P. et al., "The Long and Short of Circulating Cell-Free DNA and the Ins and Outs of Molecular Diagnostics", Trends in Genetics, vol. 32, No. 6, Jun. 2016, 360-371.
Johnson, D. S. et al., "Genome-Wide Mapping of in Vivo Protein-DNA Interactions", Science, vol. 316, Jun. 8, 2007, 1497-1502.
Johnson, D.S. et al., "Comprehensive Analysis of Karyotypic Mosaicism Between Trophectoderm and Inner Cell Mass", Molecular Human Reproduction, 16(12), 2010, 944-949.
Johnson, J. B. et al., "Differential mechanisms of complementmediated neutralization of the closely related paramyxoviruses simian virus 5 and mumps virus", Virology, vol. 376, No. 1, 2008, 112-123.
Johnson, K. L. et al., "Interlaboratory Comparison of Fetal Male DNA Detection from Common Maternal Plasma Samples by Real-Time PC", Clinical Chemistry, vol. 50, No. 3, 2004, 516-521.
Johnson D.S, et al., "Preclinical Validation of a Microarray Method for Full Molecular Karyotyping of Blastomeres in a 24-h Protocol", Human Reproduction, 25 (4), 2010, 1066-1075.
Jung, K. et al., "Cell-free DNA in the blood as a solid tu1nor biomarker- A critical appraisal of the literature", Clinica Chimica Acta, vol. 411, 2010, 1611--1624.
Juppner, H. et al., "Functional Properties of the PTH/PTHrP Receptor", Bone, vol. 17, No. 2 Supplement, Aug. 1995, 39S-42S.
Kalendar, Ruslan et al., "Java Web Tools for PCR, in Silico PCR, and Oligonucleotide Assembly and Analysis", Genomics, vol. 98, 2011, pp. 137-144.
Kamat, A. A. et al., "Quantification of total plasma cell-free DNA in ovarian cancer using real-time PCR", Ann N Y Acad Sci., vol. 1075, Sep. 2006, 230-234.
Kamel, A. M. et al., "A simple strategy for breakpoint fragment determination in chronic myeloid leukemia", Cancer Genetics and Cytogenetics, vol. 122, 2000, 110-115.
Kane, M. et al., "Application of Less Primer Method to Commercial Kits", Forensic Science International: Genetics Supplement Series, vol. 1, Issue 1, 2008, 41-43.

(56) References Cited

OTHER PUBLICATIONS

Kane, M. , "Application of Less Primer Method Tto Multiplex PCR", International Congress Series, vol. 1288, 2006, pp. 694-696.
Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.
Kapadia, Samir R. et al., "Impact of Intravascular Ultrasound in Understanding Transplant Coronary Artery Disease", Current Opinion in Cardiology, vol. 14, No. 2, Mar. 1, 1999, 1-19.
Kaplinski, Lauris et al., "MultiPLX: Automatic Grouping and Evaluation of PCR Primers", Bioinformatics, 21(8), 2005, 1701-1702.
Karger, et al., "DNA Sequencing By Capillary Electrophoresis" Electrophoresis, vol. 30, Supplement 1, Jun. 1, 2009, 1-11.
Karoui, Noureddine E. et al., "Getting More from Digital SNP Data", Statistics in Medicine, vol. 25, Issue 18, Jan. 5, 2006, 3124-3133.
Kass, et al., "Diagnosis of Graft Coronary Artery Disease", Current Opinion in Cardiology, vol. 22, No. 2, Mar. 1, 2007, 139-145.
Kathiresan, Sekar et al., "Genome-wide Association of Early-onset Myocardial Infarction With Common Single Nucleotide Polymorphisms, Common Copy Number Variants, and Rare Copy Number Variants", Nature Genetics, vol. 41, No. 3, Mar. 1, 2009, 1-23.
Kazakov, V.I. et al., "Extracellular DNA in the Blood of Pregnant Women", Tsitologia, vol. 37, No. 3, 1995, 1-8.
Keith, L. et al., "Clinical Experience With the Prevention of Rh-Isoimmunization: A Historical Comparative Analysis", American Journal of Reproductive Immunology, vol. 5, 1984, 84-89.
Keller, M. C. et al., "Non-Pathological Paternal Isodisomy of Chromosome 2 Detected From a Genome-Wide SNP Scan", American Journal of Medical Genetics, Part A, 2009, 1823-1826.
Kennedy, S. R. et al., "Detecting ultralow-frequency mutations by Duplex Sequencing", Nature Protocols, vol. 9, No. 11, 2014, 2586-2606.
Kibbe, Warren A. , "Oligocalc: An Online Oligonucleotide Properties Calculator", Nucleic Acids Research, vol. 35, 2007, pp. W43-W46.
Kiernan, J. A. , "Formaldehyde, formalin, paraformaldehyde and glutaraldehyde: What they are and what they do.", Microscopy Today, vol. 1, 2000, 8-12.
Kijak, G. et al., "Discrepant Results in the Interpretation of HIV-1 Drug-Resistance Genotypic Data Among Widely Used Algorithms", HIV Medicine, 4, 2003, 72-78.
Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Kimmel, G. et al., "GERBIL: Genotype resolution and block identification using likelihood", PNAS, vol. 102, No. 1, Jan. 4, 2005, 158- 162.
Kinde, I. et al., "Detection and quantification of rare mutations with massively parallel sequencing", PNAS, vol. 108, No. 23, Jun. 7, 2011, 9530-9535.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Kirkness, E. F. et al., "Sequencing of isolated sperm cells for direct haplotyping of a human genome", Genome Research, vol. 23, 2013, 826-832.
Kivioja, T. et al., "Counting absolute number of molecules using unique molecular identifiers", Nature Proceedings, Apr. 14, 2011, 18 pgs.
Kivioja, T. et al., "Counting absolute numbers of molecules using unique molecular identifiers", Nature Methods, Advance Online Publication, Nov. 20, 2011, 1-5.
Kivioja, T. et al., "Counting absolute numbers of molecules using unique molecular identifiers", Nature Methods, vol. 9, No. 1, Jan. 2012, 72-76.
Kobashigawa, et al., "Multicenter Intravascular Ultrasound Validation Study Among Heart Transplant Recipients", Journal of the American College of Cardiology, vol. 45, No. 9, May 3, 2005, 1532-1537.
Koboldt, et al., "VarScan: Variant Detection in Massively Parallel Sequencing of Individual and Pooled Samples", Bioinformatics, vol. 25, No. 17, Jun. 19, 2009, 2283-2285.
Koelman, et al., "Donor-derived Soluble HLA Plasma Levels Can Not Be Used to Monitor Graft Rejection iIn Heart Transplant Recipients", Transplant Immunology, vol. 8, No. 1, Mar. 1, 2000, 57-64.
Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.
Koide, K. et al., "Fragmentation of cell-free fetal DNA in plasma and urine of pregnant women", Prenatal Diagnosis, vol. 25, 2005, 604-607.
Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.
Konfortov, B A. et al., "A High-Resolution HAPPY Map of Dictyostelium discoideum Chromosome 6", Genome Research, vol. 10, No. 11, Nov. 2000, 1737-1742.
Konfortov, Bernard A. et al., "An Efficient Method for Multi-Locus Molecular Haplotyping", Nucleic Acids Research, 35(1), e6, 2007, 8 pgs.
Kopreski, MS et al., "Detection of mutant K-ras DNA in plasma or serum of patients with colorectal cancer", British Journal of Cancer, vol. 76, No. 10, 1997, 1293-1299.
Koressaar, Triinu et al., "Enhancements and Modifications of Primer Design Program Primer3", Bioinformatics, vol. 23, 2007, pp. 1289-1291.
Korn, et al., "Integrated Genotype Calling and Association Analysis of SNPS, Common Copy Number Polymorphisms and Rare CNVS", Nature Genetics, vol. 40, No. 10, Oct. 1, 2008, 1253-1260.
Krjutskov, K. et al., "Development of a single tube 640-plex genotyping method for detection of nucleic acid variations on microarrays", Nucleic Acids Research, vol. 36, No. 12, May 23, 2008, 7 pages.
Kuhn, H. et al., "Rolling-circle amplification under topological constraints", Nucleic Acids Research, vol. 30, No. 2, 2002, 574-580.
Kukita, Y. et al., "High-fidelity target sequencing of individual molecules identified using barcode sequences: de nova detection and absolute quantitation of mutations in plasma cell-free DNA from cancer patients" DNA Research, vol. 22, No. 4, Jun. 29, 2015, 269-277.
Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Kumar, P. et al., "Ethylenegycol-Bis-(B-Aminoethylether)Tetraacetate as a Blood Anticoagulant: Preservation of Antigen-Presenting Cell Function and Antigen-Specific Proliferative Response of Peripheral Blood Mononuclear Cells from Stored Blood", Clinical and Diagnostic Laboratory Immunology, vol. 7, No. 4, 2000, 578-583.
Kunishima, S. et al., "First description of somatic mosaicism in MYH9 disorders", British Journal of Haematology, vol. 128, 2005, 360-365.
Kwok, P. Y. , "High-throughput genotyping assay approaches", Pharmacogenomics, vol. 1, No. 1, 2000, 1-5.

(56) References Cited

OTHER PUBLICATIONS

Lambert, et al., "Quantification of Maternal Microchimerism by HLA-Specific Real-time Polymerase Chain Reaction", Arthritis and Rheumatism, vol. 50, No. 3, Mar. 1, 2004, 906-914.
Lambert-Messerlian, G. et al., "Adjustment of Serum Markers in First Trimester Screening", Journal of Medical Screening, 16 (2), 2009, 102-103.
Landegren, U. et al., "Padlock and proximity probes for in situ and array-based analyses: tools for the post-genomic era", Comparative and Functional Genomics, vol. 4, 2003, 525-530.
Lander, E. S. et al., "Initial sequencing and analysis of the human genome", Nature, vol. 409, Feb. 15, 2001, 860-921.
Langmore, J. , "Quality Control and Pre-Qualifications of NGS Libraries Made from Clinical Samples", ABRF 2013 Satellite Workshop, Mar. 2, 2013, 35 pages.
Lapaire, O. et al., "Array-CGH analysis of cell-free fetal DNA in 10 mL of amniotic fluid supernatant", Prenatal Diagnosis, vol. 27, May 17, 2007, 616-621.
Lapierre, J.M. et al., "Analysis of uncultured amniocytes by comparative genomic hybridization: a prospective prenatal study", Prenatal Diagnosis, vol. 20, 2000, 123-131.
Lardeux, Frederic et al., "Optimization of a Semi-nested Multiplex PCR to Identify Plasmodium Parasites in Wild-Caught Anopheles in Bolivia, and Its Application to Field Epidemiological Studies", Transactions of the Royal Society of Tropical Medicine and Hygiene, vol. 102, 2008, pp. 485-492.
Larsen, J. B. et al., "Single-step Nested Multiplex PCR to Differentiate Between Various Bivalve Larvae", Marine Biology, vol. 146, 2005, pp. 1119-1129.
Lasken, R. S. et al., "Whole genome amplification: abundant supplies of DNA from precious samples or clinical specimens", Trends in Biotechnology, vol. 21, No. 12, Dec. 2003, 531-535.
Lathi, Ruth B. et al., "Informatics Enhanced SNP Microarray Analysis of 30 Miscarriage Samples Compared to Routine Cytogenetics", PLoS ONE, 7(3), 2012, 5 pgs.
Lavebrat, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.
Lavebratt, Catharina et al., "Pyrosequencing-based SNP Allele Frequency Estimation in DNA Pools", Human Mutation, vol. 23, Issue 1, Dec. 19, 2003, 92-97.
Lavrentieva, I et al., "High Polymorphism Level of Genomic Sequences Flanking Insertion Sites of Human Endogenous Retroviral Long Terminal Repeats", FEBS Letters, vol. 443, No. 3, Jan. 29, 1999, 341-347.
Leamon, John H. et al., "A massively parallel PicoTiterPlate based platform for discrete picoliter-scale polymerase chain reactions", Electrophoresis, vol. 24, No. 21, Nov. 1, 2003, 3769-3777.
Leary, R. J. et al., "Development of Personalized Tumor Biomarkers Using Massively Parallel Sequencing", Science Translational Medicine, vol. 2, No. 20, Feb. 24, 2010, 1-8.
Leary, Rebecca J et al., "Detection of Chromosomal Alterations in the Circulation of Cancer Patients with Whole-Genome Sequencing", Science Translational Medicine, 4, 162, 2012, 12.
Lecomte, T. et al., "Detection of Free-Circulating Tumor-Associated Dna in Plasma of Colorectal Cancer Patients and Its Association With Prognosis", Int. J. Cancer, vol. 100, 2002, 542-548.
Lee, J et al., "Anchored Multiplex PCR Enables Sensitive and Specific Detection of Variants in Circulating Tumor DNA by Next-Generation Sequencing", DOI:https://doi.org/10.1016/j.cancergen.2017.04.049, Cancer Genetics 214-215, 2017, 47.
Lee, T. et al., "Down syndrome and cell-free fetal DNA in archived maternal serum", AmJ Obstet Gynecol, vol. 187, No. 5, 1217-1221, Nov. 2002.
Lee, T.H. et al., "Quantitation of genomic DNA in plasma and serum samples: higher concentrations of genomic DNA found in serum than in plasma", Transfusion, vol. 41, Feb. 2001, 276-282.
Levsky, J. M. et al., "Fluorescence in situ hybridization: past, present and future", Journal of Cell Science, vol. 116, No. 14, 2003, 2833-2838.
Levsky, Jeffrey M. et al., "Efficacy of Coronary Ct Angiography: Where We Are, Where We Are Going and Where We Want to Be", Journal of Cardiovascular Computed Tomography, vol. 3, Supplement 2, Nov. 2, 2009, s99-s108.
Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.
Li, et al., "Mapping Short DNA Sequencing Reads and Calling Variants Using Mapping Quality Scores", Genome Research, vol. 18, No. 11,, Aug. 19, 2008, 1851-1858.
Li, et al., "Multiplex Padlock Targeted Sequencing Reveals Human Hypermutable CpG Variations", Genome Research, vol. 19, No. 9, Jun. 12, 2009, 1606-1615.
Li, et al., "SOAP2: An Improved Ultrafast Tool for Short Read Alignment", Bioinformatics, vol. 25, No. 15, Aug. 1, 2009, 1966-1967.
Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.
Li, R. et al., "SNP detection for massively parallel whole-genome resequencing", Genome Research, vol. 19, 2009, 1124-1132.
Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.
Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Detection of Donor-specific DNA Polymorphisms in the Urine of Renal Transplant Recipients", Clinical Chemistry, vol. 49, No. 4, Apr. 1, 2003, 655-658.
Li, Ying et al., "Ready detection of donor-specific single-nucleotide polymorphisms in the urine of renal transplant recipients by matrix-assisted laser desorption/ionization time-of-flight mass spectrometry", Ying Li et al., "Ready detection of donor-specific single-nucleotide polymorphisms in the urine of renal transplant recipients by matrix-assisted laser desorption/ionization time-of-flight mass spectrometry", Clin Chem, Oct. 2005, vol. 51,Issue. 10,pp. 1903-1904, Oct. 1, 2005, 1903-1904.
Li, Ying et al., "Size Separation of Circulatory DNA in Maternal Plasma Permits Ready Detection of Fetal DNA Polymorphisms", Clinical Chemistry, 50, 6, 2004, 1002-1011.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Lichtenstein, A. V. et al., "Circulating Nucleic Acids and Apoptosis", Annals New York Academy of Sciences, vol. 945, Aug. 1, 2001, 239-249.
Liew, Michael et al., "Genotyping of Single-Nucleotide Polymorphisms", Clinical Chemistry, 50(7), 2004, 1156-1164.
Life Technologies, "Ion AmpliSeq Comprehensive Cancer Panel", 2012, 2 pgs.
Life Technologies, "Ion AmpliSeq™ Designer provides full flexibility to sequence genes of your choice", 2012, 4 pages.
Liljedahl, Ulrika et al., "Detecting Imbalanced Expression of SNP Alleles by Minisequencing on Microarrays", BMC Biotechnology, vol. 4, Article No. 24, Oct. 22, 2004, 1-10.
Lindberg, J. et al., "Exome Sequencing of Prostate Cancer Supports the Hypothesis of Independent Tumour Origins", European Urology, vol. 63, 2013, 347-353.
Lindroos, Katatina et al., "Genotyping SNPs by Minisequencing Primer Extension Using Oligonucleotide Microarrays", Methods in

(56) References Cited

OTHER PUBLICATIONS

Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, et al., "Next-generation Sequencing of Plasma/Serum DNA: An Emerging Research and Molecular Diagnostic Tool", Clinical Chemistry, vol. 55, No. 4, Apr. 1, 2009, 607-608.
Lo, "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet, 2, 8676, 1989, 1363-1365.
Lo, et al., "Presence of Donor-specific Dna in Plasma of Kidney and Liver-transplant Recipients", Lancet, vol. 351, No. 9112, May 2, 1998, 1329-1330.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88(11), Dec. 1, 1996, 4390-4395.
Lo, Y M. et al., "Circulating Nucleic Acids in Plasma and Serum: An Overview", Annals of the New York Academy of Sciences, vol. 945, Sep. 1, 2001, 1-7.
Lo, Y. , "Noninvasive prenatal detection of fetal chromosomal aneuploidies by maternal plasma nucleic acid analysis: a review of the current state of the art", BJOG an International Journal of Obstetrics and Gynaecology, vol. 116, 2009, 152-157.
Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Y.M. Dennis et al., "Maternal Plasma DNA Sequencing Reveals the Genome-Wide Genetic and Mutational Profile of the Fetus", Science Translational Medicine,, 2 (61), 2010, 13.
Lui, Yanni Y. et al., "Origin of Plasma Cell-Free DNA after Solid Organ Transplantation", Clinical Chemistry, vol. 49, No. 3, Mar. 1, 2003, 495-496.
Lun, Fiona M. et al., "Microfluidics Digital PCR Reveals a Higher Than Expected Fraction of Fetal DNA in Maternal Plasma", Clinical Chemistry, vol. 54, No. 10, Aug. 14, 2008, 1664-1672.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Ma, Xiaotu et al., "Rise and fall of subclones from diagnosis to relapse in pediatric B-acute lymphoblastic leukaemia", Nature Communications, vol. 6, Mar. 19, 2015, 1-12.
Mackiewicz, D. et al., "Distribution of Recombination Hotspots in the Human Genome—A Comparison of Computer Simulations with Real Data", PLOS One, vol. 8, No. 6, Jun. 2013, 11 pages.
Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 TRIAL", Cancer Research, vol. 79, No. 4 Supplement, Feb. 15, 2019.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Maniatis, T. et al., "In: Molecular Cloning: A Laboratory Manual", Cold Spring Harbor Laboratory, New York, Thirteenth Printing, 1986, 458-459.
Lo, Y.M. Dennis et al., "Plasma placental RNA allelic ratio permits noninvasive prenatal chromosomal aneuploidy detection", Nature Medicine, 13 (2), 2007, 218-223.
Lo, Y.M. Dennis et al., "Presence of Fetal DNA in Maternal Plasma and Serum", The Lancet, 350, 1997, 485-487.
Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.
Lo, Y.M.D. , "Fetal DNA in Maternal Plasma: Biology and Diagnostic Applications", Clinical Chemistry, vol. 46, No. 12, 2000, 1903-1906.
Lo, Y.M.D. et al., "Prenatal diagnosis: progress through plasma nucleic acids", Nature Reviews, vol. 8, 2007, 71-77.
Lo, Y-M D. , "Non-invasive prenatal diagnosis using fetal cells in maternal blood", J. Clin. Pathol., vol. 47, 1994, 1060-1065.
Lo, Y-M.D et al., "Detection of Single-Copy Fetal DNA Sequence from Maternal Blood", The Lancet, 335, 1990, 1463-1464.
Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M.D. et al., "Detection of Fetal RhD Sequence from Peripheral Blood of Sensitized RhD-Negative Pregnant Women", British Journal of Haematology, 87, 1994, 658-660.
Lo, Y-M.D. et al., "Prenatal Determination of Fetal RhD Status by Analysis of Peripheral Blood of Rhesus Negative Mothers", The Lancet, 341, 1993, 1147-1148.
Loh, Elwyn , "Anchored PCR: Amplification with Single-sided Specificity", Methods, vol. 2, 1991, pp. 11-19.
Lovmar, L. et al., "Quantitative evaluation by minisequencing and microarrays reveals accurate multiplexed SNP genotyping of whole genome amplified DN", Nucleic Acids Research, vol. 31, No. 21, 2003,, 9 pgs.
Lu, I. et al., "Establishment of a system based on universal multiplex-PCR for screening genetically modified crops", Anal. Bioanal. Chem, vol. 396, Oct. 24, 2009, 2055-2064.
Lu, S. et al., "Probing Meiotic Recombination and Aneuploidy of Single Sperm Cells by Whole-Genome Sequencing", Science, vol. 338, Dec. 21, 2012, 1627-1630.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Lui, Yanni Y. et al., "Circulating DNA in Plasma and Serum: Biology, Preanalytical Issues and Diagnostic Applications", Clinical Chemistry and Laboratory Medicine, vol. 40, No. 10, Oct. 29, 2002, 962-968.
Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Mardis, E. R. , "The impact of next-generation sequencing technology on genetics", Trends in Genetics, vol. 24, No. 3, Feb. 11, 2008, 133-141.
Marguiles, M. et al., "Genome Sequencing in Open Microfabricated High Density Picoliter Reactors", Nature, vol. 437, No. 7057, Sep. 15, 2005, 376-380.
Margulies, M. et al., "Genome sequencing in microfabricated high-density picolitre reactors", Nature, vol. 437, Sep. 15, 2005, 376-380.
Margulies, M. et al., "Genome sequencing in microfabricated high-density picolitre reactors plus Supplemental Methods", Nature, vol. 437, Sep. 15, 2005, 40 pgs.
Marianes, Alexis E. et al., "Targets of Somatic Hypermutation within Immunoglobulin Light Chain Genes in Zebrafish", Immunology, vol. 132, 2010, pp. 240-255.
Markoulatos, P. et al., "Multiplex Polymerase Chain Reaction: A Practical Approach", Journal of Clinical Laboratory Analysis, vol. 16, 2002, 47-51.
Maron, Jill L. et al., "Cell-free Fetal DNA Plasma Extraction and Real-time Polymerase Chain Reaction Quantification", Methods In Molecular Medicine, vol. 132, Aug. 1, 2007, 51-63.

(56) References Cited

OTHER PUBLICATIONS

Marshutina, N. V. et al., "Comparative Clinical and Diagnostic Significance of Some Serological Tumor Associated Markers for Different Histological Types of Lung Cancer", Russian Oncological Journal, vol. 3, 2010, 13-16.
Martinez- Lopez, J. et al., "Real-time PCR Quantification of Haematopoietic Chimerism after Transplantation: A Comparison Between TaqMan and Hybridization Probes Technologies", International Journal of Laboratory Hematology, vol. 32, Issue 1, Part 1, May 12, 2009, e17-e25.
Martins, et al., "Quantification of Donor-derived DNA in Serum: A New Approach of Acute Rejection Diagnosis in a Rat Kidney Transplantation Model", Transplantation Proceedings, vol. 37, No. 1,, Jan. 1, 2005, 87-88.
Masuzaki, H. et al., "Detection of cell free placental DNA in maternal plasma: direct evidence from three cases of confined placental mosaicism", J Med Genet, vol. 41, 2004, 289-292.
Matsubara, T. et al., "Pantropic Retroviral Vectors Integrate and Express in Cells of the Malaria Mosquito, Anopheles Gambiae", PNAS, vol. 93, 1996, pp. 6181-6185.
Matsuzaki, H. et al., "Genotyping over 100,000 SNPs on a pair of oligonucleotide arrays", Nature Methods, vol. 1, No. 2, Nov. 2004, 109- 111.
May, Robert M. , "How Many Species Are There on Earth?", Science, 241, Sep. 16, 1988, 1441-1449.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
McCloskey, M. L. et al., "Encoding PCR Products with Batch-stamps and Barcodes", Biochem Genet., vol. 45, Oct. 23, 2007, 761-767.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.
McDonald, J. P. et al., "Novel thermostable Y-family polymerases: applications for the PCR amplification of damaged or ancient DNAs", Nucleic Acids Research, vol. 34, No. 4, 2006, 1102-1111.
Mennuti, M. et al., "Is It Time to Sound an Alarm About False-Positive Cell-Free DNA Testing for Fetal Aneuploidy?", American Journal of Obstetrics, 2013, 5 pgs.
Merriam-Webster, "Medical Definition of Stimulant", http://www.merriam-webster.com/medical/stimulant, Mar. 14, 2016, 7 pages.
Merriam-Webster, "Universal Definition", Merriam-Webster.com, 3 pages.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Mertes, F. et al., "Targeted enrichment of genomic DNA regions for next-generation sequencing", Briefings in Functional Genomics, vol. 10, No. 6, Nov. 26, 2011, 374-386.
Messmer, Trudy O. et al., "Application of a Nested, Multiplex PCR to Psittacosis Outbreaks", Journal of Clinical Microbiology, vol. 35, No. 8, 1997, pp. 2043-2046.
Metzker, M. L. et al., "Polymerase Chain Reaction", Encyclopedia of Medical Devices and Instrumentation, vol. 5, Second Edition, 2006, 380-387.
Metzker, M. L. et al., "Quantitation of Mixed-Base Populations of HIV-1 Variants by Automated DNA Sequencing with BODIPY* Dye-Labeled Primers", BioTechniques, vol. 25, Sep. 1998, 446-462.
Meuzelaar, Linda S. et al., "Megaplex PCR: A Strategy for Multiplex Amplification", Nature Methods, vol. 4, 2007, pp. 835-837.
Meyer, M et al., "Illumina Sequencing Library Preparation for Highly Multiplexed Target Capture and Sequencing", Cold Spring Harbor Protocols, vol. 2010, Issue 6, Jun. 2010, 1-10.
Meyerson, M. et al., "Advances in understanding cancer genomes through second-generation sequencing", Nature Reviews: Genetics, vol. 11, Oct. 2010, 685-696.
Mikkelsen, T. S. et al., "Genome-wide maps of chromatin state in pluripotent and lineage-committed cells", Nature, vol. 448, No. 2, Aug. 2007, 553-562.
Milani, et al., "Genotyping Single Nucleotide Polymorphisms by Multiplex Minisequencing Using Tag-arrays", DNA Microarrays for Biomedical Research, vol. 529, Jan. 16, 2009, 215-229.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Miner, B. E. et al., "Molecular barcodes detect redundancy and contamination in hairpin-bisulfite PCR", Nucleic Acids Research, vol. 32, No. 17, Sep. 30, 2004, 1-4.
Minkoff, E. et al., "Stem Cells, Cell Division, and Cancer", Biology Today Third Edition, Chapter 12, 2004, 10 pages.
Miramontes, Pedro et al., "DNA Dimer Correlations Reflect in Vivo Conditions and Discriminate Among Nearest-neighbor Base Pair Free Energy Parameter Measures", Physica A, vol. 321, 2003, pp. 577-586.
Mitra, S. et al., "Chapter 4 Classification Techniques", Introduction to Machine Learning and Bioinformatics, First Edition, 2008, 101-127.
Morand, et al., "Hesperidin contributes to the vascular protective effects of orange juice: a randomized crossover study in healthy volunteers", Am J Clin Nutr. Jan. 2011;93(1 ):73-80. Epub Nov. 10, 2010.
Moreau, Valerie et al., "Zip Nucleic Acids: New High Affinity Oligonucleotides as Potent Primers for PCR and Reverse Transcription", Nucleic Acids Research, vol. 37, No. 19, e130, 2009, 14 pages.
Moreira, et al., "Increase in and Clearance of Cell-free Plasma DNA in Hemodialysis Quantified by Real-time PCR", Clinical Chemistry and Laboratory Medicine, vol. 44, No. 12, Dec. 13, 2006, 1410-1415.
Morris, J. K. et al., "Trends in Down's syndrome live births and antenatal diagnoses in England and Wales from 1989 to 2008: analysis of data from the National Down Syndrome Cytogenetic Register", BMJ Online, vol. 339, Oct. 2009, 5 pages.
Munne, S. et al., "Chromosome Abnormalities in Human Embryos", Textbook of Assisted Reproductive Techniques, 2004, pp. 355-377.
Munne, S. et al., "Chromosome abnormalities in human embryos", European Society of Human Reproduction and Embryology: Human Reproduction Update, vol. 4, No. 6, 1998, 842-855.
Munne, S. et al., "Improved implantation after preimplantation genetic diagnosis of aneuploidy", Reproductive BioMedicine Online, vol. 7., No. 1., May 15, 2003, 91-97.
Murali, R. et al., "Crystal structure of Taq DNA polymerase in complex with an inhibitory Fab: The Fab is directed against an intermediate in the helix-coil dynamics of the enzyme", Proc. Natl. Acad. Sci. USA, vol. 95, Oct. 1998, 12562-12567.
Murtaza, M. et al., "Non-Invasive Analysis of Acquired Resistance to Cancer Therapy by Sequencing of Plasma DNA", Nature (doi:10.1038/nature12065), 2013, 6 pgs.
Muse, Spencer V. , "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.
Nagalla, S. R. et al., "Proteomic Analysis of Maternal Serum in Down Syndrome: Identification of Novel Protein Biomarkers", Journal of Proteome Research, vol. 6, Mar. 21, 2007, 1245-1257.

(56) References Cited

OTHER PUBLICATIONS

Nakamura, N. et al., "Ex Vivo Liver Perfusion with Arterial Blood from a Pig with Ischemic Liver Failure", Artificial Organs, vol. 23, No. 2, 1999, 153-160.
Namlos, H. M. et al., "Noninvasive Detection of ctDNA Reveals Intratumor Heterogeneity and Is Associated with Tumor Burden in Gastrointestinal Stromal Tumor", Molecular Cancer Therapeutics, vol. 17, No. 11, 2018, 2473-2480.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Natera, Inc., "Declaration of Sandra L. Haberny", May 16, 2019, 3 pages.
Natera, Inc., "Defendant Natera, Inc.'S Invalidity Contentions Under Patent L.R. 3-3; Document Production Accompanying Invalidity Contentions Under Patent L.R. 3-4", Aug. 20, 2018, 17 pages.
Natera, Inc., "Exhibit 8 EHRICH Invalidity Chart", Aug. 20, 2018, 16 pages.
Natera, Inc., "Exhibits A-H to Haberny Declaration", May 16, 2019, 192 pages.
Natera, Inc., "Motion to Dismiss", May 16, 2019, 2 pages.
Natera, Inc., "Natera Inc.'s First Amended Answer, Affirmative Defenses and Counterclaims", Aug. 16, 2018, 28 pages.
Natera, Inc., "Natera, Inc.'s Supplemental Objections and Response to Plaintiff Illumina, Inc.'S Interrogatory No. 8", Mar. 20, 2019, 29 pages.
Natera, Inc., "Opening Brief in Support of Motion to Dismiss", May 16, 2019, 26 pages.
Natera, Inc., , "Petitioner Reply Per Board Order of Nov. 2, 2018 (Paper No. 10)", Nov. 9, 2018, 8 pgs.
National Institutes of Health, , "Genetics Home Reference: Your Guide to Understanding Genetic Conditions", Feb. 28, 2014, 2 pgs.
Nawroz, H et al., "Microsatellite Alterations in Serum DNA of Head and Neck Cancer Patients", Nature Medicine, vol. 2, No. 9, Sep. 1996, 1035-1037.
NCBI, "Blast of AAAAAAAAATTTAAAAAAAAATTT", 2015, 9 pages.
NCBI, "db SNP rs2056688", 2015, 3 pages.
NCBI, "dbSNP record for rs1294331", Retrieved from the Internet: <URL: www.ncbi.nlm.nih.gov/snp/?term=rs 1294331 >, 2019, 2 pgs.
NCBI, "dbSNP record for rs1872575", Retrieved from the Internet: <URL: www.ncbi.nlm.nih.gov/snp/?term=rs1872575, 2019, 2 pgs.
NCBI, "dbSNP record for rs2362450", Retrieved from the Internet: <URL: www.ncbi.nlm.nih.gov/snp/?term=rs2362450>, 2019, 1 pg.
NCBI, "dbSNP record for rs2384571", Retrieved from the Internet: <URL: www.ncbi.nlm.nih.gov/snp/?term=rs2384571>, 2019, 2 pgs.
NCBI, "dbSNP record for rs2498982", Retrieved from the Internet: <URL: www.ncbi.nlm.nih.gov/snp/?term=rs2498982>, 2019, 3 pgs.
NCBI, "dbSNP record for rs3731877", Retrieved from the Internet: <URL: www.ncbi.nlm.nih.gov/snp/?term=rs3731877>, 2019, 2 pgs.
Neve, B. et al., "Rapid SNP Allele Frequency Determination in Genomic DNA Pools by Pyrosequencing", BioTechniques, vol. 32, No. 5, May 1, 2002, 1138-1142.
New England Biolabs, "NucleicAcids, Linkers and Primers: Random Primers", 1998/99Catalog, 1998, 121 and 284.
Newman, A. M. et al., "Integrated digital error suppression for improved detection of circulating tumor DNA", Nature Biotechnology, vol. 34, No. 5, May 2016, 547-555.
Ng, et al., "Multiplex Sequencing of Paired-end Ditags (MS-PET): A Strategy for the Ultra-high-throughput Analysis of Transcriptomes and Genomes", Nucleic Acids Research, vol. 34, No. 12, Jul. 13, 2006, 1-10.
Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.
Nguyen-Dumont, T. , "A high-plex PCR approach for massively parallel sequencing", BioTechniques, vol. 55, No. 2, Aug. 2013, 69-74.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H et al., "Validation of Targeted Sequencing of Single- Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nilsson, M. et al., "Padlock Probes: Circularizing Oligonucleotides for Localized DNA Detection", Science, vol. 265, Sep. 10, 1994, 2085-2088.
Nishigaki, K. et al., "Random PCR-Based Genome Sequencing: A Non-Divide-and-Conquer Strategy", Dna Research, vol. 7, 2000, 19-26.
Nishiwaki, Morie et al., "Genotyping of Human Papillomaviruses by a Novel One-step Typing Method With Multiplex PCR and Clinical Applications", Journal of Clinical Microbiology, vol. 46, 2008, pp. 1161-1168.
Norton, S. E. et al., "A stabilizing reagent prevents cell-free DNA contamination by cellular DNA in plasma during blood sample storage and shipping as determined by digital PCR", Clin Biochem., vol. 46, No. 15, Oct. 2013, 1561-1565.
Nui, A. et al., "The Functional Integrity of a Normothermic Perfusion System Using Artificial Blood in Pig Liver", Journal of Surgical Research, Vo. 131, 2006, 189-198.
Nygren, et al., "Quantification of Fetal DNA by Use of Methylation-Based DNA Discrimination", Clinical Chemistry 56:10 1627-1635 (2010).
O'connell, G. C. et al., "High Interspecimen Variability in Nucleic Acid Extraction Efficiency Necessitates the Use of Spike-In Control for Accurate qPCR-based Measurement of Plasma Cell-Free DNA Levels", Lab Medicine, vol. 48, 2017, 332-338.
Oeth, et al., "iPLEX™ Assay: Increased Plexing Efficiency and Flexibility for MassARRAY System Through Single Base Primer Extension with Mass-Modified Terminators", Sequenom Application Note Doc. No. 8876-006, Apr. 28, 2005, 1-12.
Ogino, S. et al., "Bayesian Analysis and Risk Assessment in Genetic Counseling and Testing", Journal of Molecular Diagnostics, 6 (1), 2004, 9 pgs.
Ohara, O et al., "One-sided Polymerase Chain Reaction: The Amplification of cDNA", Proceedings of the National Academy of Sciences, vol. 86, 1989, 5673-5677.
Ohira, T. et al., "Tumor volume determines the feasibility of cell-free DNA sequencing for mutation detection in non-small cell lung cancer", Cancer Science, vol. 107, 2016, 1660-1666.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
Okou, et al., "Microarray-based Genomic Selection for High-throughput Resequencing", Nature Methods, vol. 4, No. 11, Oct. 14, 2007, 907-909.
Okou, David T. et al., "Combining Microarray-based Genomic Selection (MGS) with the Illumina Genome Analyzer Platform to Sequence Diploid Target Regions", Annals of Human Genetics, vol. 73, No. 5, Aug. 6, 2009, 502-513.
Olerup, O. et al., "HLA-DR typing by PCR amplification with sequence-specific primers (PCR-SSP) in 2 hours: an alternative to serological DR typing in clinical practice including donor-recipient matching in cadaveric transplantation", Tissue Antigens, vol. 39, No. 5, May 1992, 225-235.
Oliphant, A. et al., "Bead.Array™ Technology: Enabling an Accurate, Cost-Effective Approach to High-Throughput Genotyping", Bio Techniques, vol. 32, Jun. 2002, S56-S6.

(56) References Cited

OTHER PUBLICATIONS

Olivarius, S. et al., "High-throughput Verification of Transcriptional starting Sites by Deep-RACE", Bio Techniques, vol. 46, No. 2, Feb. 2009, 130-132.
Olive, M. et al., "Characterization of the DiFi Rectal Carcinoma Cell Line Derived from a Familial Adenomatous Polyposis Patient", in Vitro Cellular & Developmental Biology, vol. 29A, No. 3, Part 1, Mar. 1993, 239-248.
Oliver, Dwight H. et al., "Use of Single Nucleotide Polymorphisms (SNP) and Real-time Polymerase Chain Reaction for Bone Marrow Engraftment Analysis", The Journal of Molecular Diagnostics, vol. 2, No. 4, Nov. 1, 2000, 202-208.
Olivier, et al., "The Invader Assay for SNP Genotyping", Mutation Research, vol. 573, No. 1-2, Jun. 3, 2005, 103-110.
Olney, R. S. et al., "Chorionic Villus Sampling and Amniocentesis: Recommendations for Prenatal Counseling", MMWR: Recommendations and Reports, 44(RR-9), Jul. 21, 1995, 1-12.
O'Malley, R. et al., "An adapter ligation-mediated PCR method for high-throughput mapping of T-DNA inserts in the Arabidopsis genome", Nat. Protoc., 2, 2007, 2910-2917.
Orozco A.F., et al., "Placental Release of Distinct DNA-Associated Micro-Particles into Maternal Circulation: Reflective of Gestation Time and Preeclampsia", Placenta, 30, 2009, 891-897.
Orsouw, et al., "Complexity Reduction of Polymorphic Sequences (Crops): A Novel Approach for Large-scale Polymorphism Discovery in Complex Genomes", PLoS ONE, vol. 11:e1172, Nov. 14, 2017, 1-10.
Owczarzy, Richard et al., "Melting Temperatures of Nucleic Acids: Discrepancies in Analysis", Biophysical Chemistry, vol. 117, 2005, pp. 207-215.
Ozawa, Makiko et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report, (including copy of text in Japanese), 1994, 8.
Paez, Guillermo J. et al., "Genome coverage and sequence fidelity of Φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Paik, P. K. et al., "Next-Generation Sequencing of Stage IV Squamous Cell Lung Cancers Reveals an Association of P13K Aberrations and Evidence of Clonal Heterogeneity in Patients with Brain Metastases", Cancer Discovery, vol. 5, Apr. 30, 2015, 610-621.
Pakstis, et al., "Candidate SNPs for a Universal Individual Identification Panel", Human Genetics, vol. 121, No. 3-4,, Feb. 27, 2007, 305-317.
Pakstis, et al., "SNPS for Individual Identification", Forensic Science International, vol. 1, May 22, 2008, 479-481.
Palka-Santini, Maria et al., "Large Scale Multiplex PCR Improves Pathogen Detection by DNA Microarrays", BMC Microbiology, vol. 9, No. 1, 2009, 14 pages.
Palomaki, G. E. et al., "DNA sequencing of maternal plasma to detect Down syndrome: An international clinical validation study", Genetics in Medicine, vol. 13, No. 1, Nov. 2011, 913-920.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Panjkovich, Alejandro et al., "Comparison of Different Melting Temperature Calculation Methods for Short DNA Sequences", Bioinformatics, vol. 21, 2005, pp. 711-722.
Papadopoulou, E. et al., "Cell-Free DNA and RNA in Plasma as a New Molecular Marker for Prostate Cancer", Oncology Research, vol. 14, 2004, 439-445.
Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.
Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.
Parker, A. V. et al., "The Effect of Sodium Citrate on the Stimulation of Polymorphonuclear Leukocytes", Investigative Ophthalmology & Visual Science, vol. 26, 1985, 1257-1261.
Paruzynski, A. et al., "Genome-wide high-throughput integrome analyses by nrLAM-PCR and next-generation sequencing", Nature Protocols, vol. 5, No. 8, Jul. 8, 2010, 1379-1395.
Pask, R. et al., "Investigating the utility of combining 29 whole genome amplification and highly multiplexed single nucleotide polymorphism BeadArray TM genotyping", BMC Biotechnology, vol. 4, No. 15, Jul. 27, 2004, 8 pages.
Pastinen, T. et al., "Minisequencing: A Specific Tool for DNA Analysis and Diagnostics on Oligonucleotide Arrays", Genome Research, vol. 7, 1997, 606-614.
Pathak, A. et al., "Circulating Cell-Free DNA in Plasma/Serum of Lung Cancer Patients as a Potential Screening and Prognostic Tool", Clinical Chemistry, 52, 2006, 1833-1842.
Patil, N. et al., "Blocks of Limited Haplotype Diversity Revealed by High-Resolution Scanning of Human Chromosome 21", Science, vol. 294, Nov. 23, 2001, 1719-1723.
Paunio, T. et al., "Preimplantation diagnosis by whole-genome amplification, PCR amplification, and solid-phase minisequencing of blastomere DNA", Clinical Chemistry, vol. 42, No. 9, 1996, 1382-1390.
PCT/US2006/045281, "International Preliminary Report on Patentability", mailed May 27, 2008, 1 pg.
PCT/US2006/045281, "International Search Report and Written Opinion", mailed Sep. 28, 2007, 7 pgs.
PCT/US2008/003547, "International Search Report", mailed Apr. 15, 2009, 5 pgs.
PCT/US2009/034506, "International Search Report", mailed Jul. 8, 2009, 2 pgs.
PCT/US2009/045335, "International Search Report", mailed Jul. 27, 2009, 1 pg.
PCT/US2009/052730, "International Search Report", mailed Sep. 28, 2009, 1 pg.
PCT/US2010/050824, "International Search Report", mailed Nov. 15, 2010, 2 pgs.
PCT/US2011/037018, "International Search Report", mailed Sep. 27, 2011, 2 pgs.
PCT/US2011/061506, "International Search Report", mailed Mar. 16, 2012, 1 pgs.
PCT/US2011/066938, "International Search Report", mailed Jun. 20, 2012, 1 pg.
PCT/US2012066339, "International Search Report", mailed Mar. 5, 2013, 1 pg.
PCT/US2013/028378, "International Search Report and Written Opinion", mailed May 28, 2013, 11 pgs.
PCT/US2013/57924, "International Search Report and Written Opinion", mailed Feb. 18, 2014, 8 pgs.
PCT/US2014/051926, "International Search Report and Written Opinion", Dec. 9, 2014, 3 pgs.
Pearson, K. , "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pelizzari, C. A. et al., "Quantitative analysis of DNA array autoradiographs", Nucleic Acids Research, vol. 28, No. 22, 2000, 4577- 4581.
Pena, Sergio D.J et al., "Paternity Testing in the DNA Era", Trends In Genetics, 10, 6, 1994, 204-209.
Perakis, S. et al., "Advances in Circulating Tumor DNA Analysis", Advances in Clinical Chemistry, vol. 80, 2017, 73-153.

(56) References Cited

OTHER PUBLICATIONS

Pergament, E. et al., "Single-Nucleotide Polymorphism-Based Non-invasive Prenatal Screening in a High-Risk and Low-Risk Cohort", Obstetrics & Gynecology, vol. 124, No. 2, Part 1, Aug. 2014, 210-218 + Appendices.
Perkel, Jeffrey M. , "Overcoming the Challenges of Multiplex PCR", Biocompare Editorial Article, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, D. , "List of Materials Considered by David Peters, Ph.D.", Jun. 13, 2019, 2 pages.
Peters, David P. et al., "Noninvasive Prenatal Diagnosis of a Fetal Microdeletion Syndrome", New England Journal of Medicine, 365(19), 2011, 1847-1848.
Pfaffl, Michael W. , "Quantification Strategies in Real-time Pcr", A-Z of quantitative PCR, 2004, pp. 87-112.
Pfaffl, Michael W. , "Relative Expression Software Tool (RESTO) for Group-Wise Comparison and Statistical Analysis of Relative Expression Results in real-Time PCR", Nucleic Acids Research, 30(9), 2002, 10 pgs.
Philip, J. et al., "Late First-Trimester Invasive Prenatal Diagnosis: Results of an International Randomized Trial", American College of Obstetricians and Gynecologists, vol. 103, No. 6, Jun. 2004, 1164-1173.
Phillips, C. et al., "Resolving Relationship Tests that Show Ambiguous STR Results Using Autosomal SNPs as Supplementary Markers", Forensic Science International: Genetics 2, 2008, 198-204.
Pinard, et al., "Assessment of Whole Genome Amplification-induced Bias Through High-throughput, Massively Parallel Whole Genome Sequencing", BMC Genomics, vol. 7:216, Aug. 23, 2006, 1-21.
Pirker, C. et al., "Whole Genome Amplification for CGH Analysis: Linker-Adapter PCR as the Method of Choice for Difficult and Limited Samples", Cytometry Part A, vol. 61A, 2004, 26-34.
Podder, Mohua et al., "Robust SN P genotyping by multiplex PCR and arrayed primer", BMC Medical Genomics, 1(5), 2008, 1-15.
Poirier, K. et al., "Maternal mosaicism for mutations in the ARX gene in a family with X linked mental retardation", Human Genetics, vol. 118, Aug. 3, 2005, 45-48.
Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.
Poon, L. L. et al., "Differential DNA Methylation between Fetus and Mother as a Strategy for Detecting Fetal DNA in Maternal Plasma", Clinical Chemistry, vol. 48, No. 1, 2002, 35-41.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Porreca, Gregory J et al., "Multiplex Amplification of Large Sets of Human Exons", Nature Methods, 4, (advance online publication), 2007, 6.
Pourmand, et al., "Multiplex Pyrosequencing", Nucleic Acid Research, vol. 30, No. 7, Apr. 1, 2002, 1-5.
Prabhu, et al., "Overlapping Pools for High-throughput Targeted Resequencing", Genome Research, vol. 19, May 15, 2009, 1254-1261.
Price, T.S. et al., "SW-ARRAY: a dynamic programming solution for the identification of copy-number changes in genomic DNA using array comparative genome hybridization data", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Profitt, J. et al., "Isolation And Characterisation of Recombination Events Involving Immunoglobulin Heavy Chain Switch Regions in Multiple Myeloma Using Long Distance Vectorette PCR (Ldv-pcr)", Leukemia, vol. 13, No. 7, Jul. 1999, 1100-1107.
Puszyk, William M. et al., "Noninvasive Prenatal Diagnosis of Aneuploidy Using Cell-free Nucleic Acids in Maternal Blood: Promises and Unanswered Questions", Prenatal Diagnosis, vol. 28, No. 1, Nov. 16, 2007, 1-6.
Qiagen, "QIAamp DNA Mini Kit and QIAamp DNA Blood Mini Kit Handbook", QIAamp DNA Mini Kit and QIAamp DNA Blood Mini Kit Handbook, Feb. 2003 ("Qiagen (2003)"), 2003, 68 pages.
Qin, Z. S. et al., "Partition-Ligation-Expectation-Maximization Algorithm for Haplotype Inference with Single-Nucleotide Polymorphisms", Am. J. Hum Genet., vol. 71, 2002, 1242-1247.
Quan, P. C. et al., "Studies on the mechanism of NK cell lysis", The Journal of Immunology, vol. 128, 1982, 1786-1791.
Quinlan, M. P. , "Amniocentesis: Indications and Risks", American Medical Association Journal of Ethics: Virtual Mentor, vol. 10, No. 5, May 2008, 304-306.
Quinn, G. P. et al., "Experimental Design and Data Analysis for Biologists", Graphical Exploration of Data, 2002, 64-67.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, M. , "A System and Method for Integrating, Validating and Applying Genetic and Clinical Data to Enhance Medical Decisions", Nov. 29, 2005, 155 pgs.
Rabinowitz, Matthew et al., "Origins and rates of aneuploidy inhuman blastomeres", Fertility and Sterility, vol. 97, No. 2, Feb. 2012, 395-401.
Rabinowitz, Matthew et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Ragoussis, J. , "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.
Raindance Technologies, "Multiplexing with RainDrop Digital PCR", Application Note, 2013, 2 pgs.
Raindance Technologies, et al., "RainDance Technologies Introduces the RDT 1000", RainDance Technologies, Nov. 12, 2008,.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Ravipati, Goutham et al., "Comparison of Sensitivity, Specificity, Positive Predictive Value, and Negative Predictive Value of Stress Testing Versus 64-Multislice Coronary Computed Tomography Angiography in Predicting Obstructive Coronary Artery Disease Diagnosed by Coronary Angiogr", The American Journal of Cardiology, Coronary Artery Disease. vol. 101, Issue 6, Mar. 15, 2008, 774-775.
Rechitsky, Svetlana et al., "Preimplantation Genetic Diagnosis with HLA Matching", Reproductive Bio Medicine Online, 9, 2, 2004, 210-221.
Reeves, R. H. et al., "Too much of a good thing: mechanisms of gene action in Down syndrome", Trends in Genetics, vol. 17, No. 2, Feb. 2, 2001, 83-88.
Reinert, T. et al., "Analysis of circulating tumour DNA to monitor disease burden following colorectal cancer surgery", Gut, vol. 65, 2016, 625-634.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.

(56) References Cited

OTHER PUBLICATIONS

Rhoads, A. et al., "PacBio Sequencing and Its Applications", Genomics Proteomics Bioinformatics, vol. 13, Nov. 2, 2015, 278-289.
Ricciotti, Hope , "Eating by Trimester", Online]. Retrieved from Internet:<http://www.youandyourfamily.com/article.php?story=Eating+by+Trimester>, 2014, 3.
Riley, D. E. , "DNA Testing: An Introduction for Non-Scientists an Illustrated Explanation", Scientific Testimony: An Online Journal, http://www.scientific.org/tutorials/articles/riley/riley.html, Apr. 6, 2005, 22 pages.
Riva, F. , "Patient-Specific Circulating Tumor DNA Detection during Neoadjuvant Chemotherapy in Triple-Negative Breast Cancer", Clinical Chemistry, vol. 63, No. 3, 2017, 691-699.
Robertson, G. et al., "Genome-wide profiles of STAT1 DNA association using chromatin immunoprecipitation and massively parallel sequencing", Nature Methods, vol. 4, No. 8, Aug. 2007, 651-657.
Roche Diagnostics, et al., "Versatile Nucleic Acid Purification", MagnaPure Manual, Feb. 3, 2012,.
Rogaeva, E. et al., "The Solved and Unsolved Mysteries of the Genetics of Early-Onset Alzheimer's Disease", NeuroMolecular Medicine, vol. 2, 2002, 1-10.
Roman, B. L. et al., "Non-Radioisotopic AFLP Method Using PCR Primers Fluorescently Labeled with CyA 5", BioTechniques, vol. 26, Feb. 1999, 236-238.
Roper, Stephen M. et al., "Forensic Aspects of DNA-Based Human Identity Testing", Journal of Forensic Nursing, 4, 2008, 150-156.
Rosado, J. A. et al., "Tyrosine kinases activate store-mediated Ca2+ entry in human platelets through the reorganization of the actin cytoskeleton", Biochem. J., vol. 351, 2000, 429-437.
Rosen, D. R. et al., "Mutations in Cu/Zn superoxide dismutase gene are associated with familial amyotrophic lateral sclerosis", Nature, vol. 362, Mar. 4, 1993, 59-62.
Ross, P. et al., "Quantitative Approach to Single-Nucleotide Polymorphism Analysis Using MALDI-TOF Mass Spectrometry", BioTechniques, vol. 29, Sep. 2000, 620-629.
Rothberg, et al., "The Development and Impact of 454 Sequencing", Nature Biotechnology, vol. 26, No. 10, Oct. 9, 2008, 1117-1124.
Roux, K. , "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Ruano, G. et al., "Haplotype of multiple polymorphisms resolved by enzymatic amplification of single DNA molecules", Proc. Nati. Acad. Sci. USA, vol. 87, Aug. 1990, 6296-6300.
Rubio, J. M. et al., "Semi-nested, Multiplex Polymerase Chain Reaction for Detection of Human Malaria Parasites and Evidence of Plasmodium Vivax Infection in Equatorial Guinea", The American Journal of Tropical Medicine And Hygiene, vol. 60, 1999, pp. 183-187.
Ruschendorf, et al., "Alohomora: A Tool for Linkage Analysis Using 10K SNP Array Data", Bioinformatics Applications Notes, vol. 21, No. 9, Jan. 12, 2005, 2123-2125.
Russell, L. M. , "X Chromosome Loss and Ageing", Cytogenetic and Genome Res., 116, 2007, 181-185.
Ryan, A. et al., "Informatics-Based, Highly Accurate, Noninvasive Prenatal Paternity Testing", Genetics in Medicine (advance online publication), 2012, 5 pgs.
Ryan, B. M. et al., "A prospective study of circulating mutant KRAS2 in the serum of patients with colorectal neoplasia: strong prognostic indicator in postoperative follow up", Gut, vol. 52, 2003, 101-108.
Rychlik, et al., "Optimization of the annealing temperature for DNA amplification in vitro", Nucleic Acids Research, 18(21), 1990, 6409-6412.
Sahota, A. , "Evaluation of Seven PCR-Based Assays for the Analysis of Microchimerism", Clinical Biochemistry, vol. 31, No. 8., 1998, 641-645.
Sahukhal, G. S. et al., "msaABCR operon positively regulates biofilm development by repressing proteases and autolysis in *Staphlococcus aureus*", FEMS Microbiology Letters, vol. 362, No. 4, 2015, 1-10.
Saito, H. et al., "Prenatal DNA diagnosis of a single-gene disorder from maternal plasma", The Lancet, vol. 356, Sep. 30, 2000, 1170.
Saker, A. et al., "Genetic characterisation of circulating fetal cells allows non-invasive prenatal diagnosis of cystic fibrosis", Prenatal Diagnosis, vol. 26, Jul. 11, 2006, 906-916.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.
Sanchez, C. et al., "New insights into structural features and optimal detection of circulating tumor DNA determined by single-strand DNA analysis", Nature Partner Journals, vol. 3, No. 31, Nov. 23, 2018, 12 pgs.
Sander, Chris , "Genetic Medicine and the Future of Health Care", Science, 287(5460), 2000, 1977-1978.
Sanger, et al., "Nucleotide Sequence of Bacteriophage Lambda DNA", Journal of Molecular Biology, vol. 162, No. 4, Dec. 25, 1982, 729-773.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Santalucia, Jr., J. , "Physical Principles and Visual-OMP Software for Optimal PCR Design", Methods in Molecular Biology, vol. 402, 2007, 3-33.
Sasabe, Yutaka , "Genetic Diagnosis of Gametes and Embryos Resulting from ART", Japanese Journal of Fertility and Sterility, vol. 46, No. 1, 2001, 43-46.
Scarpa, A. et al., "Molecular Typing of Lung Adenocarcinoma on Cytological Samples Using a Multigene Next Generation Sequencing Panel", PLOS One, vol. 8, No. 11, Nov. 13, 2013, 6 pgs.
Schaaf, C. P. et al., "Copy Number and SNP Arrays in Clinical Diagnostics", Annu. Rev. Genomics Hum. Genet., vol. 12, 2011, 25-51.
Scheet, P. et al., "A Fast and Flexible Statistical Model for Large-Scale Population Genotype Data: Applications to Inferring Missing Genotypes and Haplotypic Phase", The American Journal of Human Genetics, vol. 78, Apr. 2006, 629-644.
Schmitt, M. W. et al., "Detection of ultra-rare mutations by next-generation sequencing", PNAS, vol. 109, No. 36, Sep. 4, 2012, 14508-14513.
Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.
Schoumans, J et al., "Detection of chromosomal imbalances in children with idiopathic mental retardation by array based comparative genomic hybridisation (array-CGH)", JMed Genet, 42, 2005, 699-705.
Schubert, "Picking out prenatal DNA", Nature Medicine, vol. 10, No. 785, Aug. 2004, 1 page.
Schwarzenbach, H. et al., "Cell~free nucleic acids as biomarkers in cancer patients", Nature Reviews: Cancer, vol. 11, Jun. 2011, 426-437.
Schwarzenbach, H. et al., "Detection and Characterization of Circulating Microsatellite-DNA in Blood of Patients with Breast Cancer", Ann. N.Y. Acad. Sci., vol. 1022, 2004, 25-32.
Schwarzenbach, H. et al., "Evaluation of cell-free tumour DNA and RNA in patients with breast cancer and benign breast disease", Molecular BioSystems, vol. 7, 2011, 2848-2854.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.

(56) References Cited

OTHER PUBLICATIONS

Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Sham, P. et al., "DNA Pooling: A Tool for Large-Scale Association Studies", Nature Reviews Genetics, vol. 3, Nov. 2002, 862-871.
Shapero, M. H. et al., "Mara: A Novel Approach for Highly Multiplexed Locus-specific SNP Genotyping Using High-density DNA Oligonucleotide Arrays", Nucleic Acids Research, vol. 32, No. 22, 2004, 1-9.
Sharples, et al., "Diagnostic Accuracy of Coronary Angiography and Risk Factors for Post-heart-transplant Cardiac Allograft Vasculopathy", Transplantation, vol. 76, No. 4, Aug. 27, 2003, 679-682.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, R. et al., "High-throughput SNP genotyping on universal bead arrays", Mutation Research, vol. 573, Feb. 11, 2005, 70-82.
Shen, Zhiyong , "MPprimer: a program for reliable multiplex PCR primer design", BMC Bioinformatics 2010, 11:143, 1-7.
Shendure, J. et al., "Accurate Multiplex Polony Sequencing of an Evolved Bacterial Genome", Science, Nov. 30, 2007, 18-24.
Shendure, J. et al., "Next-generation DNA sequencing", Nature Biotechnology, vol. 26, No. 10, Oct. 2008, 1135-1145.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Shinozaki, M. et al., "Utility of Circulating B-RAF DNA Mutation in Serum for Monitoring Melanoma Patients Receiving Biochemotherapy", Clin Cancer Res, vol. 13, No. 7, Apr. 1, 2007, 2068-2074.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Shokralla, S. et al., "Next-generation DNA barcoding: using next-generation sequencing to enhance and accelerate DNA barcode capture from single specimens", Molecular Ecology Resources, vol. 14, 2014, 892-901.
Short, N. J. et al., "Targeted next-generation sequencing of circulating cell-free DNA vs bone marrow in patients with acute myeloid leukemia", Blood Advances, vol. 4, No. 8, Apr. 23, 2020, 1670-1677.
Shyamala, Venkatakrishna et al., "Genome Walking by Single-Specific-Primer Polymerase Chain Reaction: SSP-PCR", Gene, vol. 84, 1989, pp. 1-8.
Siebert, P. D. et al., "An improved PCR method for walking in uncloned genomic DNA", Nucleic Acids Research, vol. 23, No. 6, 1995, 1087-1088.
Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.
Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.
Simpson, J. et al., "Fetal Cells in Maternal Blood: Overview and Historical Perspective", Annals New York Academy of Sciences, 731, 1994, 1-8.
Singh, Vinayak K. et al., "PCR Primer Design", Molecular Biology Today, vol. 2, 2001, pp. 27-32.
Sint, Daniela et al., "Advances in Multiplex PCR: Balancing Primer Efficiencies and Improving Detection Success", Methods in Ecology and Evolution, 3, 2012, 898-905.
Sivertsson, A. et al., "Pyrosequencing as an Alternative to Single-Strand Conformation Polymorphism Analysis for Detection of N-ras Mutations in Human Melanoma Metastases", Clinical Chemistry, vol. 48, No. 12, 2002, 2164-2170.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Smith, et al., "Rapid Whole-genome Mutational Profiling using Next-generation Sequencing Technologies", Genome Research, vol. 18, Sep. 4, 2008, 1638-1642.
Smith, James F. et al., "Cell-free Fetal DNA in Maternal Plasma", Neo Reviews, vol. 9, No. 8, Aug. 1, 2008, e332-e337.
Snijders, Antoine et al., "Assembly of Microarrays for Genome-Wide Measurement of DNA Copy Number", Nature Genetic, 29, 2001, 263-264.
Snyder, T. M. et al., "Universal noninvasive detection of solid organ transplant rejection", PNAS, vol. 108, No. 15, Apr. 12, 2011, 6229-6234.
Societies Related to Genetic Med, , "Guideline related to genetic examination", Japanese Society for Genetic Counseling, Japanese Society for Gene Diagnosis and Therapy, Japan Society of Obstetrics and Gynecology, 2003, 2-15.
Solexa, "Application Note: DNA Sequencing", 2006, 1-2.
Solomon, M. J. et al., "Formaldehyde-mediated DNA-protein crosslinking: A probe for in vivo chromatin structures", Proc. Natl. Acad. Sci. USA, vol. 82, 1985, 6470-6474.
Sorenson, G. D. et al., "Soluble Normal and Mutated DNA Sequences from Single-Copy Genes in Human Blood", Cancer Epdemiology, Biomarkers & Prevention, vol. 3, Jan./Feb. 1994, 67-71.
Sourceforge.net, "Primer3", 2009, 1 pg.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1--319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spencer, K. et al., "Maternal serum levels of dimeric inhibin A in pregnancies affected by trisomy 21 in the first trimester", Prenatal Diagnosis, vol. 21, 2001, 441-444.
Spencer, K. et al., "Maternal serum levels of total activin-A in first-trimester trisomy 21 pregnancies", Prenatal Diagnosis, vol. 21, 2001, 270-273.
Spertini, D. et al., "Screening of Transgenic Plants by Amplification of Unknown Genomic DNA Flanking T-DNA", BioTechniques, vol. 27, Aug. 1999, 308-314.
Spes, et al., "Diagnostic and Prognostic Value of Serial Dobutamine Stress Echocardiography for Noninvasive Assessment of Cardiac Allograft Vasculopathy: A Comparison With Coronary Angiography and Intravascular Ultrasound", Circulation, vol. 100, No. 5, Aug. 3, 1999, 509-515.
Spindler, K.L. G. et al., "Cell-free DNA in healthy individuals, noncancerous disease and strong prognostic value in colorectal cancer", International Journal of Cancer, vol. 135, 2014, 2984-2991.
Spindler, K.-L. G. et al., "Cell-Free DNA in Metastatic Colorectal Cancer: A Systematic Review and Meta-Analysis", The Oncologist, vol. 22, 2017, 1049-1055.

(56) References Cited

OTHER PUBLICATIONS

Spiro, Alexander et al., "A Bead-Based Method for Multiplexed Identification and Quantitation of DNA Sequences Using Flow Cytometry", Applied and Environmental Microbiology, 66, 10, 2000, 4258-4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, M. et al., "Accounting for Decay of Linkage Disequilibrium in Haplotype Inference and Missing-Data Imputation", Am. J. Hum. Genet., vol. 76, 2005, 449-462.
Stephens, Mathews et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Stewart, C. M. et al., "Circulating cell-free DNA for non-invasive cancer management", Cancer Genetics, vol. 228-229, 2018, 169-179.
Stewart, S. et al., "Revision of the 1990 Working Formulation for the Standardization of Nomenclature in the Diagnosis of Heart Rejection", The Journal of Heart and Lung Transplantation, vol. 24, No. 11, Nov. 2005, 1710-1720.
Steyerberg, E.W et al., "Application of Shrinkage Techniques in Logistic Regression Analysis: A Case Study", Statistica Neerlandica, 55(1), 2001, 76-88.
Stiller, et al., "Direct Multiplex Sequencing (DMPS)—A Novel Method for Targeted High-thoroughput Sequencing of Ancient and Highly Degraded DNA", Genome Research, vol. 19, No. 10, Jul. 27, 2009, 1843-1848.
Stolerman, Elliot S. et al., "Haplotype structure of the ENPP1 Gene and Nominal Association of the K121Q missense single nucleotide polymorphism with glycemic traits in the Framingham Heart Study", Diabetes, vol. 57, Issue 7, Jul. 1, 2008, 1971-1977.
Stone, J. P. et al., "Ex Vivo Normothermic Perfusion Induces Donor-Derived Leukocyte Mobilization and Removal Prior to Renal Transplantation", Kidney Int Rep., vol. 1, No. 4, Aug. 6, 2016, 230-239.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., ""Inferring combined CNV/SNP haplotypes from genotype data"", Bioinformatics, vol. 26, No. 11,1, Jun. 1, 2010, 1437-1445.
Su, Z. et al., "A Platform for Rapid Detection of Multiple Oncogenic Mutations With Relevance to Targeted Therapy in Non-Small-Cell Lung Cancer", The Journal of Molecular Diagnostics,, vol. 13, No. 1, Jan. 2011, 74-84.
Sun, Guihua et al., "SNPs in human miRNA genes affect biogenesis and function", RNA, 15(9), 2009, 1640-1651.
Swarup, V. et al., "Circulating (cell-free) nucleic acids - A promising, non-invasive tool for early detection of several human diseases", FEBS Letters, vol. 581, 2007, 795-799.
Sweet-Kind Singer, J. A. et al., "Log-penalized linear regression", IEEE International Symposium on Information Theory, 2003. Proceedings, 2003, 286.
Swinkels, D. W. et al., "Effects of Blood-Processing Protocols on Cell-free DNA Quantification in Plasma", Clinical Chemistry, vol. 49, No. 3, 2003, 525-526.
Syvanen, A.C. , "Toward genome-wide SNP genotyping", Nature Genetics Supplement, vol. 37, Jun. 2005, S5-S10.
Taback, B. et al., "Quantification of Circulating DNA in the Plasma and Serum of Cancer Patients", Ann. N.Y. Acad. Sci, vol. 1022, 2004, 17-24.
Takala, et al., "A High-throughput Method for Quantifying Alleles and Haplotypes of The Malaria Vaccine Candidate Plasmodium Falciparum Merozoite Surface Protein-1 19 kDa", Malaria Journal, vol. 5:31, Apr. 20, 2006, 1-10.
Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.
Takara Biomedicals, "Competitive PCR Guide", Lit. # L0126, Aug. 1999, 9 pages.
Takashima, Y. et al., "Expansion-contraction of photoresponsive artificial muscle regulated by host-guest interactions", Nature Communications, vol. 3, No. 1270, Dec. 11, 2012, 8 pages.
Taliun, D. et al., "Efficient haplotype block recognition of very long and dense genetic sequences", BMC Bioinformatics, vol. 15 (10), 2014, 1-18.
Tamura, et al., "Sibling Incest and formulation of paternity probability: case report", Legal Medicine, 2000, vol. 2, p. 189-196.
Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v. 144, No. 1, p. 35-39.,.
Tang, N. et al., "Detection of Fetal-Derived Paternally Inherited X-Chromosome Polymorphisms in Maternal Plasma", Clinical Chemistry, 45 (11), 1999, 2033-2035.
Tebbutt, S. J. et al., "Microarray genotyping resource to determine population stratification in genetic association studies of complex disease", BioTechniques, vol. 37, Dec. 2004, 977-985.
Ten Bosch, J. , "Keeping Up With the Next Generation Massively Parallel Sequencing in Clinical Diagnostics", Journal of Molecular Diagnostics, vol. 10, No. 6, 2008, 484-492.
Tewhey, R. et al., "Microdroplet-based PCR enrichment for large-scale targeted sequencing", Nature Biotechnology, vol. 27, No. 11, Nov. 2009, 1025-1031.
Tewhey, R. et al., "The importance of phase information for human genomics", Nature Reviews Genetics, vol. 12, No. 3, Mar. 1, 2011, 215-223.
Thavarajah, R. et al., "Chemical and physical basics of routine formaldehyde fixation", Journal of Oral and Maxillofacial Pathology, vol. 16, No. 3, 2012, 400-405.
The Bump Message Boards, The Bump (Panorama Test, attached), Jul. 1, 2013, 8 pages.
The International Hapmap Consort, "The International HapMap Project", Nature, vol. 426, Dec. 18, 2003, 789-796.
Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Thomas, M.R et al., "The Time of Appearance and Disappearance of Fetal DNA from the Maternal Circulation", Prenatal Diagnosis, 15, 1995, 641-646.
Thompson, J. C. et al., "Detection of Therapeutically Targetable Driver and Resistance Mutations in Lung Cancer Patients by Next-Generation Sequencing of Cell-Free Circulating Tumor DNA", Clin Cancer Res, vol. 22, No. 23, Dec. 1, 2016, 5772-5782.
Thornton, Brenda et al., "Real-time Pcr (qPCR) Primer Design Using Free Online Software", Biochemistry and Molecular Biology Education, vol. 39, 2011, pp. 145-154.
Tiersch, T. R. et al., "Reference Standards for Flow Cytometry and Application in Comparative Studies of Nuclear DNA Content", Cytometry, vol. 10, Mar. 21, 1989, 706-710.
Tong, et al., "Diagnostic Developments Involving Cell-free (Circulating) Nucleic Acids", Clinica Chimica Acta, vol. 363, No. (1-2), Aug. 26, 2005, 187-196.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.

(56) References Cited

OTHER PUBLICATIONS

Tong, Yu K. et al., "Noninvasive Prenatal Detection of Trisomy 21 by Epigenetic-Genetic Chromosome-Dosage Approach", Clinical Chemistry, 56(1), 2010, 90-98.
Toshikazu, et al., "Estimation of Haplotype Frequencies, Linkage-disequilibrium Measures, and Combination of Haplotype Copies in Each Pool by Use of Pooled DNA Data", American Journal of Human Genetics, vol. 72, Jan. 17, 2003, 384-398.
Tounta, G et al., "Non-invasive prenatal diagnosis using cell-free fetal nucleic acids in maternal plasma: Progress overview beyond predictive and personalized diagnosis", EPMA Journal, vol. 2, Issue 2, 2011, 163-171.
Tounta, G. et al., "A Multiplex PCR for Non-invasive Fetal RHD Genotyping Using Cell-free Fetal DNA", in vivo, vol. 25, 2011, 411-418.
Treff, N. R. et al., "Single Cell Whole Genome Amplification Technique Significantly Impacts the Accuracy and Precision of Microarray Based 23 Chromosome Aneuploidy Screening", Poster Presentations Preimplantation Genetic Diagnosis, vol. 88, Supplement 1, Sep. 1, 2007, S231.
Troeger, C. et al., "Approximately Half of The Erythroblasts in Maternal Blood are of Fetal Origin", Molecular Human Reproduction, vol. 5, No. 12, Dec. 1, 1999, 1162-1165.
Troutt, et al., "Ligation-anchored PCR: A Simple Amplification Technique with Single-sided Specificity", Proceedings of the National Academy of Sciences, vol. 89, Oct. 1992, 9823-9825.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsang, Jason C. et al., "Circulating Nucleic Acids in Plasma/Serum", Pathology, vol. 39, No. 2, Apr. 1, 2007, 197-207.
Tsangaris, G. T. et al., "Proteomic analysis of amniotic fluid in pregnancies with Down syndrome", Proteomics, vol. 6, 2006, 4410-4419.
Tsui, N. B. et al., "Systematic micro-array based identification of placental mRNA in maternal plasma: towards non-invasive prenatal gene expression profiling", J. Med. Genet, vol. 41, 2004, 461-467.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Tu, J. et al., "Pair-barcode high-throughput sequencing for large-scale multiplexed sample analysis", BMC Genomics, vol. 13, No. 43, Jan. 25, 2012, 1-9.
Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.
Turner, E. et al., "Massively Parallel Exon Capture and Library-Free Resequencing Across 16 Genomes", Nature Methods, 6 (5), 2009, 315- 316.
Tuzcu, et al., "Intravascular Ultrasound Evidence of Angiographically Silent Progression in Coronary Atherosclerosis Predicts Long-term Morbidity and Mortality After Cardiac Transplantation", The American Journal of Cardiology, vol. 45, No. 9, May 3, 2005, 1538-1542.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Tzimagiorgis, G. et al., "Recovering circulating extracellular or cell- free RNA from bodily fluids", Cancer Epidemiology, vol. 35, 2011, 580- 589.
Umetani, N. et al., "Increased Integrity of Free Circulating DNA in Sera of Patients with Colorectal or Periampullary Cancer: Direct Quantitative PCR for ALU Repeats", Clinical Chemistry, vol. 52, No. 6, 2006, 1062-1069.
Urbaniak, S. J. et al., "RhD haemolytic disease of the fetus and the newborn", Blood Reviews, vol. 14, 2000, 44-61.
Urbanova, M. et al., "Circulating Nucleic Acids as a New Diagnostic Tool", Cellular & Molecular Biology Letters, vol. 15, 2010, 242-259.
Vallone, P. M. et al., "A multiplex allele-specific primer extension assay for forensically informative SNPs distributed throughout the mitochondrial genome", Int J Legal Medicine, vol. 118, Feb. 4, 2004, 147-157.
Vallone, Peter , "AutoDimer: a Screening Tool for Primer-Dimer and Hairpin Structures", Bio Techniques, 37, 2004, 226-231.
Vallone, Peter M. et al., "Demonstration of Rapid Multiplex PCR Amplification Involving 16 Genetic Loci", Forensic Science International: Genetics, vol. 3, 2008, pp. 42-45.
Van Den Oever, J. M. et al., "Single Molecule Sequencing of Free DNA from Maternal Plasma for Noninvasive Trisomy 21 Detection", Clinical Chemistry, vol. 58, No. 4, 2012, 699-706.
Van Uitert, I. et al., "The influence of different membrane components on the electrical stability of bilayer lipid membranes", Biochimica et Biophysica Acta, vol. 1798, 2010, 21-31.
Vanneste, Marion et al., "Functional Genomic Screening Independently Identifies CUL3 as a Mediator of Vemurafenib Resistance via Src-RAC1 Signaling Axis", Frontiers in Oncology, vol. 10, 2020, 16 pages.
Varley, Katherine Elena et al., "Nested Patch PCR Enables Highly Multiplexed Mutation Discovery in Candidate Genes", Genome Res., 18(11), 2008, 1844-1850.
Verlaan, et al., "Allele-specific Chromatin Remodeling in the ZPBP22/GSDMB/ORMDL3 Locus Associated with the Risk of Asthma and Autoimmune Disease", The American Journal of Human Genetics, vol. 85, No. 3, Sep. 11, 2009, 377-393.
Verlaan, et al., "Targeted Screening of Cis-Regulatory Variation in Human Haplotypes", Genome Research, vol. 19, No. 1, Jan. 1, 2009, 118-127.
Verlinsky, Y. et al., "Over a Decade of Experience with Preimplantation Genetic Diagnosis", Fertility and Sterility, 82 (2), 2004, 302-303.
Vlaminck, I. D. et al., "Circulating Cell-Free DNA Enables Non-invasive Diagnosis of Heart Transplant Rejection", Sci Transl Med., vol. 6, No. 241, Jun. 18, 2018, 26 pages.
Voelkerding, et al., "Next-generation Sequencing: From Basic Research to Diagnostics", Clinical Chemistry, vol. 55, No. 4, Apr. 1, 2009, 641-658.
Vogelstein, B. et al., "Digital PCR", Proc. Natl. Acad. Sci. USA, vol. 96, Aug. 1999, 9236-9241.
Von Ahsen, Nicolas et al., "Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas", Clinical Chemistry, vol. 47, 2001, pp. 1956-1961.
Von Eggeling, F. et al., "Applications of Random PCR", Cellular and Molecular Biology, vol. 41, No. 5, 1995, 653-670.
Wagner, Jasenka et al., "Non-Invasive Prenatal Paternity Testing from Maternal Blood", Int. J. Legal Med., 123, 2009, 75-79.
Wang, D. G. et al., "Large-Scale Identification, Mapping, and Genotyping of Single-Nucleotide Polymorphisms in the Human Genome", Science, vol. 280, May 15, 1998, 1077-1082.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, J. et al., "Genome-wide Single-Cell Analysis of Recombination Activity and De Novo Mutation Rates in Human Sperm", Cell, vol. 150, Jul. 20, 2012, 402-412.
Wang, S. et al., "Potential Clinical Significance of a Plasma-Based KRAS Mutation Analysis in Patients with Advanced Non-Small Cell Lung Cancer", Clin Cancer Res, vol. 16, No. 4, Feb. 15, 2010, 1324-1330.
Wang, T.L. et al., "Digital karyotyping", PNAS, vol. 99, No. 25, Dec. 10, 2002, 16156-16161.
Wang, W.-P. et al., "Multiplex single nucleotide polymorphism genotyping by adapter ligation-mediated allele-specific amplification", Analytical Biochemistry, vol. 355, May 5, 2006, 240-248.

(56) References Cited

OTHER PUBLICATIONS

Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Wapner, R. et al., "First-Trimester Screening for Trisomies 21 and 18", The New England Journal of Medicine, vol. 349, No. 15, Oct. 9, 2003, 1405-1413.
Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.
Wartell, Roger M. et al., "Thermal Denaturation of DNA Molecules: A Comparison of Theory with Experiment", Physics Reports, vol. 126, 1985, pp. 67-107.
Wasson, Jon et al., "Assessing Allele Frequencies of Single Nucleotide Polymorphisms in DNA Pools by Pyrosequencing Technology", BioTechniques, vol. 32, No. 5, May 1, 2002, 1144-1152.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Watt, Heather L. , "Sex Diagnosis of Preimplantation Porcine Embryos through PCR Amplification of the Sry Gene", Sex Diagnosis of Preimplantation Porcine Embryos Through PCR Amplification of the SRY Gene (1998) ("Watt (1998)"), 1998, 151 pages.
Wei, C. et al., "Detection and Quantification by Homogeneous PCR of Cell-free Fetal DNA in Maternal Plasma", Clinical Chemistry, vol. 47, No. 2, 2001, 336-338.
Wei, Ting et al., "Novel Approaches to Mitigate Primer Interaction and Eliminate Inhibitors in Multiplex PCR, Demonstrated Using an Assay for Detection of three Strawberry Viruses", Journal of Virological Methods, vol. 151, 2008, pp. 132-139.
Weiss, C. A. , "Chapter 8: Confidence Intervals for One Population Mean", Introductory Statistics, Sixth Edition, 2002, 340-381.
Wellnhofer, et al., "Angiographic Assessment of Cardiac Allograft Vasculopathy: Results of a Consensus Conference of the Task Force for Thoracic Organ Transplantation of the German Cardiac Society", Transplant International, vol. 23, No. 11, Aug. 19, 2010, 1094-1104.
Wells, D , "Microarray for Analysis and Diagnosis of Human Embryos", 12th International Congress on Prenatal Diagnosis and Therapy, Budapest, Hungary, 2004, 9-17.
Wells, Dagan , "Advances in Preimplantation Genetic Diagnosis", European Journal of Obstetrics and Gynecology and Reproductive Biology, 115S, 2004, S97-S101.
Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), NULL, 2012, 1-9.
What to Expect Message Boards, What to Expect (Weird Harmony results), May 1, 2015, 7 pages.
Widlak, P. et al., "Cleavage Preferences of the Apoptotic Endonuclease DFF 40 (Caspase~activated DNase or Nuclease) on Naked DNA and Chromatin Substrates", The Journal of Biological Chemistry, vol. 275, No. 11, Mar. 17, 2000, 8228-8232.
Wiedmann, Ralph T. et al., "SNP Discovery in Swine by Reduced Representation and High Throughput Pyrosequencing", BMC Genetics, vol. 9, Article No. 81, Dec. 4, 2008, 1-7.
Wikipedia, "Buffy coat", Retrieved from "https://en.wikipedia.orgJw/index.php?title=Buffy_coat&oldid=900992886", Jun. 9, 2019, 2 pgs.
Wikipedia, "Maximum a posteriori estimation", https://en.wikipedia.org/w/index.php?title=Maximum_a_posteriori_estimat ion&oldid=26878808, [retrieved on Aug. 1, 2017], Oct. 30, 2005, 2 pages.
Wikipedia, "Stimulant", 17 pages.
Wilkening, Stefan et al., "Determination of Allele Frequency in Pooled DNA: Comparison of Three PCR-based Methods", Bio Techniques, vol. 39, No. 6, May 30, 2005, 853-857.
Wilkinson, Sarah T. et al., "Decreased MHC Class II Expression in Diffuse Large B-Cell Lymphoma does not Correlate with CPG Methylation of Ciita Promoters III and IV", Leuk Lymphoma, vol. 50, 2009, pp. 1875-1878.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L. , "Preimplantation Genetic Diagnosis and Chromosome Analysis of Blastomeres Using Comparative Genomic Hybridization", Human Reproduction Update, 11 (1), 2005, 33-41.
Winsor, E. J. et al., "Maternal Cell Contamination in Uncultured Amniotic Fluid", Prenatal Diagnosis, vol. 16, 1996, 49-54.
Witherspoon, David J. et al., "Mobile Element Scanning (Me-scan) by Targeted High-throughput Sequencing", BMC Genomics, vol. 410, 2010, 15 pages.
Wittwer, C. T. et al., "Real-Time Multiplex PCR Assays", Methods, vol. 25, 2001, 430-448.
Wong, K. H. et al., "Multiplex Illumina Sequencing Using DNA Barcoding", Current Protocols in Molecular Biology, vol. 101, Jan. 2013, 7.11.1-7.11.11.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wright, Caroline et al., "Cell-free Fetal Nucleic Acids for Noninvasive Prenatal Diagnosis", PHG Foundation, Jan. 1, 2009, 1-64.
Wu, T.L. et al., "Cell-free DNA: measurement in various carcinomas and establishment of normal reference range", Clinica Chimica Acta, vol. 321, 2002, 77-87.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, et al., "Simultaneous Quantitative Assessment of Circulating Cell-free Mitochondrial and Nuclear DNA by Multiplex Real-time PCR", Genetics and Molecular Biology, vol. 32, No. 1, Mar. 1, 2009, 20-24.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Xian, et al., "Advances On Circulating Fetal DNA in Maternal Plasma", Chinese Medical Journal, vol. 120, No. 14, Jul. 2, 2007, 1256-1259.
Xie, et al., "CNV-SEQ, A New Method to Detect Copy Number Variation Using Highthroughput Sequencing", BMC Bioinformatics, vol. 10:80, Mar. 6, 2009, 1-9.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Xu, S. et al., "Circulating tumor DNA identified by targeted sequencing in advanced-stage non-small cell lung cancer patients", Cancer Letters, vol. 370, 2016, 324-331.
Xu, W. et al., "A Novel Universal Primer-Multiplex-PCR Method with Sequencing Gel Electrophoresis Analysis", PLOS One, vol. 7, No. 1, Jan. 17, 2012, 10 pgs.
Xue, et al., "Optimizing The Yield And Utility Of Circulating Cell-free DNA From Plasma And Serum", Clinica Chimica Acta, vol. 404, No. 2, Jun. 27, 2009, 100-104.
Yamada, T. et al., "Detection of K-ras Gene Mutations in Plasma DNA of Patients with Pancreatic Adenocarcinoma: Correlation with Clinicopathological Features", Clinical Cancer Research, vol. 4, Jun. 1998, 1527-1532.

(56) References Cited

OTHER PUBLICATIONS

Yamada, T. et al., "PrimerStation: a highly specific multiplex genomic PCR primer design server for the human genome", Nucleic Acids Research, vol. 34, 2006, W665-W669.
Yang, Lin et al., "64-MDCT Coronary Angiography of Patients With Atrial Fibrillation: Influence of Heart Rate on Image Quality and Efficacy in Evalution of Coronary Artery Disease", AJR, vol. 193, No. 3, Sep. 1, 2009, 795-801.
Yaron, Y. , "The implications of non-invasive prenatal testing failures: a review of an under-discussed phenomenon", Prenatal Diagnosis, vol. 36, 2016, 391-396.
Yeh, Iwei et al., "Knowledge Acquisition, Consistency Checking and Concurrency Control for Gene Ontology (GO)", Bioinformatics, 19, 2, 2003, 241-248.
Yijen, et al., "Noninvasive Evaluation of Cardiac Allograft Rejection by Cellular and Functional Cardiac Magnetic Resonance", JACC: Cardiovacular Imaging, vol. 2, No. 6, Jun. 1, 2009, 731-741.
Yilmaz, A. et al., "Comparative Evaluation of Left and Right Ventricular Endomyocardial Biopsy", Circulation, vol. 122, No. 9, Aug. 31, 2010, 900-909.
You, Frank M. et al., "BatchPrimer3: A high throughput web application for PCR and sequencing primer design", BMC Bioinformatics, BIOMED Central, London, GB, vol. 9, No. 1, May 29, 2008 (May 29, 2008), p. 253.
Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Yuanxin, Yan et al., "T-linker-specific Ligation PCR (T-linker Pcr): An Advanced PCR Technique for Chromosome Walking or for Isolation of Tagged DNA Ends", Nucleic Acids Research, vol. 31, No. 12, e68, 2003, 7 pages.
Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.
Zachariah, R. et al., "Circulating cell-free DNA as a potential biomarker for minimal and mild endometriosis", Reproductive BioMedicine Online, vol. 18, No. 3, Jan. 27, 2009, 4007-411.
Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.
Zhang, et al., "Use of PCR and PCR-SSP for Detection of Urinary Donor-Origin DNA in Renal Transplant Recipients With Acute Rejection", Chinese Medical Journal, vol. 116, No. 2, Feb. 2003, 191-194.
Zhang, J. et al., "Presence of Donor-and Recipient-derived DNA in Cell-free Urine Samples of Renal Transplantation Recipients: Urinary DNA Chimerism", Clinical Chemistry, vol. 45, No. 10, 1999, 1741-1746.
Zhang, Kun et al., "Digital RNA Alleotyping Reveals Tissue-specific and Allele-specific Gene Expression in Human", Nature Methods, vol. 6, No. 8, Jul. 20, 2009, 613-618.
Zhang, L. et al., "Whole genome amplification from a single cell: Implications for genetic analysis", Proc. Nat'l. Acad. Sci. USA, vol. 89, Jul. 1992, 5847-5851.
Zhang, Rui et al., "Quantifying RNA allelic ratios by microfluidic multiplex PCR and sequencing", Nature Methods, 11(1), 2014, 51-56.
Zhao, et al., "Urinary Thromboxane B2 in Cardiac Transplant Patients as a Screening Method of Rejection", Prostaglandins, vol. 54, No. 6, Dec. 1, 1997, 881-889.
Zhao, Xiaojun et al., "An Integrated View of Copy Number and Allelic Alterations in the Cancer Genome Using Single Nucleotide Polymorphism Arrays", Cancer Research, 64, 2004, 3060-3071.
Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.
Zheng, Z et al., "Anchored Multiplex PCR for Targeted Next-generation Sequencing", Nature Medicine, vol. 20, No. 12, Dec. 2014, 1479-1486.
Zhong, X Y. et al., "Detection of Fetal Rhesus D And Sex Using Fetal DNA from Maternal Plasma by Multiplex Polymerase Chain Reaction", British Journal of Obstetrics and Gynaecology, vol. 107, Jun. 2000, 766-769.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
Zhong, Xiao Y. et al., "Cell-free DNA In Urine: A Marker for Kidney Graft Rejection, but Not for Prenatal Diagnosis ?", Annals of the New York Academy of Sciences, vol. 945, Sep. 1, 2001, 250-257.
Zhou, et al., "Pyrosequencing, a High-throughput Method For Detecting Single Nucleotide Polymorphisms in the Dihydrofolate Reductase and Dihydropteroate Synthetase Genes of Plasmodiym Falciparum", Journal of Clinical Microbiology, vol. 44, No. 11, Nov. 1, 2006, 3900-3910.
Zhou, W. et al., "Counting Alleles Reveals a Connection Between Chromosome 18q Loss and Vascular Invasion", Nature Biotechnology, 19, 2001, 78-81.
Zhou, W. et al., "Counting alleles to predict recurrence of early-stage colorectal cancers", The Lancet, vol. 359, Jan. 19, 2002, 219-225.
Zimmer, et al., "Transplant Coronary Artery Disease", JACC: Cardiovascular Interventions, vol. 3, No. 4, Apr. 1, 2010, 367-377.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Zimmermann, B. , "Declaration Under 37 CFR 1.32", filed in U.S. Appl. No. 14/171,587, filed Feb. 3, 2014, 4 pgs.
Zimmermann, B. et al., "Digital PCR: a powerful new tool for noninvasive prenatal diagnosis?", Prenatal Diagnosis, vol. 28, Nov. 10, 2008, 1087-1093.
Zimmermann, B. , "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.
Zimmermann, B. et al., "Novel Real-Time Quantitative PCR Test for Trisomy 21", Clinical Chemistry, vol. 48, No. 2, 2002, 362-363.
Zimmermann, B. et al., "Optimized Real-Time Quantitative PCR Measurement of Male Fetal DNA in Maternal Plasma", Clinical Chemistry, vol. 51, No. 9, 2005, 1598-1604.
Zimmermann, B. et al., "Real-Time Quantitative Polymerase Chain Reaction Measurement of Male Fetal DNA in Maternal Plasma", Methods in Molecular Medicine, vol. 132, 2007, 43-49.
Zimmermann, B. et al., "Use of Real-Time Polymerase Chain Reaction for the Detection of Fetal Aneuploidies", Methods in Molecular Biology, vol. 336, Feb. 2006, 83-100.
Zlotogora, J. , "Penetrance and expressivity in the molecular age", Genetics in Medicine, vol. 5, No. 5, 2003, 347-352.
Agbor-Enoh, Sean et al., "Circulating cell free DNA as a biomarker of tissue injury: Assessment in a cardiac xenotransplantation model", Journal of Heart and Long Transplantation, vol. 37, No. 8, 2018, 967-975.
Ali, N. M. et al., "Fetal and Donor-Derived Cell-Free Dna May Assist in Differentiating Pregnancy Related Changes from Allograft Rejection in Kidney Transplant Recipients", American Journal of Transplantation, vol. 23, No. 6, Poster Abstract., 2023.
Antoniou, A. et al., "Data augmentation generative adversarial networks.", arXiv preprint arXiv:1711.04340, (Year: 2017), Nov. 12, 2017, 14 pages.
Li, Ying et al., "Biochemical and Clinical Diagnostic Aspects of Circulating Nucleic Acids", Dissertation, 2005, 103 Pages.
Liao, W et al., "Noninvasive detection of tumor-associated mutations from circulating cell-free DNA in hepatocellular carcinoma patients by targeted deep sequencing.", Oncotarget, 7(26), (Year: 2016), Jun. 28, 2016, 40481-40490.
Malapelle, U. et al., "Next generation sequencing techniques in liquid biopsy: focus on non-small cell lung cancer patients.", Transl Lung Cancer Res., 5(5), (Year: 2016), Oct. 2016, 505-510.

(56) References Cited

OTHER PUBLICATIONS

Min, S. et al., "Deep learning in bioinformatics.", Brief Bioinform., 18(5), (Year: 2017), Sep. 1, 2017, 851-869.
Moscow, J. A. et al., "Engraftment of MDR1 and NeoR Gene-Transduced Hematopoietic Cells After Breast Cancer Chemotherapy", Blood, vol. 94, No. 1, 1999, 52-61.
Neocleous, A. C. et al., "First Trimester Noninvasive Prenatal Diagnosis: A Computational Intelligence Approach", in IEEE Journal of Biomedical and Health Informatics, vol. 20, No. 5, (Year: 2016), Sep. 2016, pp. 1427-1438.
Oustimov, A. , "Artificial neural networks in the cancer genomics frontier.", Translational cancer research., 3(3), (Year: 2014), Jun. 2014, 11 pages.
Puszyk, William , "Epigenetics of cell-free plasma DNA for non-invasive prenatal diagnosis of fetal aneuploidies", Diss. University of Warwick, 2008, 199 pages.
Stephens, Z. D. et al., "Simulating Next-Generation Sequencing Datasets from Empirical Mutation and Sequencing Models.", PLoS One., 11(11):e0167047. (Year: 2016), Nov. 28, 2016, 18 pages.
Tang, Jessica et al., "Donor-derived cell free DNA (dd-cfDNA) in pregnant kidney transplant recipients", American Journal of Obstetrics & Gynecology, vol. 228, No. 1, 2023.
Avanzini, Stefano et al., "A mathematical model of ctDNA shedding predicts tumor detection size", Science Advances, vol. 6, Issue eabc4308, Dec. 11, 2020, 9 pages.
Chen, Kevin et al., "Commercial ctDNA Assays for Minimal Residual Disease Detection of Solid Tumors", Molecular Diagnosis & Therapy, vol. 25, Issue 6, Nov. 1, 2021, 757-774.
Ge, et al., "Haplotype block: a new type of forensic DNA markers", Int J Legal Med, 2010, 353-361.
Jung, Klaus et al., "Increased cell-free DNA in plasma of patients with metastatic spread in prostate cancer", Cancer Letters, 2004, 173-180.
Kirsch-Gerweck, et al., "HaploBlocks: Efficient Detection of Positive Selection in Large Population Genomic Datasets", Mol. Biol. Evol., 2023.
Bau, Stephan, et al., "Targeted next-generation sequencing by specific capture of multiple genomic loci using low-volume microfluidic DNA arrays", Anal Bioanal Chem, 2009, 171-175.
Lanman, et al., "Analytical and Clinical Validation of a Digital Sequencing Panel for Quantitative, Highly Accurate Evaluation of Cell-Free Circulating Tumor Dna", PLOS ONE, 2015, 1-27.
Lee, et al., "ERBB2 kinase domain mutation in the lung squamous cell carcinoma", Cancer Letters, 2006, 89-94.
Park, et al., "First-Line Erlotinib Therapy Until and Beyond Response Evaluation Criteria in Solid Tumors Progression in Asian Patients With Epidermal Growth Factor Receptor Mutation-Positive Non-Small-Cell Lung Cancer", JAMA Oncol., 2015, 305-312.
Tseng, Jeng-Sen, et al., "Dynamic Plasma EGFR Mutation Status as a Predictor of EGFR-TKI Efficacy in Patients with fGFR-Mutant Lung Adenocarcinoma", Thorac Oncol., 2015, 603-610.
Chan, Allen et al., "Cancer Genome Scanning in Plasma: Detection of Tumor-Associated Copy Number Aberrations, Single-Nucleotide Variants, and Tumoral Heterogeneity by Massively Parallel Sequencing", Clinical Chemistry, 2013, 211-224.
Chan, Allen, "Scanning for Cancer Genomic Changes in Plasma: Toward an Era of Personalized Blood-Based Tumor Markers", Clinical Chemistry, 2013, 1553-1555.
Goessl, C. et al., "DNA Alterations in Body Fluids as Molecular Tumor Markers for Urological Malignancies", European Urology, vol. 41, 2002, 668-676.
Kaper, Fiona et al., "Abstract 1164: Parallel preparation of targeted resequencing libraries from 480 genomic regions using multiplex PCR on the Access Array system", American Association for Cancer Research, 2010, 1-2.
Kaper, Fiona et al., "Parallel Preparation of Targeted Resequencing Libraries from 480 Genomic Regions Using Multiplex PCR on the Access Array System", Fluidigm Poster, 2011, 1.
Wong, I. H. et al., "Quantitative Analysis of Tumor-derived Methylated p161NK4a Sequences in Plasma, Serum, and Blood Cells of Hepatocellular Carcinoma Patients", Clinical Cancer Research, vol. 9, Mar. 2003, 1047-1052.

* cited by examiner

Processor 504

Main Memory 508

User Input/Output Interface(s) 502

User Input/Output Device(s) 503

Secondary Memory 510

Hard Disk Drive 512

Removable Storage Drive 514

Interface 520

Removable Storage Unit 518

Removable Storage Unit 522

Communications Interface 524

Remote device(s), network(s), entity(ies) 528

Communications Path 526

Communication Infrastructure 506

| CASE | FETAL FRACTION | TRUTH | COMPUTED RISK | PRIOR RISK |
|---|---|---|---|---|
| 32440 | 0.02 | Trisomy 13 | 0.210 | 0.0081 |
| 33195 | 0.032 | Triploidy | 0.069 | 0.0009 |
| 39665 | 0.013 | Triploidy | 0.995 | 0.0012 |
| 79709 | 0.022 | Triploidy | 0.880 | 0.0003 |
| 89211 | 0.037 | Triploidy | 0.034 | 0.0008 |
| 98246 | 0.027 | Trisomy 18 | 0.200 | 0.0065 |
| 118211 | 0.028 | Trisomy 18 | 0.149 | 0.0031 |

FIG. 8

Trisomy 13 and 18

NIPT positive cells

NIPT no-call, aneuploidy not detected

NIPT no-call, aneuploidy detected

Triploidy

NIPT positive cells

NIPT no-call, aneuploidy not detected

NIPT no-call, aneuploidy detected

| | |
|---|---|
| High risk of ELFF | 143 |
| Successful follow up | 70 |
| Aneuploid | 7 |
| Trisomy 13 | 1 |
| Trisomy 18 | 2 |
| triploidy | 4 |

FIG. 15

SYSTEMS AND METHODS FOR DETERMINING ANEUPLOIDY RISK USING SAMPLE FETAL FRACTION

CROSS-REFERENCE TO RELATED APPLICATIONS

This application is a continuation of U.S. Utility application Ser. No. 15/186,774, filed Jun. 20, 2016. U.S. Utility application Ser. No. 15/186,774, filed Jun. 20, 2016, claims the benefit of U.S. Provisional Patent Application No. 62/182,085, filed Jun. 19, 2015. Each of these applications cited above is hereby incorporated by reference in its entirety.

This application is filed for procedural purposes only. Applicant expressly does not acquiesce to the rejections issued in U.S. Utility application Ser. No. 15/186,774 to which this application claims priority.

FIELD OF THE INVENTION

The present invention generally relates to molecular biology methods and systems, and more specifically to methods and systems for determining aneuploidy risk in a target maternal blood sample.

BACKGROUND

Noninvasive prenatal testing using cell-free DNA (cfDNA) can be used to detect abnormalities in a fetus. As a result, noninvasive prenatal testing is rapidly becoming part of clinical care for pregnant women.

Noninvasive prenatal testing is used to determine the genetic state of a fetus from genetic material that is obtained in a noninvasive manner, for example from a blood draw on the pregnant mother. The blood could be separated and the plasma isolated, and size selection can optionally be used to isolate the DNA of the appropriate length. This isolated DNA can then be measured by a number of means, such as by hybridizing to a genotyping array and measuring the fluorescence, or by sequencing on a high throughput sequencer.

Single Nucleotide Polymorphism (SNP) based noninvasive prenatal testing is one type of noninvasive prenatal test. SNP based noninvasive prenatal testing is often used to screen for fetal aneuploidies. But the accuracy of SNP based tests is dependent on the amount of fetal DNA present in a maternal blood or plasma sample. SNP based testing returns no call results when the amount of fetal DNA is not sufficient to provide the desired accuracy.

Low amounts of fetal DNA may be caused by a number of factors. One common factor is maternal weight. For example, as maternal weight increases, the amount of fetal DNA in maternal blood plasma, or other fluids often decreases. Thus, SNP based noninvasive prenatal tests that screen for fetal aneuploidies are sometimes unavailable to pregnant women.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 8 illustrates a result set for an example embodiment for fetal fraction-based high risk assessment that predicts an aneuploidy in cases with low fetal fraction.

FIG. 15 illustrates a result set for identified high risk samples, according to an example embodiment.

Figure 1:
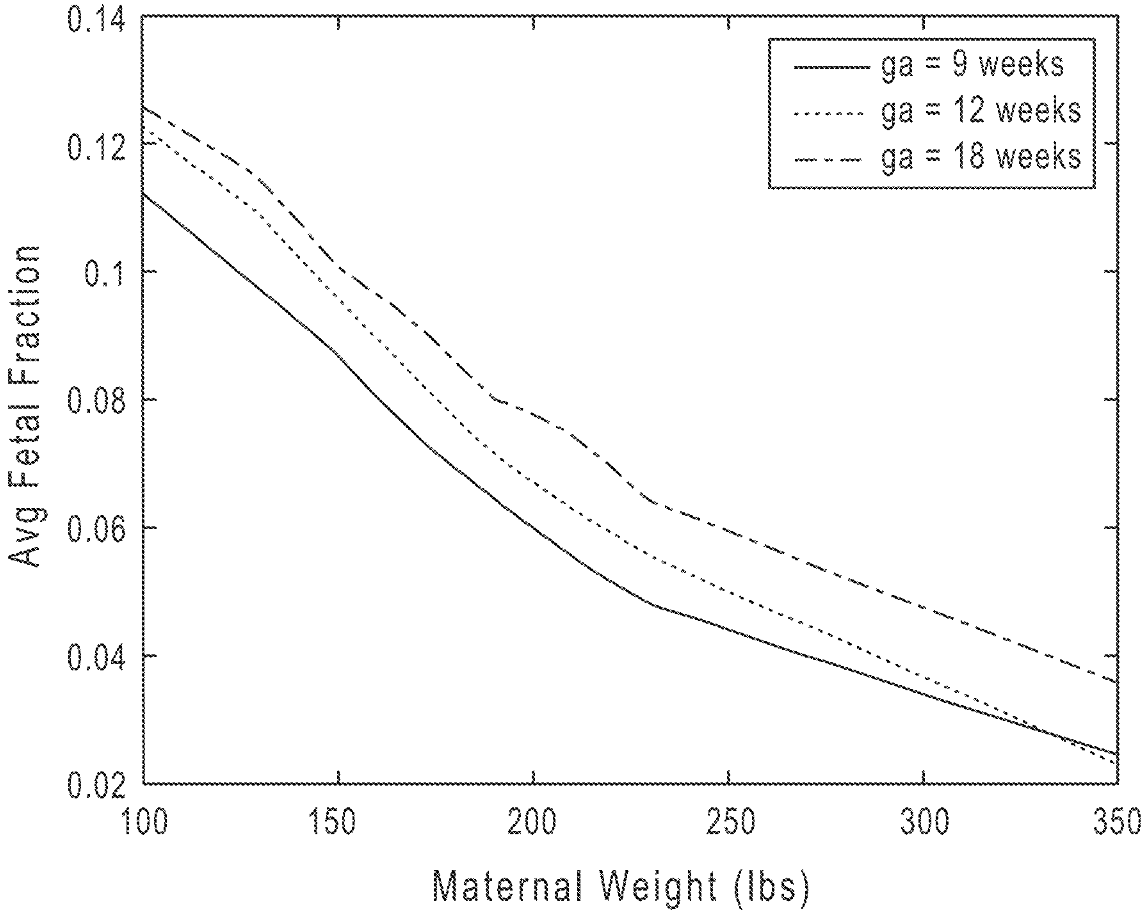
FIG. 1 illustrates a fetal fraction distribution, according to an example embodiment.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Provided herein are system, method and/or computer program product embodiments, and/or combinations and sub-combinations thereof, for determining aneuploidy risk in a target sample of maternal blood, plasma, or other fluid based on the amount of fetal DNA. Such embodiments may be used in situations where a low or extremely low fetal fraction renders traditional aneuploidal risk methodologies inconclusive or inaccurate. For example, such embodiments may be used to determine the risk of trisomy 13, trisomy 18, or maternal triploidy, which are all aneuploidies associated with a low or extremely low fetal fraction. An embodiment operates by receiving genetic data for a target sample (sample of interest) of maternal blood, plasma, or other fluid, and known genetic data from a plurality of known noninvasive prenatal testing samples. A fetal fraction distribution is determined for the received known genetic data based on gestational age and the maternal weight associated with the target sample. A model for a plurality of ploidy states is then generated based on a fixed ratio reduction of the determined fetal fraction distribution. A fetal fraction based data likelihood for the target sample is then determined for each of the plurality of ploidy states using the generated model and the fetal fraction associated with the target sample. An aneuploidy risk score is then output for the target sample based on applying a Bayesian probability determination that combines each fetal fraction based data likelihood with a previously determined risk score as a conditional value. Accordingly, aneuploidy risk can be determined in a target sample even when the sample contains a low amount of fetal DNA. This allows aneuploidy risk to be determined even when SNP based noninvasive prenatal testing would be unreliable or unavailable.

The term "obtaining genetic data" as used herein refers to both, unless indicated otherwise by context, (1) acquiring DNA sequence information by laboratory techniques, e.g. use of an automated high throughput DNA sequencer, and (2) acquiring information that had been previously obtained by laboratory techniques, wherein the information is electronically transmitted to an analyzer, e.g. by computer over the Internet, by electronic transfer from the sequencing device, etc.

The term "aneuploidy" refers to the state where the wrong number of chromosomes are present in a cell. In the case of a somatic human cell it refers to the case where a cell does not contain 22 pairs of autosomal chromosomes and one pair of sex chromosomes. In the case of a human gamete, it refers to the case where a cell does not contain one of each of the 23 chromosomes. In the case of a single chromosome, it refers to the case where more or less than two homologous but nonidentical chromosomes are present, and where each of the two chromosomes originate from a different parent.

The term "ploidy state" refers to the quantity and chromosomal identity of one or more chromosomes in a cell.

Certain aneuploidies are often associated with a reduced amount of fetal DNA in the target sample. For example, trisomy 13, trisomy 18, and maternal triploidy are often associated with a reduced amount of fetal DNA in the target sample. Embodiments of the invention determine aneuploidy risk in a target maternal sample based on a relationship between the amount of fetal DNA in the target sample and the presence of certain aneuploidies.

Figure 6:
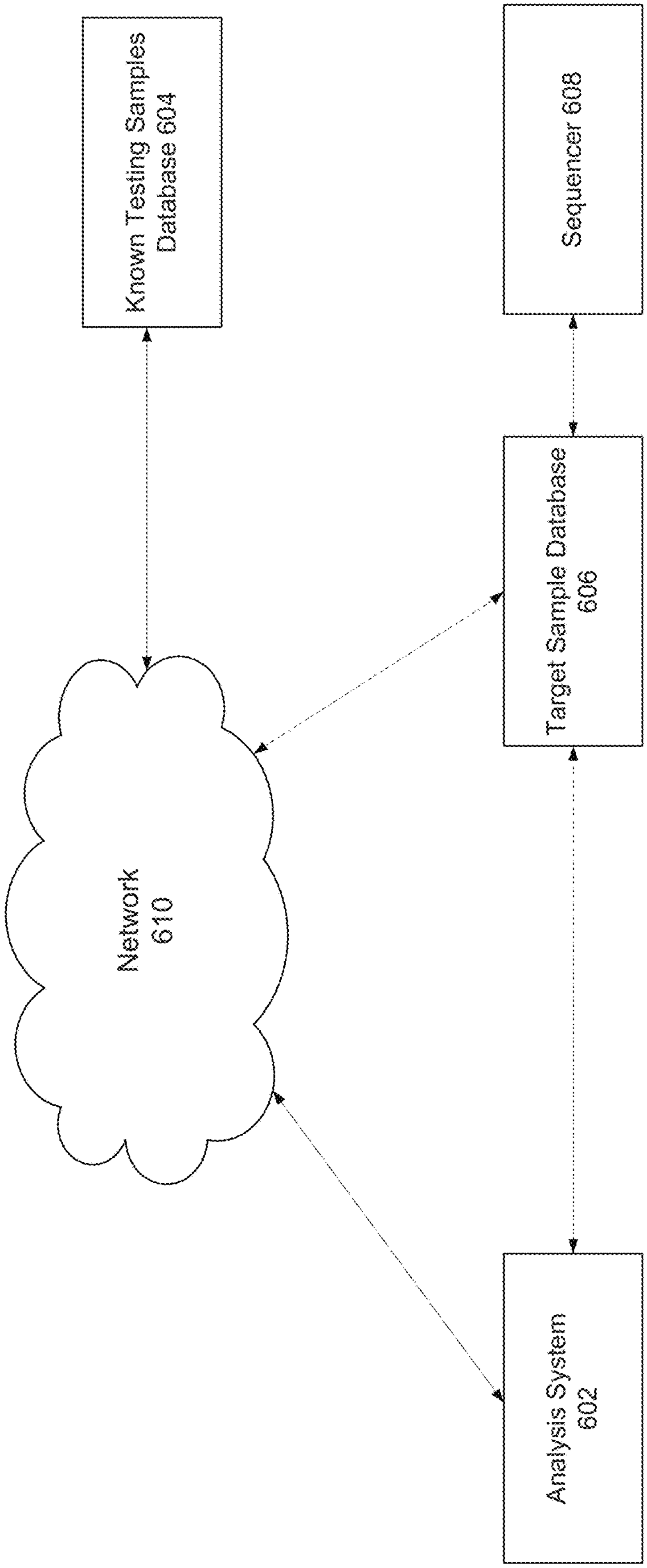
FIG. 6 illustrates an example system for performing embodiments of the present invention.

FIG. 6 illustrates a system for performing embodiments of the present invention. FIG. 6 includes an analysis system 602 for determining a risk of fetal aneuploidy. Analysis system 602 may include one or more processors for executing the functions described herein. Such functions may be implemented on the processor as engines or logical elements that perform the analytical functionality described herein, such as a modeling engine and a probability engine. Interaction of a user with such analytical engines may be conducted through an appropriate user interface. Analysis system 602 may be coupled to a database of known samples 604 via, for example, a network 610. Network 610 may be any type of communication network, including intranets, local area networks, or wide area networks such as the Internet. Genetic data from samples with a known ploidy state may be used to form a baseline for comparison with a target sample in question, as discussed further below. Database 604 may be a collection of data from a variety of sources including clinical studies and commercial data sets.

In an embodiment, a fetal fraction distribution is defined for such known genetic data from the plurality of known prenatal testing samples by analysis system 602. The fetal fraction distribution may be based on the maternal weight and the gestational age corresponding to each sample. This is because gestational age and maternal weight are often factors for the amount of fetal DNA present in a maternal blood sample. A fetal fraction distribution may be defined for known genetic data from a plurality of noninvasive known prenatal testing samples.

The plurality of known prenatal testing samples may be selected based on various criteria to ensure an accurate and representative fetal fraction distribution. In an embodiment, known genetic data for a known prenatal testing sample may be selected or filtered for inclusion in the fetal fraction distribution based on an associated low aneuploidy risk result, a no call result due to low fetal fraction, and a low confidence result. Known genetic data for a known prenatal testing sample may also be selected based on whether the maternal weight associated with the sample is available or whether the sample was collected in a clinical trial in the United States or a foreign country. A selection based on country of origin may be done to prevent unit conversion uncertainty in maternal weight for the sample.

In an embodiment, known genetic data for a plurality of known prenatal testing samples may be grouped into sets according to gestational age and maternal weight. In an embodiment, known genetic data for the plurality of known prenatal testing samples may include sample data taken at a gestational age ranging from 9 to 20 weeks at one week increments. Known genetic data for the plurality of known prenatal testing samples may also include sample data corresponding to a maternal weight ranging from 110 to 250 pounds at 20 pounds increments. In an embodiment, sampling of the known genetic data from known prenatal testing samples may be accurate to within plus or minus ten days of gestational age and plus or minus five pounds of maternal weight.

In an embodiment, the average fetal fraction is computed for the known genetic data in each set of known prenatal testing samples. The standard deviation may also be computed. In an embodiment, the average fetal fraction and standard deviation is only computed for sets of known prenatal testing samples containing at least 50 samples. This may be done to ensure an accurate and representative fetal fraction distribution. The result is a grid of distribution parameters (e.g. average fetal fractions and standard deviations) that correspond to the grid of sample conditions.

FIG. 1 illustrates an example fetal fraction distribution based on known genetic data from a plurality of known prenatal testing samples grouped according to gestational age and maternal weight, according to an example embodiment. In the example of FIG. 1, a set of known prenatal testing samples is grouped together based on the gestational ages of 9 weeks, 12 weeks, and 18 weeks. Moreover, each set of known prenatal testing samples is further grouped together based on maternal weight. The average fetal fraction is computed for the known genetic data of each resulting set of known prenatal testing samples.

For example, in FIG. 1, the average fetal fraction of prenatal testing samples with a maternal weight of 200 lbs. and a gestational age of 9 weeks is around 0.06. The average fetal fraction of prenatal testing samples with a maternal weight of 200 lbs. and a gestational age of 12 weeks is around 0.07. The average fetal fraction of prenatal testing samples with a maternal weight of 200 lbs. and a gestational age of 18 weeks is around 0.08.

Given a particular gestational age and fetal fraction, a fetal fraction distribution may become more symmetric when transformed to log space. Therefore, modeling of fetal fraction may be conducted in log space.

In an embodiment, the fetal fraction distribution may be transformed to a log-normal distribution. In other words, the fetal fraction distribution may transformed to a continuous probability distribution of the fetal fraction whose logarithm is normally distributed. Specifically, the logarithm of the fetal fraction is assumed Gaussian distributed with a mean and standard deviation that are a function of gestational age and maternal weight for the known genetic data of the known prenatal testing samples.

Figure 2:
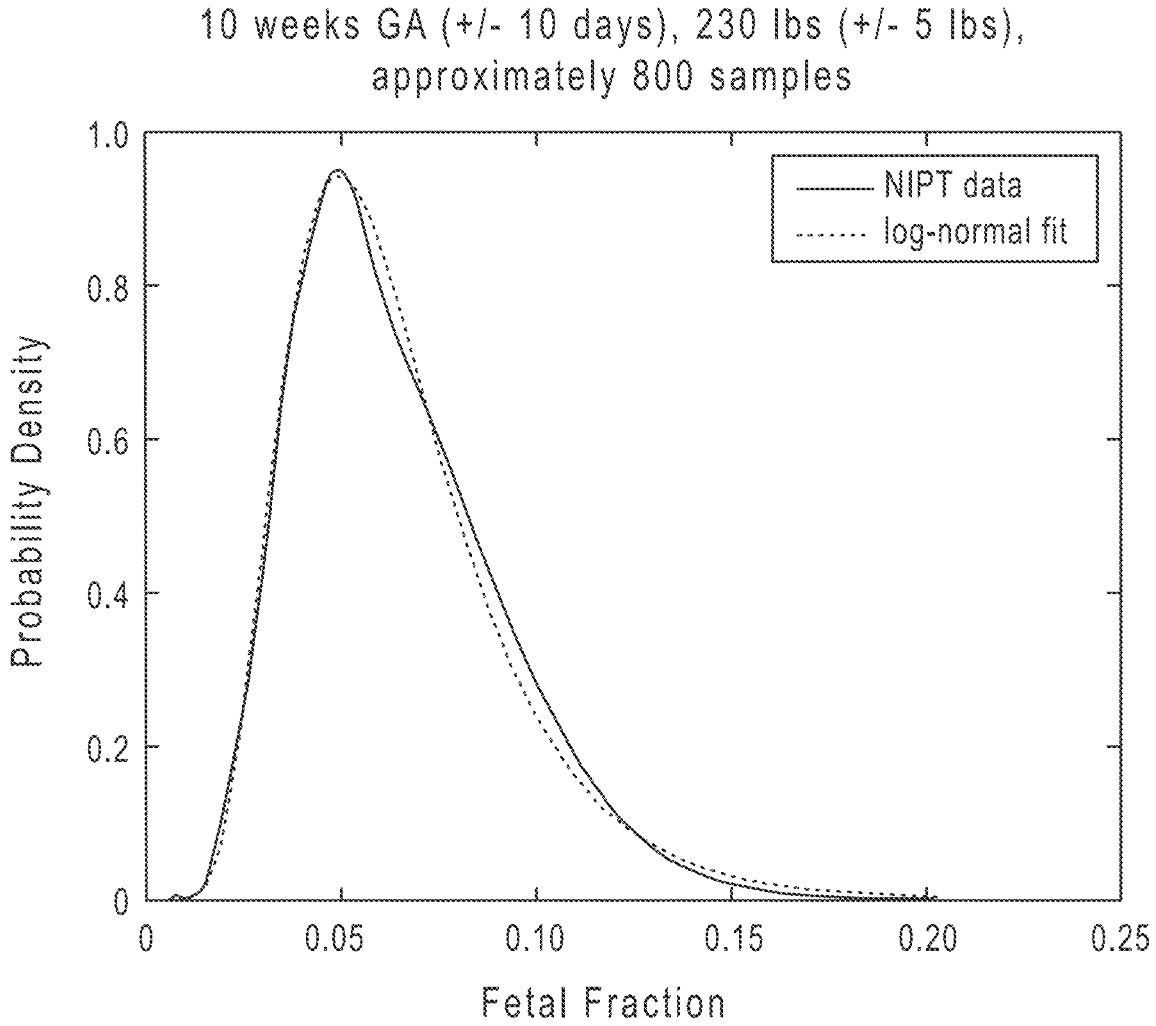
FIG. 2 illustrates a log normal fetal fraction distribution, according to an example embodiment.

FIG. 2 illustrates an example log normal fetal fraction distribution based on the transformation of a fetal fraction distribution to log space, according to an example embodiment. In the example of FIG. 2, the logarithm of the fetal fraction is assumed Gaussian distributed with a mean and standard deviation that are a function of gestational age and maternal weight for the known prenatal testing samples.

In the example of FIG. 2, for known genetic data for around 800 known prenatal testing samples, the gestational age is 10 weeks plus or minus 10 days and the maternal weight is 230 pounds plus or minus 5 pounds. Thus, in FIG. 2, the log normal fetal fraction distribution represents a probability density function (PDF) that describes the relative likelihood for fetal fraction to take on a given value where the gestational age is around 10 weeks plus or minus 10 days and the maternal weight is 230 pounds plus or minus 5 pounds.

In an embodiment, the probability of having an aneuploidy can be computed from the log normal fetal fraction distribution. Specifically, the probability of having an aneuploidy can be computed as the integral of the PDF over a defined range.

In an embodiment, the effect of an aneuploidy may be modeled as a fixed rate reduction in the average fetal fraction compared to the expected average fetal fraction for a given maternal weight and gestational age. For example, the average fetal fraction of a trisomy 13 pregnancy may be 80% of the average fetal fraction for a euploid pregnancy of the same maternal weight and gestational age. Trisomy 13, trisomy 18, and maternal triploidy may be modeled using a fixed rate reduction in the average fetal fraction. As would be appreciated by a person of ordinary skill in the art, the effect of an aneuploidy may be modeled according to various other reductions in the average fetal fraction compared to the expected average fetal fraction for a given maternal weight and gestational age.

In an embodiment, a model may be generated for a plurality of ploidy states based on the fixed ratio reduction of the fetal fraction distribution. A ploidy state may be referred to as a hypothesis.

A fetal fraction distribution may be transformed to a log-normal distribution of fetal fraction prior to generation of a model. In an embodiment, a model may be generated for three hypotheses: trisomy 13, trisomy 18, and maternal triploidy.

In an embodiment for a log-normal distribution of fetal fraction, a fixed rate reduction in the average fetal fraction corresponds to a constant subtracted offset. Thus, for a pregnancy with a particular gestational age and maternal weight, the log fetal fraction for euploid prenatal testing samples is Gaussian distributed with a mean m and a standard deviation s, but the log fetal fraction for prenatal testing samples with an aneuploidy is Gaussian distributed with a mean m-c and a standard deviation s-c where c is a constant subtracted offset for a given aneuploidy. As would be appreciated by a person of ordinary skill in the art, a constant subtracted offset for a given aneuploidy may be determined by an analysis of empirical data.

In an embodiment, there may be a single constant subtracted offset for trisomies 13 and 18 and a different offset for maternal triploidy. In an embodiment, the constant subtracted offset for trisomies 13 and 18 is log(0.79). In other words, in this example, the mean for the trisomy 13 and 18 hypothesis distributions are reduced by log(0.79).

In an embodiment, the constant subtracted offset for maternal triploidy is log(0.22). In other words, in this example, the mean of the maternal triploidy hypothesis distribution is reduced by log(0.22).

Returning to FIG. 6, analysis system 602 may also be coupled to a database 606 containing genetic data for a target sample, either directly or over network 610. Genetic data about the target sample, stored in database 606, may have been obtained from, for example, a sequencer 608. The target sample is one for which a fetal aneuploidy risk is to be determined. While the examples herein will refer to maternal blood, one of skill in the art will recognize that the target sample may be, for example, a maternal blood or plasma containing both maternal DNA and fetal DNA. Such DNA may be, for example, cell-free DNA. As would be appreciated by a person of ordinary skill in the art, a target maternal blood sample that contains fetal DNA may be obtained using various methods.

In some embodiments of the invention, the obtained prenatal target sample is modified using standard molecular biology techniques in order to be sequenced on a DNA sequencer, such as sequencer 608. In some embodiments, the technique will involve forming a genetic library containing priming sites for the DNA sequencing procedure. A plurality of loci may be targeted for site specific amplification. In some embodiments the targeted loci are polymorphic loci, e.g., a single nucleotide polymorphisms. In embodiments employing the formation of genetic libraries, libraries may be encoded using a DNA sequence that is specific for the patient, e.g. barcoding, thereby permitting multiple patients to be analyzed in a single flow cell (or flow cell equivalent) of a high throughput DNA sequencer. Although the samples are mixed together in the DNA sequencer flow cell, the determination of the sequence of the barcode permits identification of the patient source that contributed the DNA that had been sequenced.

Methods are known in the art for obtaining genetic data from a sample. Typically this involves amplification of DNA in the sample, a process which transforms a small amount of genetic material to a larger amount of genetic material that contains a similar set of genetic data. This can be done by a wide variety of methods, including, but not limited to, Polymerase Chain Reaction (PCR), ligand mediated PCR, degenerative oligonucleotide primer PCR, Multiple Displacement Amplification, allele-specific amplification techniques, Molecular Inversion Probes (MIP), padlock probes, other circularizing probes, and combination thereof. Many variants of the standard protocol can be used, for example increasing or decreasing the times of certain steps in the protocol, increasing or decreasing the temperature of certain steps, increasing or decreasing the amounts of various reagents, etc. The DNA amplification transforms the initial sample of DNA into a sample of DNA that is similar in the set of sequences, but of much greater quantity. In some cases, amplification may not be required.

The genetic data of the target sample can be transformed from a molecular state to an electronic state by measuring the appropriate genetic material using tools and or techniques taken from a group including, but not limited to: genotyping microarrays, and high throughput sequencing. Some high throughput sequencing methods and systems include Sanger DNA sequencing, pyrosequencing, the ILLUMINA SOLEXA platform, ILLUMINA's GENOME ANALYZER, ILLUMINA's HISEQ or MISEQ, APPLIED BIOSYSTEM's SOLiD platform, ION TORRENT'S PGM or PROTON platforms, HELICOS's TRUE SINGLE MOLECULE SEQUENCING platform, HALCYON MOLECULAR's electron microscope sequencing method, or any other sequencing method. All of these methods physically transform the genetic data stored in a sample of DNA into a set of genetic data that is typically stored in a memory device en route to being processed.

In an embodiment, a fetal fraction based data likelihood for a target sample may be computed by analysis system 602 for each ploidy state (e.g., trisomy 13, trisomy 18, and maternal triploidy) using the generated model and the fetal fraction associated with the target sample, where each ploidy state corresponds to a hypothesis. Specifically, a fetal fraction based data likelihood for a target sample may be computed for each hypothesis (e.g. trisomy 13, trisomy 18, maternal triploidy, etc.) by evaluating the Gaussian probability density function at the observed log value of the fetal fraction associated with the target sample at each of the three hypotheses.

Figure 3A:
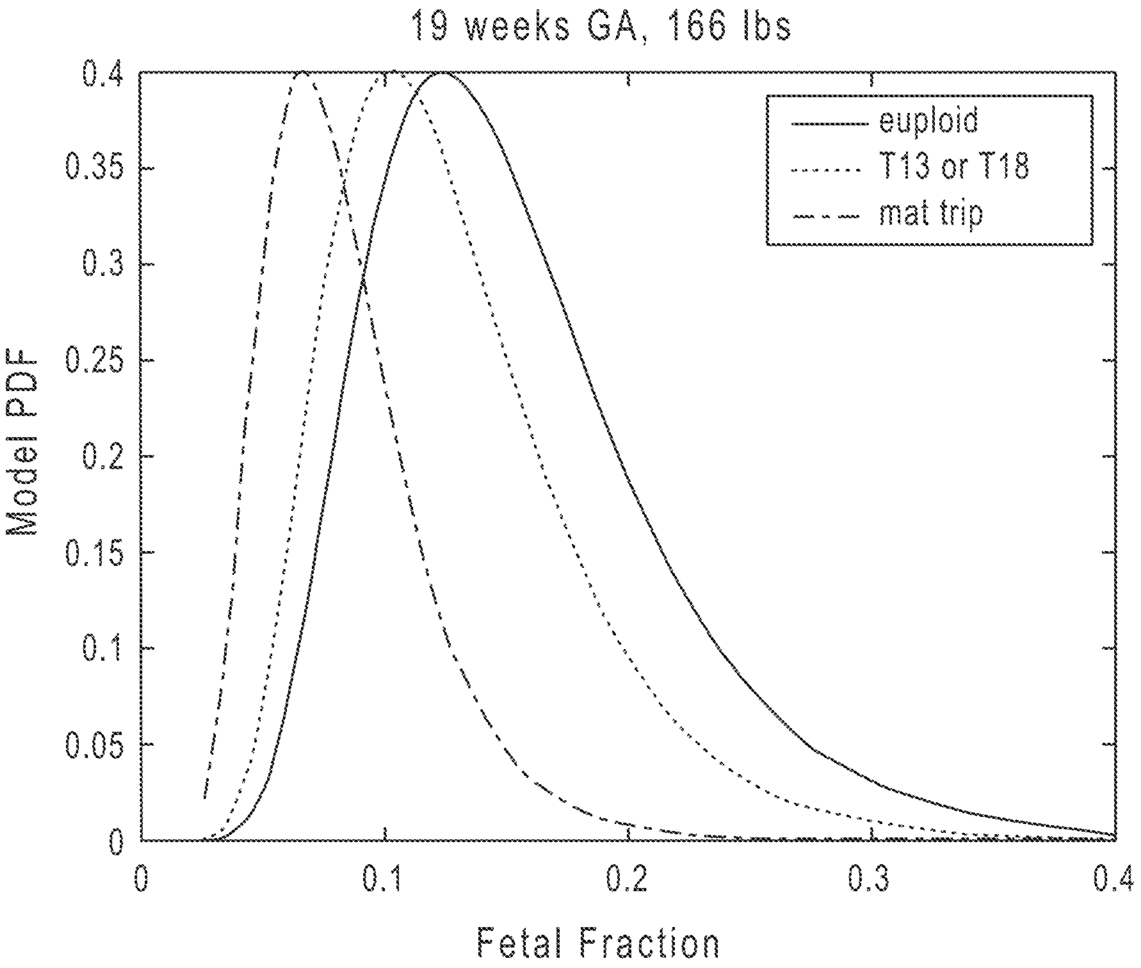
FIG. 3A illustrates a generated model for 19 weeks gestational age, according to an example embodiment.

FIG. 3A illustrates an example of a generated model for trisomy 13, trisomy 18, and maternal triploidy based on a fixed ratio reduction of a determined fetal fraction distribution, according to an embodiment. Specifically, FIG. 3A illustrates an example of a generated model for trisomy 13, trisomy 18, and maternal triploidy where the gestational age is 19 weeks and the maternal weight is 166 pounds. Thus, in FIG. 3A, a fetal fraction based data likelihood for a target sample with a gestational age of 19 weeks and a maternal weight of 166 pounds may be computed for trisomy 13, trisomy 18, and maternal triploidy by evaluating the respective Gaussian probability density function at the observed log value of the fetal fraction associated with the target sample.

For example, in FIG. 3A, the fetal fraction based data likelihood of trisomy 13 or trisomy 18 for a target sample with a fetal fraction of 0.10, a maternal weight of 166 pounds, and a gestational age of 19 weeks is around 35%. Similarly, the fetal fraction based data likelihood of trisomy 13 or trisomy 18 for a target sample with a fetal fraction of 0.20, a maternal weight of 166 pounds, and a gestational age of 19 weeks is around 10%.

Figure 3B:
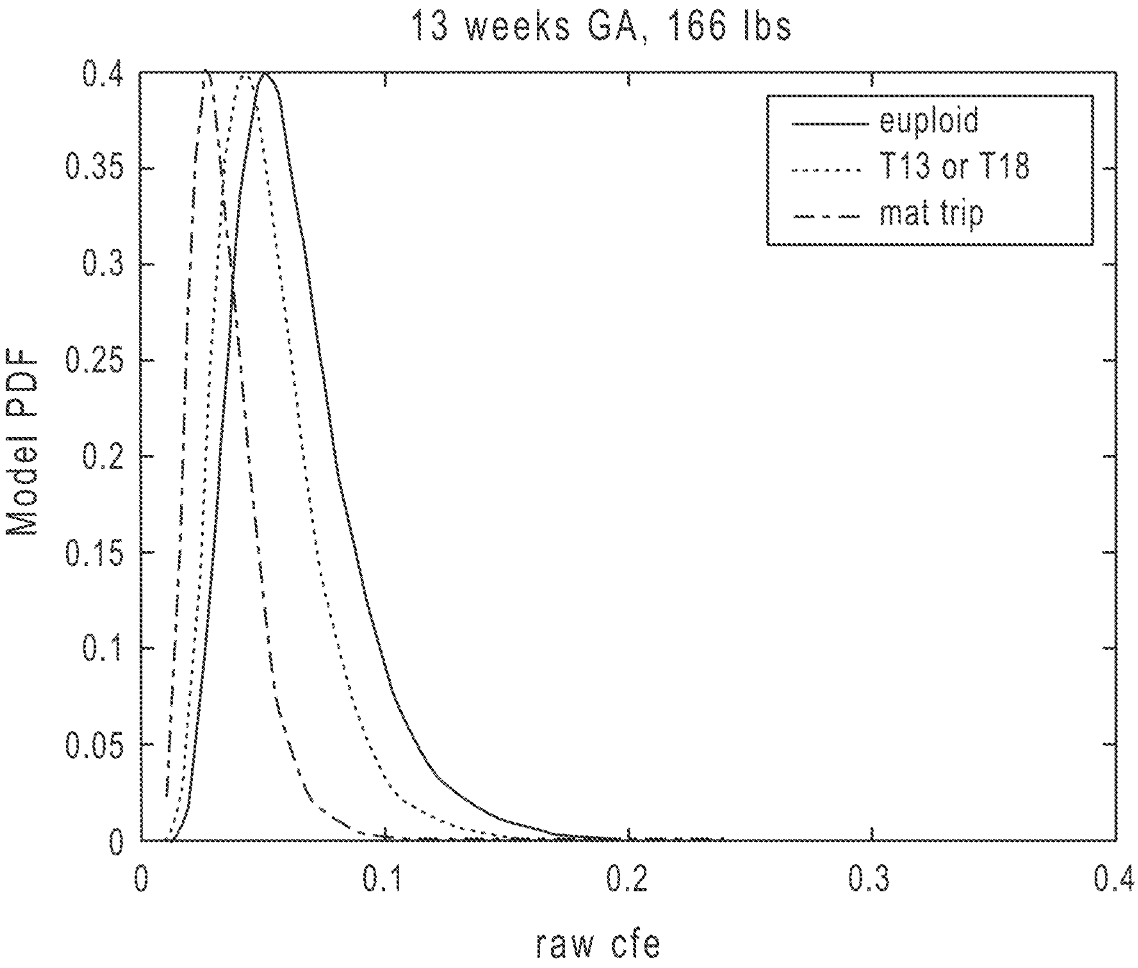
FIG. 3B illustrates a generated model for 13 weeks gestational age, according to an example embodiment.

FIG. 3B illustrates an example of a generated model for trisomy 13, trisomy 18, and maternal triploidy based on a fixed ratio reduction of a determined fetal fraction distribution, according to an embodiment. Specifically, FIG. 3B illustrates an example of a generated model for trisomy 13, trisomy 18, and maternal triploidy where the gestational age is 13 weeks and the maternal weight is 166 pounds. Thus, in FIG. 3B, a fetal fraction based data likelihood for a target sample with a gestational age of 13 weeks and a maternal weight of 166 pounds may be computed for trisomy 13, trisomy 18, and maternal triploidy by evaluating the respective Gaussian probability density function at the observed log value of the fetal fraction associated with the target sample.

By determining fetal fraction based data likelihoods for different ploidy states using a generated model for a target sample, an aneuploidy risk score for the fetus associated with the target sample may be determined. Specifically, in an embodiment, each fetal fraction based data likelihood can be combined with a previously determined risk score in order to determine the aneuploidy risk score for the fetus associated with the target sample. A previously determined risk score may be, for example, an age based prior risk score for the mother associated with the target sample. In another example, a previously determined risk score may be a SNP-based prior risk score. As would be appreciated by a person of ordinary skill in the art, a previously determined risk score may be based on other prior risk factors, including a combination of prior risk factors.

In an embodiment, an aneuploidy risk score for the fetus associated with the target sample may be determined based on the posterior probability of the presence of any of trisomy 13, trisomy 18, and maternal triploidy. Specifically, the fetal fraction based data likelihoods may be combined with previously determined risk scores for trisomy 13, trisomy 18, and maternal triploidy using Bayes' theorem to determine an aneuploidy risk score for the fetus associated with the target sample. In an embodiment, the previously determined risk scores for trisomy 13 and trisomy 18 depend on maternal age and gestational age and may be determined empirically. In an embodiment, the previously determined risk score for maternal triploidy is 1/5505.

Figure 4:
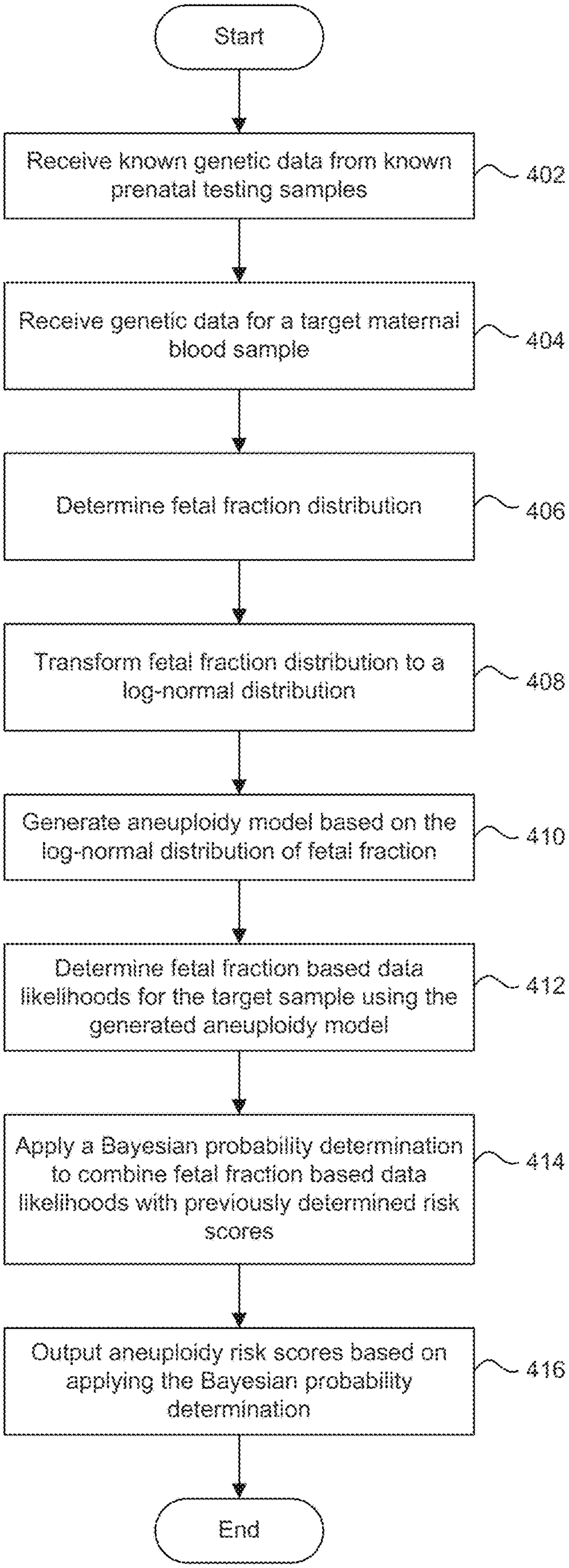
FIG. 4 is a flow chart of a method according to one embodiment of the invention.

FIG. 4 is a flowchart of a method 400 for determining aneuploidy risk in a target maternal blood sample, according to an embodiment. Method 400 can be performed by processing logic that can comprise hardware (e.g., circuitry, dedicated logic, programmable logic, microcode, etc.), software (e.g., instructions run on a processing device), or a combination thereof. Such processing logic may be implemented in, for example, analysis system 602.

In step 402 of FIG. 4, known genetic data from a plurality of known noninvasive prenatal testing samples is received. As would be appreciated by a person of ordinary skill in the art, the known genetic data from the plurality of known prenatal testing samples may be received from a variety of sources including clinical studies and commercial data sets. Moreover, as would be appreciated by a person of ordinary skill in the art, a fetal fraction distribution may be defined for known genetic data from a plurality of noninvasive known prenatal testing samples, a plurality of invasive known prenatal testing samples, or a combination of both.

The received known genetic data from the plurality of known prenatal testing samples may be optionally filtered based on various criteria to ensure that an accurate and representative fetal fraction distribution is determined in step 406. In an embodiment, known genetic data for the known prenatal testing samples may be filtered based on an associated low aneuploidy risk result, a no call result due to low fetal fraction, and a low confidence result. The received known genetic data for the known prenatal testing samples may also be filtered based on whether the maternal weight associated with a sample is available or whether a sample was collected in a clinical in the United States or a foreign country. The filtering based on country of origin may be done to prevent unit conversion uncertainty in maternal weight for a sample.

In step 404 of FIG. 4, genetic data for a target maternal blood sample containing fetal DNA is received. The genetic data includes at least gestational age of the associated fetus, a maternal weight, and a fetal DNA fraction of the target sample. As would be appreciated by a person of ordinary skill in the art, a target maternal blood sample that contains fetal DNA may be obtained using various methods.

In step 406 of FIG. 4, a fetal fraction distribution is determined for the known genetic data from step 402. The determined fetal fraction distribution is based on the maternal weight and the gestational age associated with the target blood sample of step 404. In other words, the received known genetic data for the plurality of known prenatal testing samples is grouped into sets according to gestational age and maternal weight. As discussed above, the sampling of the known genetic data from known prenatal testing samples may be done at various intervals for gestational age and maternal weight.

For each set of known prenatal testing samples, the average fetal fraction is then computed. In an embodiment, the average fetal fraction may only be computed where a set of known prenatal testing samples includes a minimum number of 50 samples. This may be done to ensure an accurate and representative fetal fraction distribution.

In step 408 of FIG. 4, the fetal fraction distribution is transformed to a log-normal distribution. In an embodiment, the logarithm of the fetal fraction is assumed Gaussian distributed with a mean and standard deviation that are a function of gestational age and maternal weight for the received known genetic data of step 402. As would be appreciated by a person of ordinary skill in the art, the log normal fetal fraction distribution represents a PDF that describes the relative likelihood for fetal fraction to take on a given value where the gestational age is equal to gestational age and the maternal weight associated with the received genetic data for the target sample of step 404.

In step 410 of FIG. 4, a model is generated for a plurality of ploidy states based on the log-normal distribution of fetal fraction of step 408. In an embodiment, trisomy 13, trisomy 18, and maternal triploidy distributions are generated from the log-normal distribution of fetal fraction of step 408. This involves reducing the mean for the trisomy 13, trisomy 18, and maternal triploidy distributions by respective constant subtracted offset. As would be appreciated by a person of ordinary skill in the art, the constant subtracted offsets for the trisomy 13, trisomy 18, and maternal triploidy distributions may be determined experimentally.

In step 412 of FIG. 4, fetal fraction based data likelihoods for the received target sample of step 404 are computed for each of the ploidy states using the generated model of step 410 and the fetal fraction associated with the target sample. In an embodiment, a fetal fraction based data likelihood for the received target sample is computed for trisomy 13, trisomy 18, and maternal triploidy by evaluating the Gaussian probability density functions for trisomy 13, trisomy 18, and maternal triploidy at the observed log value of the fetal fraction associated with the target sample.

In step 414 of FIG. 4, a Bayesian probability determination is applied to combine the fetal fraction based data likelihoods of step 412 with previously determined risk scores. As would be appreciated by a person of ordinary skill in the art, a previously determined risk score may be an age based prior risk score for the mother associated with the target sample or an SNP-based prior risk score.

In step 416 of FIG. 4, aneuploidy risk scores for trisomy 13, trisomy 18, and maternal triploidy are output based on the applying in step 414. As would be appreciated by a person of ordinary skill in the art, the outputting may be performed using various methods and mediums.

In an embodiment, the aneuploidy risks scores for trisomy 13, trisomy 18, and maternal triploidy are independently determined. Because each aneuploidy risk score is an independent posterior probability of the presence of either trisomy 13, trisomy 18, or maternal triploidy, the resulting aneuploidy risk scores can be compared to identify the most likely ploidy state.

In an embodiment, a probability that the sample is euploid is also determined and taken into account.

In this manner, an additional type of analysis is made available to individuals whose aneuploidy risk may not be able to be determined by traditional methods, such as SNP-based methods. This analysis may also be used to confirm a previously determined risk score in situations where extremely low fetal fraction is an issue.

Figure 7:
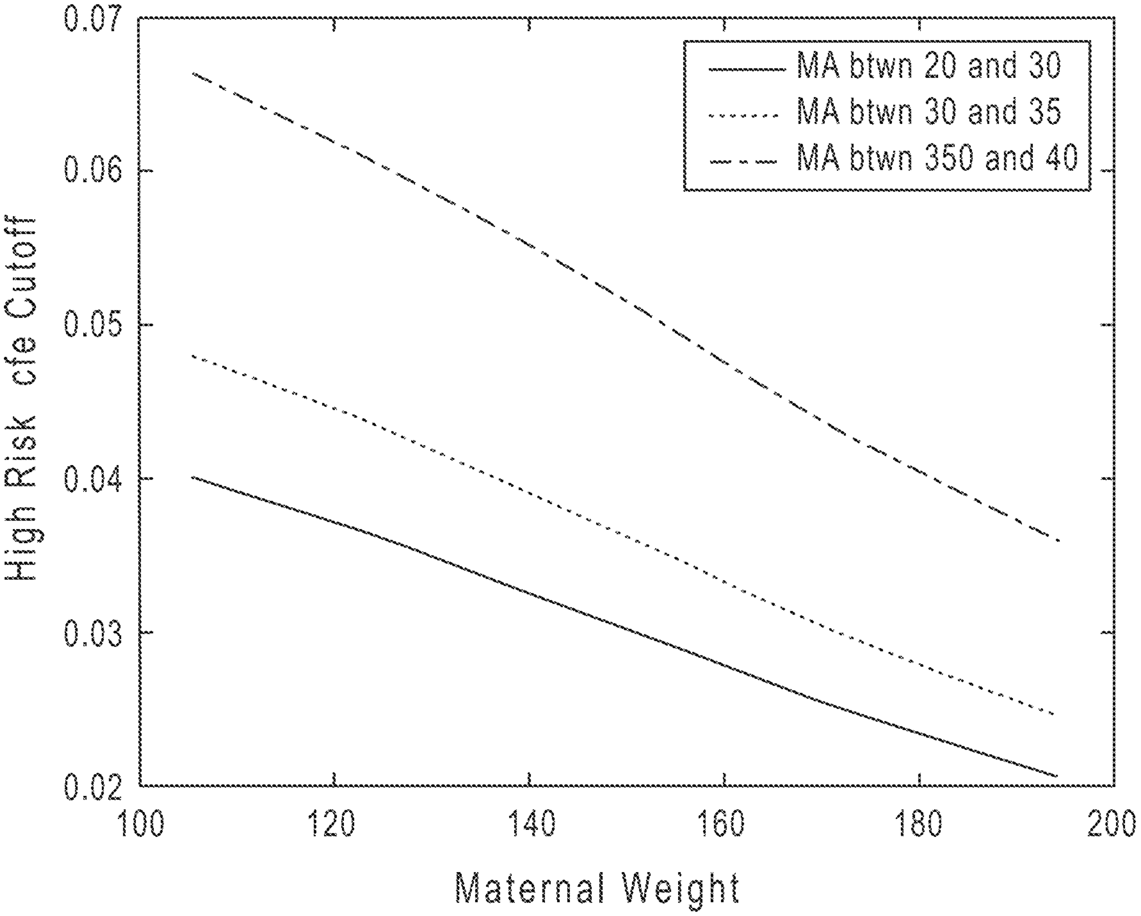
FIG. 7 illustrates a posterior fetal fraction risk distribution, according to an example embodiment.

FIG. 7 illustrates a posterior fetal fraction risk distribution, according to an example embodiment. In the example of FIG. 7, a posterior risk distribution is computed by combining data likelihoods with prior risk for a gestational age between 9 and 11 weeks. The cutoff is at 1/100 risk. This sets the fetal fraction limit for a high risk call.

FIG. 8 illustrates a result set for a pilot study of an example embodiment for fetal fraction-based high risk assessment that predicts an aneuploidy in cases with low fetal fraction. The result set of FIG. 8 indicates that the example embodiment for fetal fraction-based risk assessment is able to predict abnormalities in a clinical data sample set. Specifically, in the example of FIG. 8, there were 143 cases with high risk, low fetal fraction. 70 cases were with karyotype. There was a 10% positive predictive value (PPV) if the associated clinical sample data set was restricted to cases with karyotype and a 4.9% PPV if missing karyotypes were assumed unaffected. FIG. 8 illustrates some of the abnormalities detected in the pilot study.

Figure 9:
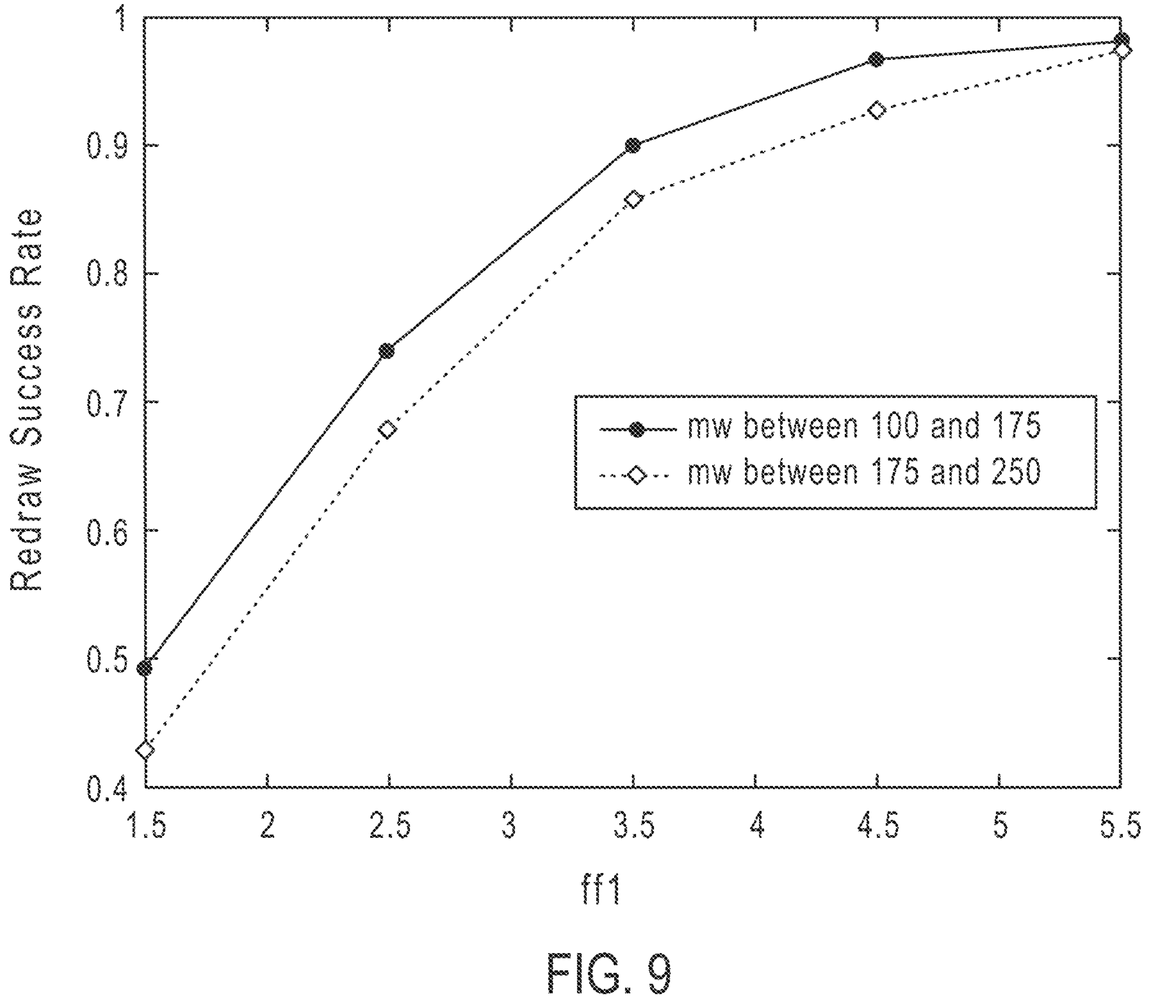
FIG. 9 illustrates a redraw success rate distribution, according to an example embodiment.

FIG. 9 illustrates a redraw success rate distribution, according to an example embodiment. FIG. 9 shows fetal fraction change observed from approximately 3,000 NonInvasive Prenatal Testing (NIPT) redraws. The example embodiment of FIG. 9 provides useful information when an embodiment for NIPT single-nucleotide polymorphism (SNP) fails to provide a prediction. Specifically, the example embodiment of FIG. 9 provides a fetal fraction-based risk score and a probability of successful call on redraw, making it possible to predict redraw success based on a predicted range of redraw fetal fraction.

Figure 10:
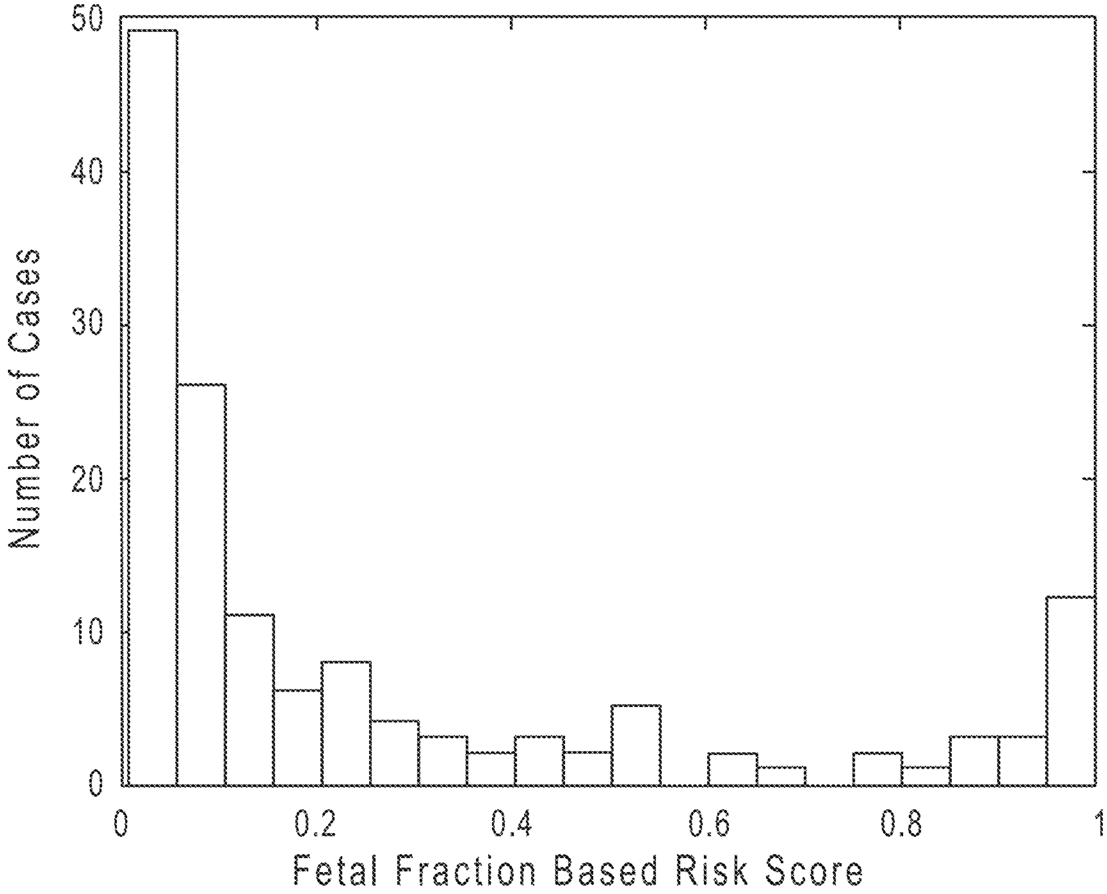
FIG. 10 illustrates a distribution of fetal fraction based risk scores in cases identified as high risk and low fetal fraction, according to an example embodiment.

FIG. 10 illustrates a distribution of fetal fraction based risk scores in cases identified as high risk and low fetal fraction, according to follow up study of an example embodiment. For example, FIG. 10 shows that roughly 5 cases had a fetal fraction based risk score of 0.2. In the follow-up study, the objective was to test whether high fetal fraction-based risk predicts aneuploidy in cases with unusually low fetal fraction. An attempt to collect follow up was made for 896 samples, where the adjusted fetal fraction was below approximately the $2^{nd}$ percentile, and the maternal weight was available. 525 samples were eligible for inclusion in the follow up study, from domestic clinics and direct sales clinics. 143 samples were identified as having high fetal fraction-based risk with low fetal fraction. In particular, the fetal fraction-based risk was greater than 0.01 and the fetal fraction was 2.5 SD below mean. Karyotype was available for 70 samples.

Figure 11A:
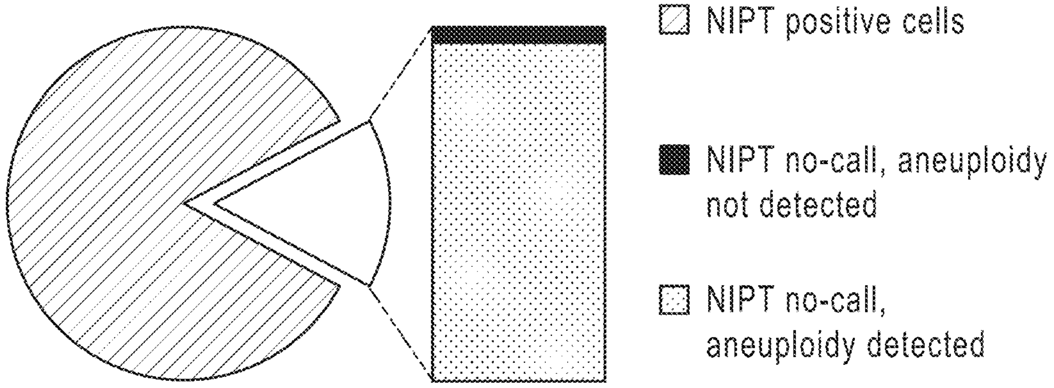
FIG. 11A illustrates an estimated detection rate for trisomy 13 and 18, according to an example embodiment.

FIG. 11A illustrates an estimated detection rate for trisomy 13 and 18, according to an example embodiment. Specifically, FIG. 11A illustrates what fraction of affected cases that are not identified by a NIPT SNP embodiment will be identified by the fetal fraction-based risk score>1/100. The estimated detection rate is based on the sample data set of FIG. 10. In FIG. 11A, the estimated detection rate for trisomy 13/18 is 91.4%.

Figure 11B:
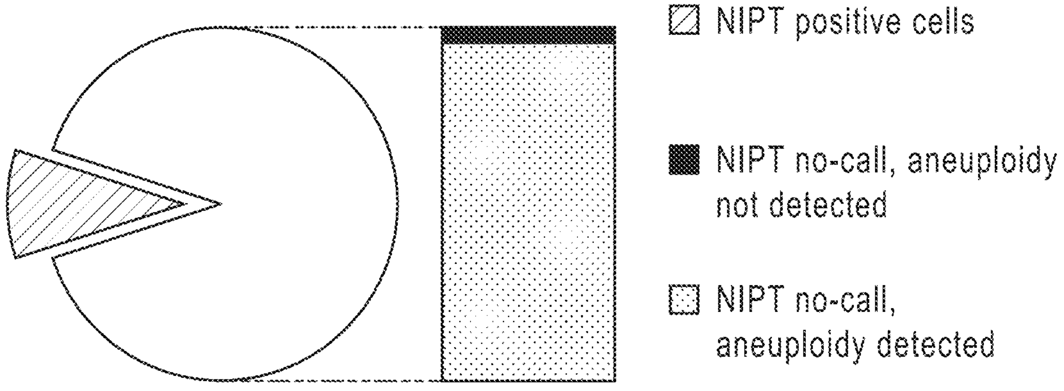
FIG. 11B illustrates an estimated detection rate for digynic triploidy, according to an example embodiment.

FIG. 11B illustrates an estimated detection rate for digynic triploidy, according to an example embodiment. Specifically, FIG. 11B illustrates what fraction of affected cases that are not identified by a NIPT SNP embodiment will be identified by the fetal fraction-based risk score>1/100. The estimated detection rate is based on the sample data set of FIG. 10. In FIG. 11B, the estimated detection rate for digynic triploidy is 96.6%. Retroactive application of such high risk fetal fraction criteria to 29,000 NIPT cases would have resulted in 432 high risk calls (1.5%). Application of the SNP method would result in 115 (0.4%) high risk calls (for T13, T18, digynic triploidy). This results in a 1.8% combined high risk call rate. The expected aneuploidy rate based on priors was 0.3%. The theoretical PPV was thus 16% (0.3%/1.8%).

Figure 12:
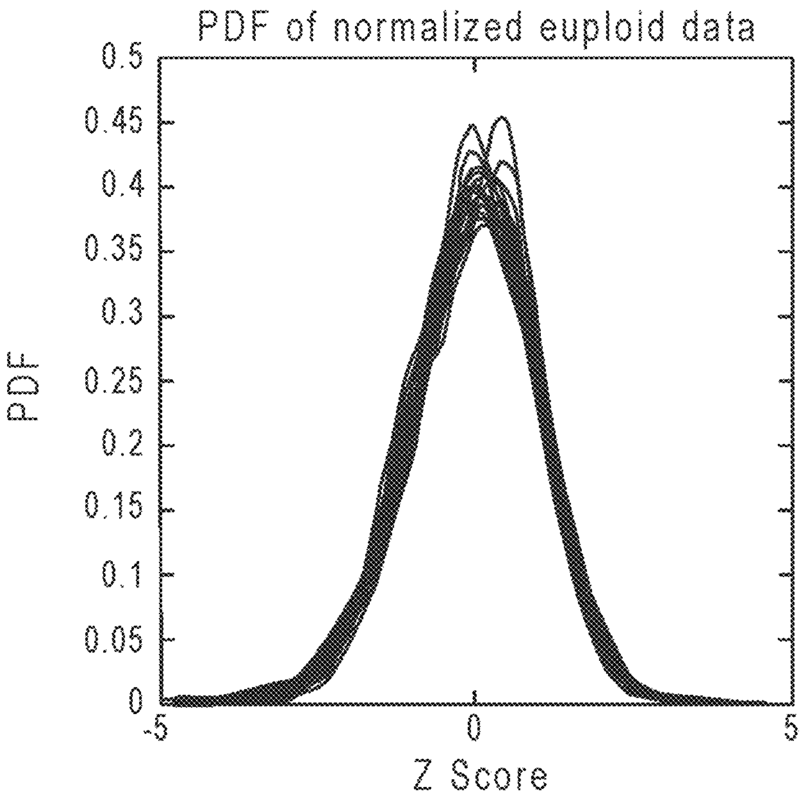
FIG. 12 illustrates a probability density function (PDF) of normalized euploid data, according to an example embodiment.

FIG. 12 illustrates a PDF of normalized euploid data, according to an example embodiment. Specifically, FIG. 12 shows empirical density plots of fetal fractions after normalization. There are 39 density curves. Each of the 39 density curves comes from a set of data with approximately the same maternal weight and gestational age, with between 400 and 500 samples each. Each data set is normalized by its observed mean and variance. The plot in FIG. 12 shows that the Gaussian fit is appropriate because the distributions are very similar.

Figure 13:
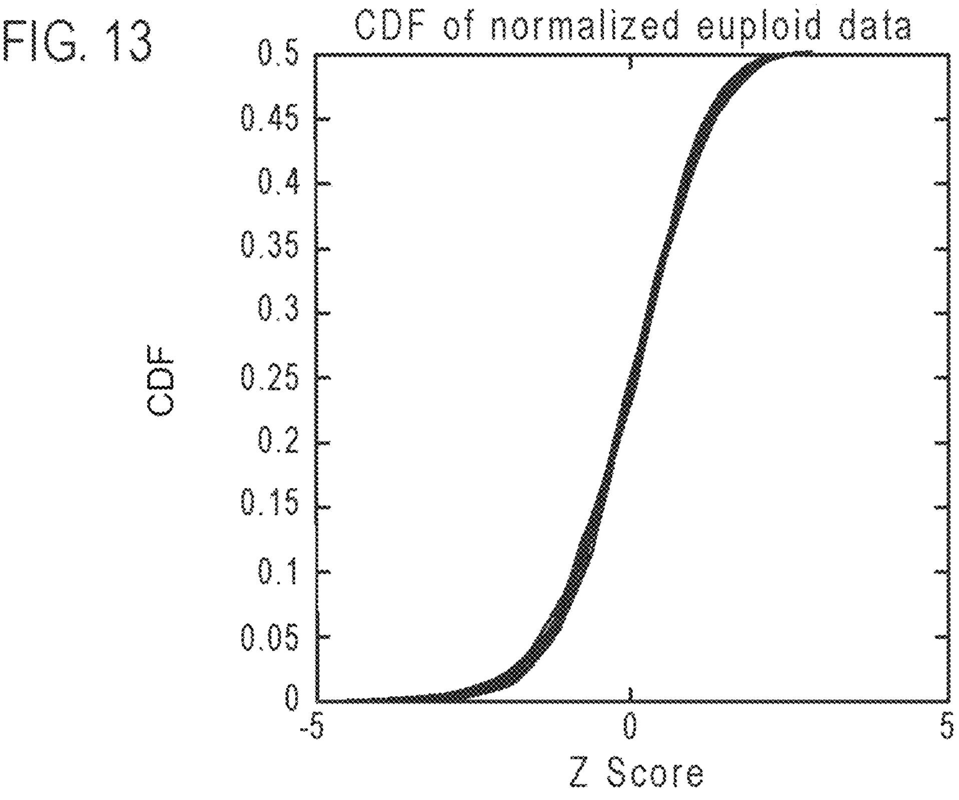
FIG. 13 illustrates a cumulative distribution function (CDF) of normalized euploid data, according to an example embodiment.

FIG. 13 illustrates a CDF of the normalized euploid data of FIG. 12, according to an example embodiment. Specifically, FIG. 13 shows empirical density plots of fetal fractions after normalization. There are 39 density curves. Each of the 39 density curves comes from a set of data with approximately the same maternal weight and gestational age, with between 400 and 500 samples each. Each data set is normalized by its observed mean and variance. The plot in FIG. 13 shows that the Gaussian fit is appropriate because the distributions are very similar.

Figure 14:
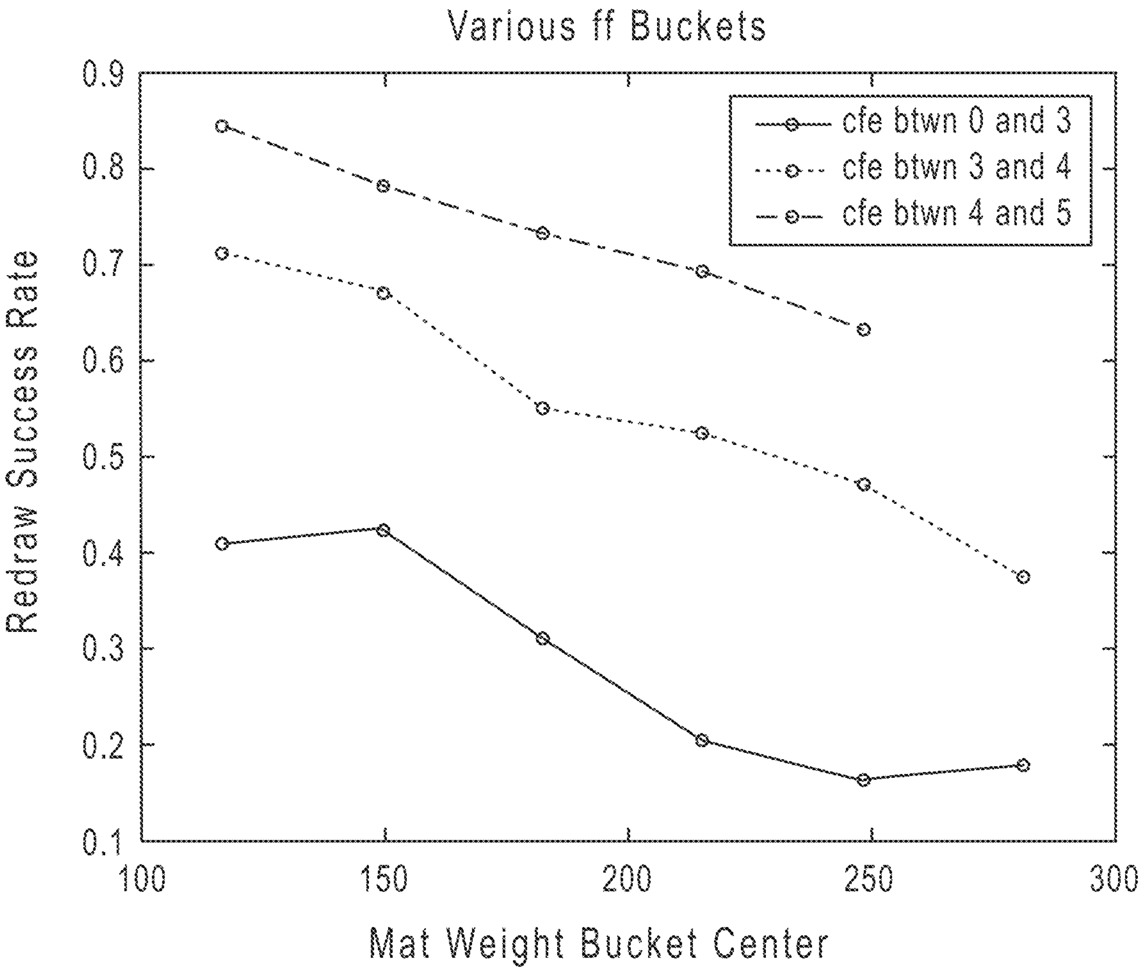
FIG. 14 illustrates a plot of redraw success rate, according to an example embodiment.

FIG. 14 illustrates a plot of redraw success rate, according to an example embodiment. Specifically, FIG. 14 plots the redraw success rate against material weight bucket center. This plots shows that another characteristic of the fetal fraction distribution is the redraw success rate. Specifically, the ability to make a call is strongly dependent on fetal fraction and a successful redraw is often based on an increase in fetal fraction between the first and second draw. The ability to predict the probability of success for a redraw is often useful for doctors and patients. This is because many cases with low fetal fraction will not be at high risk for aneuploidy, but still have low probability of a successful redraw, and so other testing embodiments may be preferred.

FIG. 15 illustrates an example result set for identified high risk samples, according to an embodiment. Specifically, FIG. 15 illustrates a result set for 143 sample cases that were identified as having high extremely low fetal fraction (ELFF) risk based on not having received a successful high or low risk draw call, and having a computed ELFF risk score greater than 0.01. FIG. 15 further illustrates that follow-up results were successfully collected for 70 of these sample cases. Of these 70 sample cases, 7 were found to be aneuploid.

FIG. 15 shows that among the cohort with successful follow-up, the positive predictive value of high ELFF risk is 7/58=12.07%. FIG. 15 further shows that assuming all cases without follow-up are euploid, the positive predictive value is 7/113=6.19%. This value can be considered the lower bound PPV based on the data set of FIG. 15.

Figure 5:
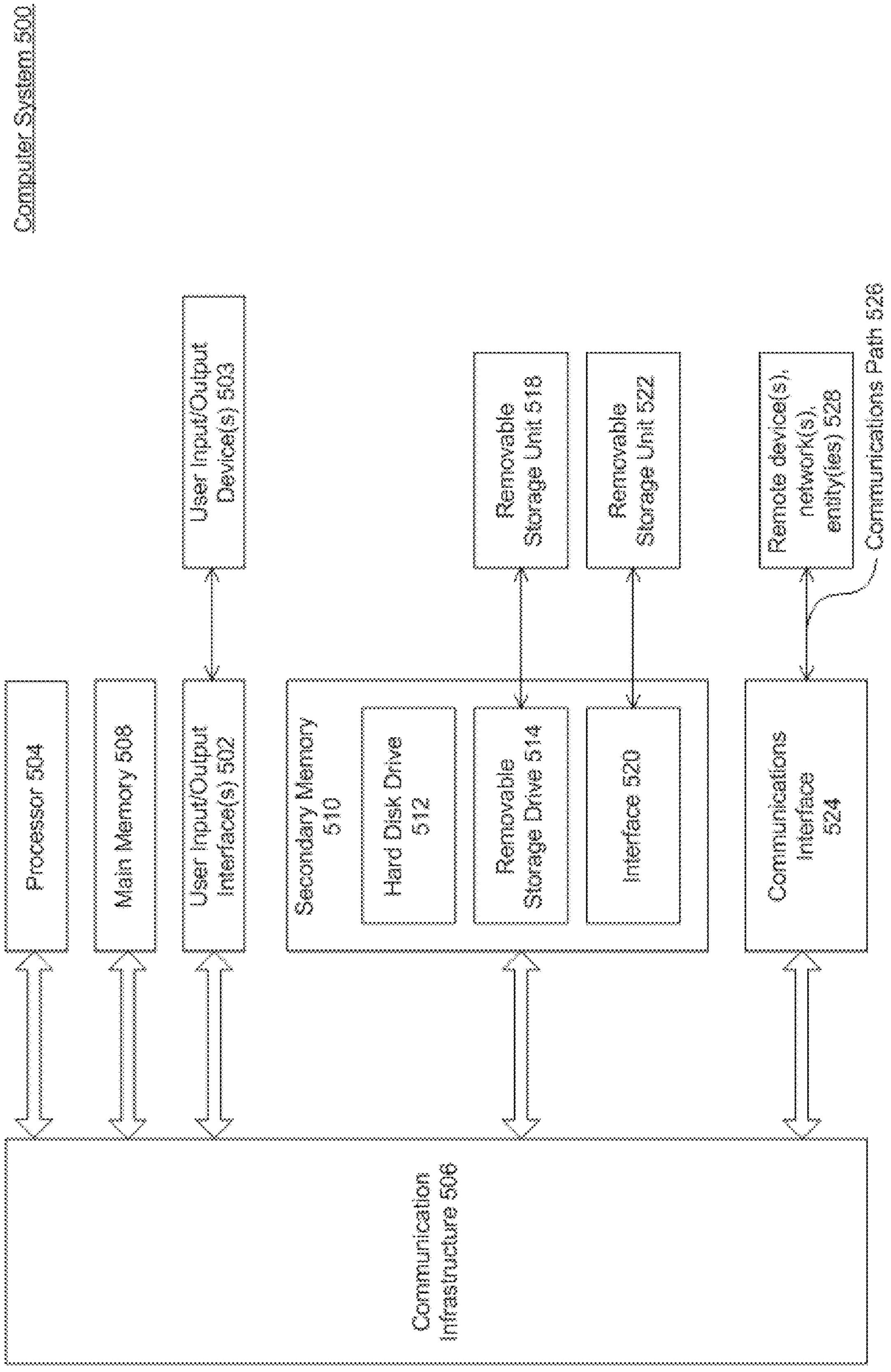
FIG. 5 illustrates an example computer system for performing embodiments of the present invention.

Various embodiments can be implemented, for example, using one or more well-known computer systems, such as computer system 500 shown in FIG. 5. Computer system 500 can be any well-known computer capable of performing the functions described herein.

Computer system 5 includes one or more processors (also called central processing units, or CPUs), such as a processor 5. Processor 504 is connected to a communication infrastructure or bus 506.

One or more processors 504 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 500 also includes user input/output device(s) 503, such as monitors, keyboards, pointing devices, etc., that communicate with communication infrastructure 506 through user input/output interface(s) 502.

Computer system 500 also includes a main or primary memory 508, such as random access memory (RAM). Main memory 508 may include one or more levels of cache. Main memory 508 has stored therein control logic (i.e., computer software) and/or data.

Computer system 500 may also include one or more secondary storage devices or memory 510. Secondary memory 510 may include, for example, a hard disk drive 512 and/or a removable storage device or drive 514. Removable storage drive 514 may be a floppy disk drive, a magnetic tape drive, a compact disk drive, an optical storage device, tape backup device, and/or any other storage device/drive.

Removable storage drive 514 may interact with a removable storage unit 518. Removable storage unit 518 includes a computer usable or readable storage device having stored thereon computer software (control logic) and/or data. Removable storage unit 518 may be a floppy disk, magnetic tape, compact disk, DVD, optical storage disk, and/any other computer data storage device. Removable storage drive 514 reads from and/or writes to removable storage unit 518 in a well-known manner.

According to an exemplary embodiment, secondary memory 510 may include other means, instrumentalities or other approaches for allowing computer programs and/or other instructions and/or data to be accessed by computer system 500. Such means, instrumentalities or other approaches may include, for example, a removable storage unit 522 and an interface 520. Examples of the removable storage unit 522 and the interface 520 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 500 may further include a communication or network interface 524. Communication interface 524 enables computer system 500 to communicate and interact with any combination of remote devices, remote networks, remote entities, etc. (individually and collectively referenced by reference number 528). For example, communication interface 524 may allow computer system 500 to communicate with remote devices 528 over communications path 526, which may be wired and/or wireless, and which may include any combination of LANs, WANs, the Internet, etc. Control logic and/or data may be transmitted to and from computer system 500 via communication path 526.

In an embodiment, a tangible apparatus or article of manufacture comprising a tangible computer useable or readable medium having control logic (software) stored thereon is also referred to herein as a computer program product or program storage device. This includes, but is not limited to, computer system 500, main memory 508, secondary memory 510, and removable storage units 518 and 522, as well as tangible articles of manufacture embodying any combination of the foregoing. Such control logic, when executed by one or more data processing devices (such as computer system 500), causes such data processing devices to operate as described herein.

Based on the teachings contained in this disclosure, it will be apparent to persons skilled in the relevant art(s) how to make and use embodiments of the invention using data processing devices, computer systems and/or computer architectures other than that shown in FIG. 5. In particular, embodiments may operate with software, hardware, and/or operating system implementations other than those described herein.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A method for preparing a non-naturally occurring composition of amplified DNA derived from a target sample of maternal blood or plasma useful for determining an aneuploidy risk score, comprising:

a) extracting cell-free DNA from the target sample of maternal blood or plasma comprising both maternal and fetal cell-free DNA, wherein the target sample has been determined to have a fetal fraction of 0.037 or less;

b) preparing a non-naturally occurring composition of amplified DNA, wherein step (b) comprises amplifying a plurality of targeted single nucleotide polymorphism (SNP) loci from the DNA extracted in (a) to obtain amplified DNA derived from said targeted SNP loci, and performing a barcoding PCR to append a sample barcode onto the amplified DNA; and c) analyzing the non-naturally occurring composition of amplified cell-free DNA by performing high-throughput sequencing or a microarray assay on the amplified DNA obtained in (b) to determine an aneuploidy risk score for the cell-free DNA having a fetal fraction of 0.037 or less.

2. The method of claim 1, wherein step (c) comprises measuring genetic data of the target sample from the non-naturally occurring composition of amplified DNA by high throughput sequencing.

3. The method of claim 1, wherein step (c) comprises measuring genetic data of the target sample from the non-naturally occurring composition of amplified DNA by performing a microarray assay.

4. The method of claim 1, wherein step (c) comprises:

(i) receiving, by one or more processors, known genetic data from at least 50 known noninvasive prenatal testing samples, wherein gestational age and maternal weight are known for the 50 known noninvasive prenatal testing samples;

(ii) receiving, by the one or more processors, the genetic data for the target sample measured by high throughput sequencing or the microarray assay, and a gestational age, a maternal weight, and a fetal fraction associated with the target sample;

(iii) determining, by the one or more processors, a fetal fraction distribution for the received known genetic data based on the gestational age and the maternal weight associated with the target sample;

(iv) generating, by the one or more processors, a model for a plurality of ploidy states based on a fixed rate reduction of the determined fetal fraction distribution compared to an expected average fetal fraction for the gestational age and the maternal weight associated with the target sample;

(v) determining, by the one or more processors, a fetal fraction based data likelihood for the target sample for each of the plurality of ploidy states using the generated model and the fetal fraction associated with the target sample;

(vi) applying, by the one or more processors, a Bayesian probability determination to combine each fetal fraction based data likelihood with a previously determined risk score as a conditional value; and (vii) outputting, by the one or more processors, the aneuploidy risk score for the target sample based on the applying.

5. The method of claim 4, wherein the previously determined risk score is a SNP based risk score.

6. The method of claim 4, further comprising: transforming the determined fetal fraction distribution to logarithm space, wherein a logarithm of the fetal fraction is assumed Gaussian distributed with a mean and standard deviation that are a function of gestational age and maternal weight for the known prenatal testing samples.

7. The method of claim 4, wherein determining a fetal fraction based data likelihood for the target sample comprises determining an integral of a probability density function of the generated model.

8. The method of claim 4, wherein the generated model is associated with trisomy 13.

9. The method of claim 4, wherein the generated model is associated with trisomy 18.

10. The method of claim 4, wherein the generated model is associated with maternal triploidy.

11. The method of claim 4, wherein determining a fetal fraction distribution for the received known genetic data comprises: grouping the genetic data for the at least 50 known prenatal testing samples into sets according to gestational age and maternal weight; and generating a grid of distribution parameters corresponding to each set, wherein the distribution parameters include average fetal fraction and standard deviation.

12. The method of claim 4, wherein the fixed rate reduction in the average fetal fraction correspond to a constant subtracted offset as determined by analysis of empirical data.

13. The method of claim 1, wherein the fetal fraction of cell-free DNA is between 0.013 and 0.037.

14. A method for preparing a non-naturally occurring composition of amplified DNA derived from a target sample of maternal blood or plasma useful for determining an aneuploidy risk score, comprising:

(a) obtaining a target sample of maternal blood or plasma comprising both maternal and fetal cell-free DNA that has been determined to have a fetal fraction of 0.037 or less;

(b) extracting cell-free DNA from the target sample;

(c) preparing a non-naturally occurring composition of amplified DNA, wherein step (c) comprises amplifying a plurality of targeted single nucleotide polymorphism (SNP) loci from the DNA extracted in (b) to obtain amplified DNA derived from said targeted SNP loci, and performing a barcoding PCR to append a sample barcode onto the amplified DNA; and (d) analyzing the non-naturally occurring composition of amplified cell-free DNA by performing high-throughput sequencing or a microarray assay on the amplified DNA obtained in (c).

* * * * *